United States Patent [19]

Frei et al.

[11] 4,115,575
[45] Sep. 19, 1978

[54] 2-(3-AMINO-2-HYDROXY-PROPOXY)-PYRAZINES

[75] Inventors: Jörg Frei, Schönenbuch; Knut A. Jaeggi, Basel; Franz Ostermayer, Riehen; Herbert Schröter, Füllinsdorf, all of Switzerland

[73] Assignee: Ciba-Geigy Corporation, Ardsley, N.Y.

[21] Appl. No.: 757,529

[22] Filed: Jan. 7, 1977

Related U.S. Application Data

[63] Continuation of Ser. No. 590,363, Jun. 25, 1975, abandoned, and a continuation-in-part of Ser. No. 442,711, Feb. 14, 1974, abandoned.

[30] Foreign Application Priority Data

Feb. 20, 1973 [CH] Switzerland ............... 2444/73
Jan. 23, 1974 [FI] Finland ........................ 193/74

[51] Int. Cl.² .............. A61K 31/495; C07D 241/04; C07D 241/12; C07D 241/18

[52] U.S. Cl. .................... 424/250; 544/120; 544/238; 544/239; 544/295; 544/316; 544/357; 544/408; 260/294.8 G; 260/294.9; 260/296 AE

[58] Field of Search ............... 260/250 BN, 268 H; 424/250

*Primary Examiner*—Jose Tovar
*Attorney, Agent, or Firm*—John J. Maitner

[57] ABSTRACT

Heterocyclic compounds of the formula

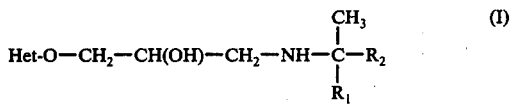

wherein Het denotes optionally substituted pyridazinyl, pyrimidinyl, pyrazinyl or substituted pyridyl, $R_1$ is hydrogen or methyl and $R_2$ is lower alkyl, optionally substituted phenyl-lower alkyl, carboxy-lower alkyl or functionally modified carboxy-lower alkyl, their condensation products with aldehydes, ketones or carbonic acid and their N-oxides, which are valuable (cardioselective) β-rezeptor blocking agents, and/or (cardioselective) β-rezeptor-stimulants.

24 Claims, No Drawings

2-(3-AMINO-2-HYDROXY-PROPOXY)-PYRAZINES

This is a continuation of application Ser. No. 590,363, filed June 25, 1975, now abandoned, which, in turn, is a continuation-in-part of our copending application Ser. No. 442,711, filed Feb. 14, 1974 (now abandoned).

The invention relates to new heterocyclic compounds of the general formula

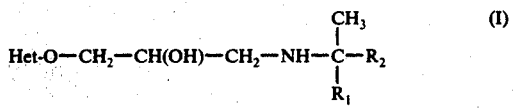

wherein Het denotes optionally substituted pyridazinyl, pyrimidinyl, pyrazinyl or substituted pyridyl, $R_1$ is hydrogen or methyl and $R_2$ is lower alkyl, optionally substituted phenyl-lower alkyl, carboxy-lower alkyl or functionally modified carboxy-lower alkyl, their condensation products with aldehydes, ketones or carbonic acid, their N-oxides and processes for their manufacture.

In the preceding and following text, a lower radical is in particular understood as a radical with up to 7 C atoms, above all with up to 4 C atoms.

Lower alkyl radicals are radicals with, preferably, up to 7 C atoms, above all with up to 4 C atoms, and are, for example, methyl, ethyl, n-propyl, i-propyl or butyl, pentyl, hexyl or heptyl which are unbranched or bonded or branched in any desired position.

Optionally substituted phenyl-lower alkyl radicals are lower alkyl radicals with up to 7 C atoms, above all with up to 4 C atoms, which are substituted in any desired position by optically substituted phenyl groups. Possible phenyl substituents are above all lower alkyl and lower alkoxy groups, the trifluoromethyl radical and halogen atoms. As examples there should be mentioned 3-phenyl-n-propyl or above all benzyl and 2-phenylethyl.

Carboxy-lower alkyl radicals are lower alkyl radicals with, preferably, up to 7 C atoms, above all with up to 4 C atoms, which are substituted in any desired position by carboxyl, such as, for example, 3-carboxy-n-propyl, 4-carboxy-n-butyl and above all carboxymethyl and 2-carboxyethyl.

Functionally modified carboxy-lower alkyl is, for example, esterified carboxy-lower alkyl, amidised carboxy-lower alkyl or cyano-lower alkyl.

Esterified carboxy-lower alkyl is, for example, carboxy-lower alkyl esterified with an aliphatic alcohol. The lower alkyl part of the esterified carboxy-lower alkyl preferably has up to 7 C atoms, above all up to 4 C atoms. Aliphatic alcohols are those in which the hydroxyl group is bonded to a C atom which is not a member of an aromatic system. Suitable aliphatic alcohols are, for example, cycloalkanols, such as those with 3–7, especially 5–7, ring members, for example cyclopropanol, cyclopentanol, cyclohexanol and cycloheptanol, cycloalkyl-lower alkanols, which contains, for example, the above cycloalkyl components, such as cyclopentyl-methanol, cyclohexyl-methanol, 2-cyclohexyl-ethanol and cycloheptyl-methanol, phenyl-lower alkanols, such as 2-phenylethanol and benzyl alcohol, wherein phenyl radicals can also be substituted by halogen, lower alkyl and/or lower alkoxy, such as those mentioned above, and especially lower alkanols, such as n-propanol, iso-propanol, straight-chain or branched butanol, pentanol, hexanol or heptanol, and especially methanol or ethanol. Esterified carboxy-lower alkyl is above all methoxycarbonylmethyl, 2-methoxycarbonyl-ethyl, ethoxycarbonylmethyl and 2-ethoxycarbonyl-ethyl.

Amidised carboxy-lower alkyl is substituted or unsubstituted carbamoyl-lower alkyl. The lower alkyl part of the amidised carboxy-lower alkyl preferably has up to 7 C atoms, above all up to 4 C atoms. Substituted carbamoyl for example has the formula —$CONR_5R_6$, wherein $R_5$ is hydrogen or lower alkyl, $R_6$ is lower alkyl or $R_5$ and $R_6$ together are lower alkylene, oxa-lower alkylene, thia-lower alkylene or aza-lower alkylene. Lower alkylene is branched or especially straight-chain lower alkylene with, in particular, 3–7, above all 4–6, C atoms in the alkylene chain: Oxa-lower alkylene is branched or especially straight-chain oxa-lower alkylene with, in particular, 4 or 5 C atoms in the oxa-alkylene chain. Thia-lower alkylene is branched or especially straight-chain thia-lower alkylene with, in particular, 4 or 5 C atoms in the thiaalkylene chain. Aza-lower alkylene is branched or straight-chain aza-lower alkylene with, in particular, 2–6, above all 4–6, C atoms in the aza-alkylene chain. Amidised carboxy-lower alkyl is accordingly above all carbamoylmethyl, 2-carbamoylethyl, N,N-dimethylcarbamoylmethyl, 2-(N,N-dimethylcarbamoyl)-ethyl, N,N-diethylcarbamoylmethyl, 2-(N,N-diethylcarbamoyl)-ethyl, pyrrolidinocarbonylmethyl, 2-pyrrolidinocarbonylethyl, piperidinocarbonylmethyl, 2-piperidinocarbonylethyl, morpholinocarbonylmethyl, 2-morpholinocarbonylethyl, thiomorpholinocarbonylmethyl, 2-thiomorpholinocarbonylethyl, 2,6-dimethylthiomorpholinocarbonylmethyl, 2-(2',6'-dimethylthiomorpholinocarbonyl)-ethyl, piperazinocarbonylmethyl, 2-piperazinocarbonylethyl, N'-methylpiperazinocarbonylmethyl, 2-(N'-methylpiperazino)-carbonylethyl, N'-(β-hydroxyethyl)-piperazino-carbonylmethyl or 2-[N'-(β-hydroxyethyl)-piperazino]-carbonylethyl.

Cyano-lower alkyl preferably has up to 7 C atoms and above all up to 4 C atoms in the lower alkyl part and is, for example 3-cyano-n-propyl, 4-cyano-n-butyl, 5-cyano-n-pentyl and above all 2-cyanoethyl and cyanomethyl.

Het is optionally substituted pyrazinyl of the formula

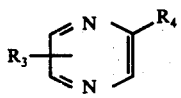

or optionally substituted pyrimidinyl of the formula

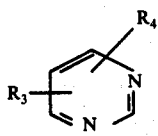

or optionally substituted pyridazinyl of the formula

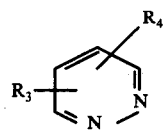

wherein R₃ is hydrogen, halogen, nitrile, hydroxyl, lower alkyl, lower alkoxy-lower alkyl, amino-lower alkyl, lower alkoxy-lower alkenyl, lower alkylamino, di-lower alkylamino, acylamino, acylamino-lower alkyl, acylamino-lower alkenyl or lower alkysulphonyl and R₄ is hydrogen, halogen, lower alkyl, hydroxy-lower alkyl, lower alkenyl, optionally substituted phenyl, hydroxyl, lower alkoxy, lower alkoxy-lower alkyl, amino-lower alkyl, lower alkoxy-lower alkoxy, lower alkenyloxy, lower alkylthio, lower alkylthio-lower alkoxy, lower alkylthio-lower alkyl, lower alkyleneamino, hydroxy-lower alkyleneamino, oxa-lower alkyleneamino, thia-lower alkyleneamino, aza-lower alkyleneamino, optionally substituted carbamoyl, lower alkylamino, di-lower alkylamino, optionally substituted phenylthio, acylamino, lower alkylsulphonyl or lower alkoxycarbonyl or Het is substituted pyridyl of the formula

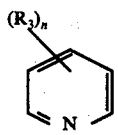

wherein R₃ is halogen, nitrile, nitro, lower alkyl, hydroxy-lower alkyl, lower alkenyl, optionally substituted phenyl, hydroxyl, lower alkoxy, lower alkoxy-lower alkyl, lower alkoxy-lower alkenyl, lower alkoxy-lower alkoxy, lower alkylthio-lower alkyl, lower alkenyloxy, lower alkylthio, lower alkylthio-lower alkoxy, lower alkyleneamino, hydroxy-lower alkyleneamino, oxa-lower alkyleneamino, thia-lower alkyleneamino, aza-lower alkyleneamino, lower alkylamino, di-lower alkylamino, acylamino, acylamino-lower alkyl, acylamino-lower alkenyl, amino-lower alkyl, optionally substituted carbamoyl, optionally substituted carbamoyl-lower alkyl or lower alkylsulphonyl and n is 1, 2 or 3, it also being possible for the substituents R₃ to be different from one another if n is 2 or 3.

Condensation products of compounds of the formula I with an aldehyde or ketone are those of the formula Iy

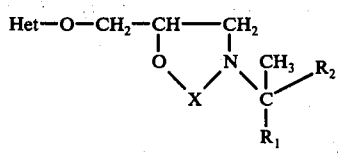

wherein Het, R₁ and R₂ have the above meaning and X represents a divalent radical of an aldehyde or ketone. Examples of suitable ketones are lower alkanones, such as acetone. Examples of suitable aldehydes are lower alkanals such as those with up to 7 C atoms, especially with up to 4 C atoms, such as acetaldehyde or above all formaldehyde, and also aryl-lower alkanals, such as phenyl-lower alkanals which are optionally substituted in the phenyl part by lower alkyl, lower alkoxy, halogen or trifluoromethyl groups, but are preferably unsubstituted, and wherein the lower alkanal part in particular has the above meaning, such as, for example, benzaldehyde.

Condensation products of compounds of the formula I with carbonic acid are those of the formula Iz

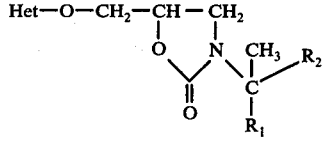

wherein Het, R₁ and R₂ have the above meanings.

The new compounds possess valuable pharmacological properties. The main action of the substituted pyridines, pyrazines and pyrimidines consists of a blocking of adrenergic β-receptors which can be domonstrated, for example as an inhibiting action against effects of known β-receptor-stimulants in various organs: Inhibition of isoproterenol tachycarida on isolated guineapig hearts and of isoproterenol relaxation on isolated guineapig trachea at concentrations of 0.001 to 3 μg/ml and inhibition of isoproterenol tachycardia and isoproterenol vasodilation on narcotised cats on intravenous administration of 0.01 to 30 mg/kg. The compounds mentioned either belong to the class of the non-cardioselective β-receptor blocking agents, that is to say they block the β-receptors on the vessels or in the trachea in similar or even lower doses or concentrations to the β-receptors in the heart, or they belong to the class of the so-called cardioselective β-receptor blocking agents, that is to say they block the β-receptors of the heart even in a dosage range or concentration range which is as yet inadequate to block the β-receptors in the vessels or in the trachea. As an additional property, some of these compounds possess a so-called "intrinsic sympathomimetic activity (ISA)", that is to say that in addition to the β-blocking action (= main action) these compounds produce a partial β-stimulation. The main action of unsubstituted pyrazine and pyrimidine as well as of pyrimidine substituted by hydroxyl consists of a stimulation of the adrenergic β-receptors which can be demonstrated, for example, on the heart, as a positively inotropic and positively chronotropic action. On isolated guineapig auricles the compounds mentioned increase the hearbeat frequency and myocardiac contraction force at concentrations of 0.01 to 10 μg/ml whilst in narcotised cats they do so on intravenous administration of 0.001 to 1 mg/kg. In concentrations which are distinctly higher than those required for β-stimulation, these compounds also display a β-receptorblocking property. 5-Hydroxy-(2'-hydroxy-3'-isopropylaminopropoxy)-pyrimidine however clearly differs qualitatively from known β-receptor-stimulants in that, on narcotised cats, it only lowers the arterial blood pressure at a dose of 1 mg/kg given intravenously, that is to say in a dosage range which is distinctly above that required to increase the myocardiac contraction force and hearbeat fequency. On isolated guineapig trachea the compound does not show a relaxing action at concentrations as low as 10 μg/ml. Because of this property, this compound can be described as cardioselective β-receptor-stimulant.

The new compounds therefore are useful for the treatment of illnesses of the cardiac and circulatory system. For example, the β-receptor blocking agents can be used for the therapy of angina pectoris, hypertonia and disturbances of the rhythm of the heart. The cardioselective preparations offer the advantage, over non-cardioselective preparations, that at the doses which are required for blockage of the β-receptors of the heart, no blockage of β-receptors in other organs is as yet to be expected. The risk of triggering undesired side-effects such as, for example, a bronchial spasm, is accordingly very low. In contrast to the cardioselective preparations, the non-cardioselective preparations either block the β-receptors in all organs approximately equally or preferentially in certain organs (such as, for example, in the vessels).

The β-receptor stimulants are useful as cardiotonics for the treatment of insufficiency of the cardiac muscle (by themselves or in combination with other preparations such as, for example, cardiac glycosides). As compared to known β-receptor stimulants, these compounds show the following advantages: Because of the pharmacologically domonstrated cardioselectivity, it can be expected that the myocardiac contraction force will be increased without at the same time causing an undesired lowering of the blood pressure. Furthermore, only a slight rise in the heartbeat frequency is to be expected because the reflex tachycardia which occurs as the consequence of the lowering of the blood pressure does not arise. However, they can also be used as valuable intermediate products for the preparation of other useful materials, especially pharmaceutically active compounds.

For compounds of the formula I wherein Het is optionally substituted pyrazinyl, formula I represents, for example, compounds of the general formula Ia

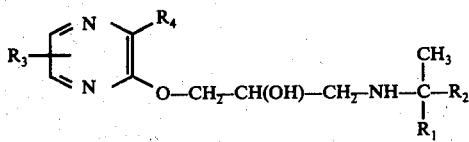

and their condensation products with aldehydes, ketones or carbon dioxide, and the corresponding N-oxides, wherein $R_1$ and $R_2$ have the same meanings as above, $R_3$ is hydrogen, halogen, nitrile, hydroxyl, lower alkyl, lower alkoxy-lower alkyl, amino-lower alkyl, lower alkoxy-lower alkenyl, lower alkylamine, di-lower alkylamino, acylamino, acylamino-lower alkyl, acylamino-lower alkenyl or lower alkylsulphonyl and $R_4$ is hydrogen, halogen, lower alkyl, hydroxy-lower alkyl, lower alkenyl, optionally substituted phenyl, hydroxyl, lower alkoxy, lower alkoxy-lower alkyl, amino-lower alkyl, lower alkoxy-lower alkoxy, lower alkenyloxy, lower alkylthio, lower alkylthio-lower alkoxy, lower alkylthio-lower alkyl, lower alkyleneamino, hydroxy-lower alkyleneamino, oxa-lower alkyleneamino, thia-lower alkyleneamino, aza-lower alkyleneamino, optionally substituted carbamoyl, lower alkylamino, di-lower alkylamino, optionally substituted phenylthio, acylamino, lower alkylsulphonyl or lower alkoxycarbonyl.

In the preceding and following text, a lower radical is in particular understood as a radical with up to 7 C atoms, above all with up to 4 C atoms.

Lower alkyl radicals preferably have up to 7 C atoms, above all up to 4 C atoms, and are, for example, methyl, ethyl, n-propyl, i-propyl or butyl, pentyl, hexyl or heptyl which are unbranched or bonded or branched in any desired position.

Hydroxy-lower alkyl preferably has up to 7 C atoms in the lower alkyl part, above all up to 4 C atoms, and is, for example, 3-hydroxy-propyl, 2-hydroxy-propyl, 1-methyl-2-hydroxy-ethyl or hydroxybutyl, hydroxypentyl, hydroxyhexyl or hydroxyheptyl which are unbranched or bonded or branched in any desired position, and above all hydroxymethyl and 2-hydroxyethyl.

Lower alkenyl preferably has up to 7 C atoms and above all up to 4 C atoms, such as vinyl, 2-methylvinyl, methallyl and especially allyl.

Suitable substituents for optionally substituted phenyl are halogen, trifluoromethyl, lower alkyl, lower alkenyl, lower alkoxymethyl, lower alkoxy and lower alkenyloxy. Optionally substituted phenyl is thus above all phenyl, chlorophenyl, bromophenyl, trifluoromethylphenyl, tolyl, methoxymethylphenyl, methoxyphenyl, ethoxyphenyl and allyloxyphenyl.

Lower alkoxy radicals preferably have up to 7 C atoms, above all up to 4 C atoms, such as, for example, ethoxy, propoxy, i-propoxy, straight or branched butyloxy, pentyloxy, hexyloxy or heptyloxy bonded in any desired position, or, above all, methoxy.

Lower alkoxy-lower alkyl preferably has up to 7 C atoms, above all up to 4 C atoms, in the lower alkyl part of the lower alkoxy part, such lower alkyl parts being iso- or n-propyl, straight or branched butyl, pentyl, hexyl or heptyl bonded in any desired position, especially ethyl and above all methyl. The lower alkyl part which carries the lower alkoxy part preferably has up to 7 C atoms, above all up to 4 C atoms. For example, lower alkoxy-lower alkyl is methoxymethyl, 2-ethoxyethyl, 3-methoxy-n-propyl, 3-ethoxy-n-propyl, 4-methoxy-n-butyl or above all 2-methoxyethyl and ethoxymethyl.

Lower alkoxy-lower alkenyl are lower alkenyl radicals with, preferably, up to 7 C atoms and above all up to 4 C atoms, which are substituted by lower alkoxy in any desired position. Lower alkoxy preferably has up to 7 C atoms and above all up to 4 C atoms in the lower alkyl part. Lower alkoxy-lower alkenyl is thus preferably 2-methoxyvinyl, 2-ethoxyvinyl and above all 3-methoxyallyl and 3-ethoxyallyl.

Lower alkenyloxy radicals are radicals with, preferably, up to 7 C atoms, eespecially with 3 or 4 C atoms, such as the methallyloxy or above all the allyloxy radical.

Lower alkoxy-lower alkoxy has up to 7 C atoms, above all up to 4 C atoms, in each lower alkyl part and is, for example, methoxymethoxy, ethoxymethoxy, 2-methoxyethoxy, 4-methoxy-n-butoxy and especially 3-methoxy-n-propoxy.

Lower alkylthio radicals preferably have up to 7 C atoms, above all up to 4 C atoms, such as, for example, ethylthio, n-propylthio, n-butylthio, i-propylthio or especially methylthio.

Lower alkylthio-lower alkoxy radicals preferably have up to 7 C atoms, above all up to 4 C atoms, in each of the two lower alkyl parts, such as, for example, methylthiomethoxy, ethylthiomethoxy, propylthiomethoxy, 3-methylthiopropoxy, 3-ethylthiopropoxy, 3-propylthiopropoxy and above all 2-methylthioethoxy, 2-ethylthioethoxy and 2-propylthiopropoxy.

Lower alkylthio-lower alkyl has up to 7 C atoms, above all up to 4 C atoms, in the lower alkyl parts and is, for example, methylthiomethyl, ethylthiomethyl, 3-methylthiopropyl, 4-methylthiobutyl and especially 2-methylthioethyl, 2-ethylthioethyl or 2-(n-propylthio)-ethyl.

Lower alkylamino radicals are radicals with, preferably, up to 7 C atoms, especially with up to 4 C atoms, such as, for example, ethylamino, propylamino, i-propylamino, straight or branched butylamino, pentylamino, hexylamino or heptylamino bonded in any desired position, or above all methylamino.

Di-lower alkylamino radicals are radicals with, preferably, up to 7 C atoms, especially with up to 4 C atoms, in each of the lower alkyl parts. The two lower alkyl radicals are independent of one another and form, together with the nitrogen atom, radicals such as, for example, diethylamino, methylethylamino, diethylamino, dipropylamino, dibutylamino or especially dimethylamino.

Lower alkyleneamino radicals are radicals with, for example, 4 to 8 ring members, wherein the lower alkylene part is branched or especially straight-chain lower alkylene with, in particular, 3–7, above all 4–6, C atoms in the alkylene chain. Examples are pyrrolidino or piperidino. Hydroxy-lower alkyleneamino radicals are radicals with, for example, 4–8 ring members, wherein the hydroxysubstituted lower alkylene part is branched or especially straight-chain lower alkylene, in particular with 3–7, above all 4–6, C atoms in the alkylene chain. Examples are 4-hydroxypiperidino or 3-hydroxypyrrolidino.

Oxa-lower alkyleneamino is branched or especially straight-chain oxa-lower alkyleneamino, especially with 4 or 5 C atoms in the oxa-alkylene chain. Morpholino should in particular be mentioned as an example.

Thia-lower alkyleneamino is branched or especially straight-chain thia-lower alkyleneamino, especially with 4 or 5 C atoms in the thiaalkylene chain. Thiomorpholino and 2,6-dimethylthiomorpholino should particularly be mentioned as examples.

Aza-lower alkyleneamino is branched or especially straight-chain aza-lower alkyleneamino especially with 2–6, above all 4–6, C atoms in the azaalkylene chain. Examples are piperazino, N'-methylpiperazino or N'-(β-hydroxyethyl)-piperazino.

Acylamino is, for example, lower alkanoylamino with up to 7 C atoms and above all with up to 4 C atoms in the lower alkyl part or optionally substituted aroylamino, such as optionally substituted benzoylamino or optionally substituted aryl-lower alkanoylamino or lower alkoxycarbonylamino.

Lower alkanoylamino radicals are, for example n-propionylamino, n-butyrylamino, n-valerylamino, n-hexanoylamino, n-heptanoylamino or above all acetylamino. Optionally substituted benzoylamino radicals are, for example, benzoylamino or lower alkoxybenzoylamino, such as n-propoxybenzoylamino and above all methoxybenzoylamino and ethoxybenzoylamino, or lower alkylbenzoylamino, such as n-propylbenzoylamino, straight or branched butylbenzoylamino, pentylbenzoylamino, hexylbenzoylamino or heptylbenzoylamino bonded in any desired position, and above all methylbenzoylamino and ethylbenzoylamino, or trifluoromethylbenzoylamino or halogenobenzoylamino, such as fluorobenzoylamino, bromobenzoylamino and very particularly chlorobenzoylamino. Optionally substituted aryl-lower alkanoylamino radicals are lower alkanoylamino radicals which carry, for example, optionally substituted phenyl groups in any desired position of the lower alkyl part. The phenyl groups can carry the same substituents as mentioned above for optionally substituted benzoylamino radicals. As examples of optionally substituted aryl-lower alkanoylamino there should above all be mentioned phenylacetylamino, 3-phenyl-n-propionylamino, 4-phenyl-n-butyrylamino, chlorophenylacetylamino and bromophenylacetylamino. Lower alkoxycarbonylamino preferably has up to 7 C atoms and above all up to 4 C atoms in the lower alkyl part of lower alkoxy and is, for example, n-propoxycarbonylamino, n-butoxycarbonylamino, i-propoxycarbonylamino, tert.-butoxycarbonylamino and above all methoxycarbonylamino and ethoxycarbonylamino.

Acylamino-lower alkyl radicals are lower alkyl radicals with, preferably, up to 7 C atoms and above all with up to 4 C atoms which are substituted in any desired position by acylamino radicals. Acylamino is, for example, lower alkanoylamino with up to 7 C atoms and above all with up to 4 C atoms in the lower alkyl part or optionally substituted aroylamino, such as optionally substituted benzoylamino, or optionally substituted aryl-lower alkanoylamino or lower alkoxycarbonylamino.

Lower alkanoylamino radicals are, for example, n-propionylamino, n-butyrylamino, n-valerylamino, n-hexanoylamino, n-heptanoylamino or above all acetylamino. Optionally substituted benzoylamino radicals are, for example, benzoylamino or lower alkoxybenzoylamino, such as n-propoxybenzoylamino and above all methoxybenzoylamino and ethoxybenzoylamino, or lower alkylbenzoylamino, such as n-propylbenzoylamino, straight or branched butylbenzoylamino, pentylbenzoylamino, hexylbenzoylamino or heptylbenzoylamino bonded in any desired position, and above all methylbenzoylamino and ethylbenzoylamino, or trifluoromethylbenzoylamino or halogenobenzoylamino, such as fluorobenzoylamino, bromobenzoylamino and very particularly chlorobenzoylamino. Optionally substituted aryl-lower alkanoylamino radicals are lower alkanoylamino radicals which carry, for example, optionally substituted phenyl groups in any desired position of the lower alkyl part. The phenyl groups can carry the same substituents as mentioned above for optionally substituted benzoylamino radicals. As examples of optionally substituted aryl-lower alkanoylamino there should above all be mentioned phenylacetylamino, 3-phenyl-n-propionylamino, 4-phenyl-n-butyrylamino, chlorophenylacetylamino and bromophenylacetylamino. Lower alkoxycarbonylamino preferably has up to 7 C atoms and above all up to 4 C atoms in the lower alkyl part of lower alkoxy and is, for example, n-propoxycarbonylamino, n-butoxycarbonylamino, i-propoxycarbonylamino, tert.-butoxycarbonylamino and above all methoxycarbonylamino and ethoxycarbonylamino. As examples of acylamino-lower alkyl radicals there should accordingly above all be mentioned acetylaminomethyl, 2-acetylaminoethyl, benzoylaminomethyl, 2-benzoylaminoethyl, methoxybenzoylaminomethyl, 2-methoxybenzoylaminoethyl, ethoxybenzoylaminomethyl, 2-ethoxybenzoylaminoethyl, methylbenzoylaminomethyl, 2-methylbenzoylaminoethyl, ethylbenzoylaminomethyl, 2-ethylbenzoylaminoethyl, chlorobenzoylaminomethyl, 2-chlorobenzoylaminoethyl, phenylacetylaminomethyl, 2-phenylacetylaminoethyl, chlorophenylacetylaminomethyl, 2-chlorophenylacetylaminoethyl, methoxycarbonylaminomethyl, ethoxycarbonylaminomethyl, 2-methoxycarbonylaminoethyl, 2-ethoxycarbonylaminoethyl, 3-acetylaminopropyl and 3-methoxycarbonylaminopropyl.

Acylamino-lower alkenyl preferably carries up to 7 C atoms and above all up to 4 C atoms in the lower alkenyl part while acylamino is, for example, lower alkanoylamino, optionally substituted benzoylamino or optionally substituted phenyl-lower alkanoylamino or lower alkoxycarbonylamino. As examples of acylamino-lower alkenyl there should above all be mentioned 2-acetylaminovinyl, benzoylaminovinyl, phenylacetylaminovinyl, 3-acetylaminoallyl, 3-benzoylaminoallyl, 3-phenylacetylaminoallyl and 3-methoxycarbonylaminoallyl.

Optionally substituted phenylthio is, for example, phenylthio, or phenylthio substituted by halogen, trifluoromethyl, lower alkyl or lower alkoxy, and is accordingly above all phenylthio, chlorophenylthio, bromophenylthio, trifluoromethylphenylthio, methylphenylthio, methoxyphenylthio or ethoxyphenylthio.

Lower alkoxycarbonyl preferably has up to 7 C atoms and above all up to 4 C atoms in the lower alkyl part and is above all methoxycarbonyl and ethoxycarbonyl.

Amino-lower alkyl preferably has up to 7 C atoms and above all up to 4 C atoms in the lower alkyl part and is above all aminomethyl, 2-aminoethyl and 3-aminopropyl.

Halogen is fluorine, bromine and very particularly chlorine.

Lower alkylsulphonyl radicals are radicals with, preferably, up to 7 C atoms, especially up to 4 C atoms, such as, for example, ethylsulphonyl, propylsulphonyl, isopropylsulphonyl, straight or branched butylsulphonyl, pentylsulphonyl, hexylsulphonyl or heptylsulphonyl bonded in any desired position, or especially methylsulphonyl.

Optionally substituted carbamoyl is, for example, carbamoyl, N-lower alkylaminocarbonyl with preferably up to 7 C atoms in the lower alkyl part, above all with up to 4 C atoms, N,N-di-lower alkylaminocarbonyl with preferably up to 7 C atoms in each of the lower alkyl parts, above all with up to 4 C atoms in each of the lower alkyl parts, lower alkyleneaminocarbonyl with, preferably, 4 to 8 ring members, above all with 3–7 ring members, hydroxy-lower alkyleneaminocarbonyl with, preferably, 4–8 ring members, above all with 3–7 ring members, oxa-lower alkyleneaminocarbonyl with, preferably, 4 or 5 C atoms in the oxaalkylene chain, thia-lower alkyleneaminocarbonyl with, preferably, 4 or 5 C atoms in the thiaalkylene chain and aza-lower alkyleneaminocarbonyl with 4 or 5 C atoms in the azaalkylene chain. Optionally substituted carbamoyl is accordingly above all carbamoyl, methylaminocarbonyl, ethylaminocarbonyl, n-propylaminocarbonyl, n-butylaminocarbonyl, tert.-butylaminocarbonyl, N,N-dimethylaminocarbonyl, N,N-diethylaminocarbonyl, N,N-(di-n-propylamino)-carbonyl, pyrrolidinocarbonyl, piperidinocarbonyl, 4-hydroxypiperidinocarbonyl, morpholinocarbonyl, thiomorpholinocarbonyl, 2,6-dimethylthiomorpholinocarbonyl, piperazinocarbonyl, N'-methylpiperazinocarbonyl or N'-(β-hydroxyethyl)-piperazinocarbonyl.

For compounds of the formula I wherein Het is optionally substituted pyridazinyl, formula I represents, for example, compounds of the general formula Ib

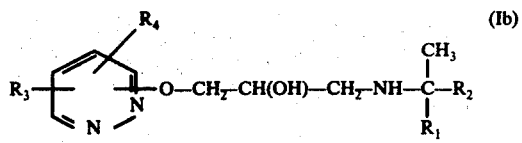

and their condensation products with aldehydes, ketones or carbonic acid and the corresponding N-oxides, wherein $R_1$, $R_2$, $R_3$ and $R_4$ have the same meanings as above.

For compounds of the formula I wherein Het is optionally substituted pyrimidinyl, formula I represents, for example, compounds of the general formula Ic

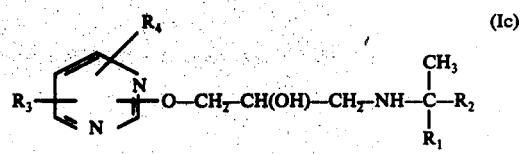

and their condensation products with aldehydes, ketones or carbonic acid and the corresponding N-oxides wherein $R_1$, $R_2$, $R_3$ and $R_4$ have the same meanings as above.

For compounds of the formula I, wherein Het is substituted pyridyl, formula I represents, for example, compounds of the general formula Id

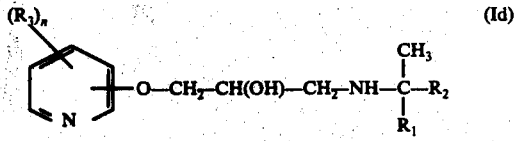

and their condensation products with aldehydes, ketones or carbonic acid and the corresponding N-oxides, wherein $R_1$ and $R_2$ have the above meanings, $R_3$ is halogen, nitrile, nitro, lower alkyl, hydroxy-lower alkyl, lower alkenyl, optionally substituted phenyl, hydroxyl, lower alkoxy, lower alkoxy, lower alkyl, lower alkoxy-lower alkenyl, lower alkoxy-lower alkoxy, lower alkylthio-lower alkoxy, lower alkenyloxy, lower alkylthio, lower alkylthio-lower alkyl, lower alkyleneamino, hydroxy-lower alkyleneamino, oxa-lower alkyleneamino, thia-lower alkyleneamino, aza-lower alkyleneamino, lower alkylamino, di-lower alkylamino, acylamino, acylamino-lower alkyl, acylamino-lower alkenyl, aminolower alkyl, optionally substituted carbamoyl, optionally substituted carbamoyl-lower alkyl or lower alkylsulphonyl and n is 1, 2 or 3, and the substituents $R_3$ can also be different from one another if n is 2 or 3.

In the preceding and following text, a lower radical is especially understood as a radical with up to 7 C atoms, above all with up to 4 C atoms.

Lower alkyl radicals preferably have up to 7 C atoms, above all up to 4 C atoms, and are, for example, methyl, ethyl, n-propyl, i-propyl or butyl, pentyl, hexyl or heptyl which are unbranched or bonded or branched in any desired position.

Hydroxy-lower alkyl preferably has up to 7 C atoms in the lower alkyl part, above all up to 4 C atoms, and is for example, 3-hydroxy-propyl, 2-hydroxy-propyl, 1-methyl2-hydroxy-ethyl or hydroxybutyl, hydroxypentyl, hydroxyhexyl or hydroxyheptyl which are unbranched or bonded or branched in any desired position, and above all hydroxymethyl and 2-hydroxyethyl.

Lower alkenyl preferably has up to 7 C atoms and above all up to 4 C atoms, such as vinyl, 2-methylvinyl, methallyl and especially allyl.

Suitable substituents for optionally substituted phenyl are halogen, trifluoromethyl, lower alkyl, lower alkenyl, lower alkoxymethyl, lower alkoxy and lower alkenyloxy. Optionally substituted phenyl is thus above all phenyl, chlorophenyl, bromophenyl, trifluoromethylphenyl, tolyl, methoxymethylphenyl, methoxyphenyl, ethoxyphenyl and allyloxyphenyl.

Lower alkoxy radicals preferably have up to 7 C atoms, above all up to 4 C atoms, such as, for example, ethoxy, propoxy, i-propoxy, straight or branched butyloxy, pentyloxy, hexyloxy or heptyloxy bonded in any desired position, or, above all, methoxy.

Lower alkoxy-lower alkyl preferably has up to 7 C atoms, above all up to 4 C atoms, in the lower alkyl part of the lower alkoxy part, such lower alkyl parts being iso- or n-propyl, straight or branched butyl, pentyl, hexyl or heptyl bonded in any desired position, especially ethyl and above all methyl. The lower alkyl part which carries the lower alkoxy part preferably has up to 7 C atoms, above all up to 4 C atoms. For example, lower alkoxy-lower alkyl is methoxymethyl, ethoxymethyl, 3-methoxy-n-propyl, 3-ethoxy-n-propyl, 4-methoxy-n-butyl or above all 2-methoxyethyl and 2-ethoxyethyl.

Lower alkoxy-lower alkenyl are lower alkenyl radicals with, preferably, up to 7 C atoms and above all up to 4 C atoms, which are substituted by lower alkoxy in any desired position. Lower alkoxy preferably has up to 7 C atoms and above all up to 4 C atoms in the lower alkyl part. Lower alkoxy-lower alkenyl is thus preferably 2-methoxyvinyl, 2-ethoxyvinyl and above all 3-methoxyallyl and 3-ethoxyallyl.

Lower alkenyloxy radicals are radicals with, preferably, up to 7 C atoms, especially with 3 or 4 C atoms, such as the methallyloxy or above all the allyloxy radical.

Lower alkoxy-lower alkoxy has up to 7 C atoms, above all up to 4 C atoms, in each lower alkyl part and is, for example, methoxymethoxy, ethoxymethoxy, 2-methoxyethoxy, 4-methoxy-n-butoxy and especially 3-methoxy-n-propoxy.

Lower alkylthio-lower alkoxy has up to 7 C atoms, above all up to 4 C atoms, in each of the lower alkyl parts and is, for example, methylthiomethoxy, ethylthiomethoxy, 3-methylthiopropoxy, 4-methylthiobutoxy and especially 2-methylthioethoxy, 2-ethylthioethoxy or 2-(n-propylthio)-ethoxy.

Lower alkylthio radicals preferably have up to 7 C atoms, above all up to 4 C atoms, such as, for example, ethylthio, n-propylthio, n-butylthio, i-propylthio or especially methylthio.

Lower alkylthio-lower alkyl has up to 7 C atoms, above all up to 4 C atoms, in each lower alkyl part and is, for example, methylthiomethyl, ethylthiomethyl, 3-methylthiopropyl, 4-methylthiobutyl and especially 2-methylthioethyl, 2-ethylthioethyl or 2-(n-propylthio)-ethyl. Lower alkylamino radicals are radicals with, preferably, up to 7 C atoms, especially with up to 4 C atoms, such as, for example, ethylamino, propylamino, i-propylamino, straight or branched butylamino, pentylamino, hexylamino or heptylamino bonded in any desired position, or above all methylamino.

Di-lower alkylamino radicals are radicals with, preferably, up to 7 C atoms, especially with up to 4 C atoms, in each of the lower alkyl parts. The two lower alkyl radicals are independent of one another and form, together with the nitrogen atom, radicals such as, for example, diethylamino, methylethylamino, dipropylamino, dibutylamino or especially dimethylamino.

Lower alkyleneamino radicals are radicals with, for example, 4 to 8 ring members, wherein the lower alkylene part is branched or especially straight-chain lower alkylene with, in particular, 3–7, above all 4–6, C atoms in the alkylene chain. Examples are pyrrolidino or piperidino.

Hydroxy-lower alkyleneamino radicals are radicals with, for example, 4–8 ring members, wherein the hydroxysubstituted lower alkylene part is branched or especially straight-chain lower alkylene, in particular with 3–7, above all 4–6, C atoms in the alkylene chain. Examples are 4-hydroxypiperidino or 3-hydroxypyrrolidino.

Oxa-lower alkyleneamino is branched or especially straight-chain oxa-lower alkyleneamino, especially with 4 or 5 C atoms in the oxa-alkylene chain. Morpholino should in particular be mentioned as an example.

Thia-lower alkyleneamino is branched or especially straight-chain thia-lower alkyleneamino, especially with 4 or 5 C atoms in the thiaalkylene chain. Thiomorpholino and 2,6-dimethylthiomorpholino should particularly be mentioned as examples.

Aza-lower alkyleneamino is branched or especially straight-chain aza-lower alkyleneamino in particular with 2–6, above all 4–6, C atoms in the azaalkylene chain. Examples are piperazino, N'-methylpiperazino or N'-($\beta$-hydroxyethyl)-piperazino.

Acylamino is, for example, lower alkanoylamino with up to 7 C atoms, and above all with up to 4 C atoms in the lower alkyl part or optionally substituted aroylamino, such as optionally substituted benzoylamino or optionally substituted aryl-lower alkanoylamino or lower alkoxycarbonylamino.

Lower alkanoylamino radicals are, for example, n-propionylamino, n-butyrylamino, n-valerylamino, n-hexanoylamino, n-heptanoylamino or above all acetylamino. Optionally substituted benzoylamino radicals are, for example, benzoylamino or lower alkoxybenzoylamino, such as n-propoxybenzoylamino and above all methoxybenzoylamino and ethoxybenzoylamino, or lower alkylbenzoylamino, such as n-propylbenzoylamino, straight or branched butylbenzoylamino, pentylbenzoylamino, hexylbenzoylamino or heptylbenzoylamino bonded in any desired position, and above all methylbenzoylamino and ethylbenzoylamino, or trifluoromethylbenzoylamino or halogenobenzoylamino, such as fluorobenzoylamino, bromobenzoylamino and very particularly chlorobenzoylamino. Optionally substituted aryl-lower alkanoylamino radicals are lower alkanoylamino radicals which carry, for example, optionally substituted phenyl groups in any desired position of the lower alkyl part. The phenyl groups can carry the same substituents as mentioned above for optionally substituted benzoylamino radicals. As examples of optionally substituted aryl-lower alkanoylamino there should above all be mentioned phenylacetylamino, 3-phenyl-n-propionylamino, 4-phenyl-n-butyrylamino, chlorophenylacetylamino and bromophenylacetylamino. Lower alkoxycarbonylamino preferably has up to 7 C atoms and above all up to 4 C atoms in the lower alkyl part of lower alkoxy and is, for example, n-propoxycarbonylamino, n-butoxycarbonylamino, i-propoxycarbonylamino, tert.-butoxycarbonylamino and above all methoxycarbonylamino and ethoxycarbonylamino.

Acylamino-lower alkyl radicals are lower alkyl radicals with, preferably, up to 7 C atoms and above all with up to 4 C atoms which are substituted in any desired position by acylamino radicals. Acylamino is, for example, lower alkanoylamino with up to 7 C atoms and above all with up to 4 C atoms in the lower alkyl part or optionally substituted aroylamino, such as optionally substituted benzoylamino, or optionally substituted aryl-lower alkanoylamino or lower alkoxycarbonylamino.

Lower alkanoylamino radicals are, for example, n-propionylamino, n-butyrylamino, n-valerylamino, n-hexanoylamino, n-heptanoylamino or above all acetylamino. Optionally substituted benzoylamino radicals are, for example, benzoylamino or lower alkoxybenzoylamino, such as n-propoxybenzoylamino and above all methoxybenzoylamino and ethoxybenzoylamino, or lower alkylbenzoylamino, such as n-propylbenzoylamino, straight or branched butylbenzoylamino, pentylbenzoylamino, hexylbenzoylamino or heptylbenzoylamino bonded in any desired position, and above all methylbenzoylamino and ethylbenzoylamino, or trifluoromethylbenzoylamino or halogenobenzoylamino, such as fluorobenzoylamino, bromobenzoylamino and very particularly chlorobenzoylamino. Optionally substituted aryl-lower alkanoylamino radicals are lower alkanoylamino radicals which carry, for example, optionally substituted phenyl groups in any desired position of the lower alkyl part. The phenyl groups can carry the same substituents as mentioned above for optionally substituted benzoylamino radicals. As examples of optionally substituted aryl-lower alkanoylamino there should above all be mentioned phenylacetylamino, 3-phenyl-n-propionylamino, 4-phenyl-n-butyrylamino, chlorophenylacetylamino and bromophenylacetylamino. Lower alkoxycarbonylamino preferably has up to 7 C atoms and above all up to 4 C atoms in the lower alkyl part of lower alkoxy and is, for example, n-propoxycarbonylamino, n-butoxycarbonylamino, i-propoxycarbonylamino, tert.-butoxycarbonylamino and above all methoxycarbonylamino and ethoxycarbonylamino. As examples of acylamino-lower alkyl radicals there should accordingly above all be mentioned acetylaminomethyl, 2-acetylaminoethyl, benzoylaminomethyl, 2-benzoylaminoethyl, methoxybenzoylaminomethyl, 2-methoxybenzoylaminoethyl, ethoxybenzoylaminomethyl, 2-ethoxybenzoylaminoethyl, methylbenzoylaminomethyl, 2-methylbenzoylaminoethyl, ethylbenzoylaminomethyl, 2-ethylbenzoylaminoethyl, chlorobenzoylaminomethyl, 2-chlorobenzoylaminoethyl, phenylacetylaminomethyl, 2-phenylacetylaminoethyl, 3-acetylaminopropyl, 3-methoxycarbonylaminopropyl, methoxycarbonylaminomethyl, ethoxycarbonylaminomethyl, 2-methoxycarbonylaminoethyl and 2-ethoxycarbonylaminoethyl.

Acylamino-lower alkenyl preferably carries up to 7 C atoms and above all up to 4 C atoms in the lower alkenyl part while acylamino is, for example, lower alkanoylamino, optionally substituted benzoylamino or optionally substituted phenyl-lower alkanoylamino or lower alkoxycarbonylamino. As examples of acylamino-lower alkenyl there should above all be mentioned 2-acetylaminovinyl, benzoylaminovinyl, phenylacetylaminovinyl, 3-acetylaminoallyl, 3-benzoylaminoallyl, 3-phenylacetylaminoallyl and 3-methoxycarbonylaminoallyl.

Amino-lower alkyl preferably has up to 7 C atoms and above all up to 4 C atoms in the lower alkyl part and is above all aminomethyl, 2-aminoethyl and 3-aminopropyl.

Optionally substituted carbamoyl is, for example, carbamoyl, N-lower alkylaminocarbonyl with preferably up to 7 C atoms in the lower alkyl part, above all with up to 4 C atoms, N,N-di-lower alkylaminocarbonyl with, preferably, up to 7 C atoms in each of the lower alkyl parts, above all with up to 4 C atoms in each of the lower alkyl parts, lower alkyleneaminocarbonyl with, preferably, 4 to 8 ring members, above all with 3-7 ring members, hydroxy-lower alkyleneaminocarbonyl with, preferably, 4-8 ring members, above all with 3-7 ring members, oxa-lower alkyleneaminocarbonyl with, preferably, 4 or 5 C atoms in the oxaalkylene chain, thia-lower alkyleneaminocarbonyl with, preferably, 4 or 5 C atoms in the thiaalkylene chain and aza-lower alkyleneaminocarbonyl with 4 or 5 C atoms in the azaalkylene chain. Optionally substituted carbamoyl is, accordingly, above all carbamoyl, methylaminocarbonyl, ethylaminocarbonyl, n-propylaminocarbonyl, n-butylaminocarbonyl, tert.-butylaminocarbonyl, N,N-dimethylaminocarbonyl, N,N-diethylaminocarbonyl, N,N-(di-n-propylamino)-carbonyl, pyrrolidinocarbonyl, piperidinocarbonyl, 4-hydroxypiperidinocarbonyl, morpholinocarbonyl, thiomorpholinocarbonyl, 2,6-dimethylthiomorpholinocarbonyl, piperazinocarbonyl, N'-methylpiperazinocarbonyl or N'-(β-hydroxyethyl)-piperazinocarbonyl.

Optionally substituted carbamoyl-lower alkyl preferably has up to 7 C atoms and above all up to 4 C atoms whilst the carbamoyl part it contains is that indicated above for optionally substituted carbamoyl, and is, for example, carbamoylmethyl, 2-carbamoylethyl, methylaminocarbonylmethyl, 2-methylaminocarbonylethyl, dimethylaminocarbonylmethyl, 2-dimethylaminocarbonylethyl, piperazinocarbonylmethyl, 2-piperazinocarbonylethyl, N'-methylpiperazinocarbonylmethyl or 2-[N'-methyl-piperazinocarbonyl]ethyl.

Lower alkylsulphonyl radicals are radicals with, preferably, up to 7 C atoms, especially with up to 4 C atoms, such as, for example, ethylsulphonyl, propylsulphonyl, iso-propylsulphonyl, straight or branched butylsulphonyl, pentylsulphonyl, hexylsulphonyl or heptylsulphonyl bonded in any desired position, or especially methylsulphonyl.

Halogen is fluorine, bromine and very particularly chlorine.

Amongst the compounds of the type Ia, pyrazines of the formula Iaa

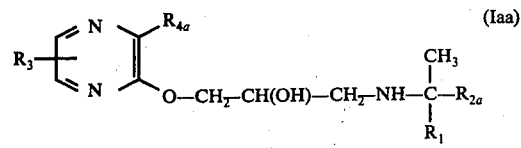

(Iaa)

and their condensation products with aldehydes, ketones or carbonic acid and their corresponding pyrazine-N-oxides should be singled out; in this formula, $R_1$ and $R_3$ have the above meaning, $R_{2a}$ denotes lower alkyl with up to 4 C atoms, benzyl, halogenobenzyl, trifluoromethylbenzyl, lower alkylbenzyl with up to 7 C atoms in the lower alkyl part, lower alkoxybenzyl with up to 7 C atoms in the lower alkyl part, carboxy-lower alkyl with up to 4 C atoms in the lower alkyl part, lower alkoxycarbonyl-lower alkyl with 4 C atoms in each of the lower alkyl parts, carbamoyl-lower alkyl with up to 4 C atoms in the lower alkyl part, lower alkylaminocarbonyl-lower alkyl with up to 4 C atoms in each of the lower alkyl parts, di-lower alkylaminocarbonyl-lower alkyl with up to 4 C atoms in each of the lower alkyl parts, pyrrolidinocarbonyl-lower alkyl, piperazinocarbonyl-lower alkyl, N'-methylpiperazinocarbonyl-lower alkyl, N'-(β-hydroxyethyl)-piperazinocarbonyl-lower alkyl, morpholinocarbonyl-lower alkyl, thiomorpholinocarbonyl-lower alkyl, and 2,6-dimethylthiomorpholinocarbonyl-lower alkyl with up to 7 C atoms in the lower alkyl part or cyano-lower alkyl with up to 4 C atoms in the lower alkyl part, and $R_{4a}$ denotes hydrogen, hydroxyl, lower alkyl with up to 7 C atoms, lower alkenyl with up to 7 C atoms, halogen, lower alkylamino with up to 7 C atoms, di-lower alkylamino with up to 7 C atoms in each of the lower alkyl parts, pyrrolidino, piperidino, 4-hydroxypiperidino, morpholino, thiomorpholino, 2,6-dimethylthiomorpholino, lower alkoxy with up to 7 C atoms, lower alkenyloxy with up to 7 C atoms, lower alkoxy-lower alkyl with up to 4 C atoms in each of the lower alkyl parts, lower alkoxy-lower alkoxy with up to 4 C atoms in each of the lower alkyl parts, lower alkylthio with up to 7 C atoms, lower alkylthio-lower alkoxy with up to 7 C atoms in each of the lower alkyl parts, lower alkanoylamino with up to 7 C atoms in the lower alkyl part or lower alkoxycarbonylamino with up to 7 C atoms in the lower alkyl part.

Further compounds to be singled out are those of the formula Iab

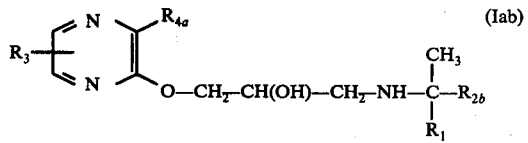

and their condensation products with aldehydes, ketones or carbonic acid, wherein $R_1$, $R_3$ and $R_{4a}$ have the above meanings, and $R_{2b}$ denotes lower alkyl with up to 4 C atoms, benzyl, carbamoylmethyl, lower alkylaminocarbonylmethyl with up to 7 C atoms in the lower alkyl part, di-lower alkylaminocarbonylmethyl with up to 7 C atoms in each of the lower alkyl parts, pyrrolidinocarbonylemthyl, piperidinocarbonylmethyl, piperazinocarbonylmethyl, N'-methylipiperazinocarbonylmethyl, N'-(β-hydroxyethyl)-piperazinocarbonylmethyl, morpholinocarbonylmethyl, thiomorpholinocarbonylmethyl, 2,6-dimethylthiomorpholinocarbonylmethyl or cyanomethyl.

Further compounds to be singled out are those of the formula Iac

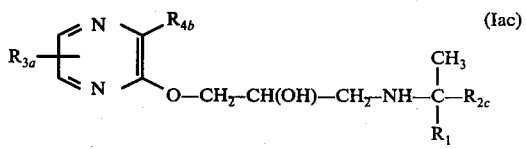

and their condensation products with aldehydes, ketones or carbonic acid, wherein $R_1$ has the above meaning, $R_{2c}$ denotes lower alkyl with up to 4 C atoms, benzyl, carbamoylmethyl or cyanomethyl. $R_{3a}$ denotes hydrogen, halogen, nitrile, lower alkyl with up to 7 C atoms, lower alkoxy-lower alkyl with up to 7 C atoms in each of the lower alkyl parts, lower alkoxy-lower alkenyl with up to 4 C atoms in the lower alkyl part and with up to 4 C atoms in the lower alkenyl part, lower alkanoylamino with up to 7 C atoms in the lower alkyl part, lower alkoxycarbonylamino with up to 7 C atoms in the lower alkyl part, lower alkanoylamino-lower alkyl with up to 4 C atoms in each of the lower alkyl parts, lower alkoxycarbonylamino-lower alkyl with up to 4 C atoms in each of the lower alkyl parts, lower alkanoylamino-lower alkenyl with up to 4 C atoms in the lower alkyl part and with up to 4 C atoms in the lower alkenyl part, lower alkoxycarbonylamino-lower alkenyl with up to 4 C atoms in the lower alkyl part and with up to 4 C atoms in the lower alkenyl part and $R_{4b}$ denotes hydrogen, hydroxyl, lower alkyl with up to 4 C atoms, lower alkenyl with 3 or 4 C atoms, lower alkylamino with up to 4 C atoms, di-lower alkylamino with up to 4 C atoms in each of the lower alkyl parts, pyrrolidino, piperidino, 4-hydroxypiperidino, morpholino, thiomorpholino, 2,6-dimethylthiomorpholino, piperazino, N'-methylpiperazino, chlorine, bromine, lower alkoxy with up to 4 C atoms, lower alkenyloxy with 3 or 4 C atoms in the lower alkenyl part, lower alkoxy-lower alkyl with up to 4 C atoms in each of the lower alkyl parts, lower alkoxy-lower alkoxy with up to 4 C atoms in each of the lower alkyl parts, lower alkylthio with up to 4 C atoms, lower alkylthio-lower alkoxy with up to 4 C atoms in each of the lower alkyl parts, lower alkanoylamino with up to 4 C atoms or lower alkoxycarbonylamino with up to 4 C atoms in the lower alkyl part.

Further compounds to be singled out are pyrazines of the formula Iad

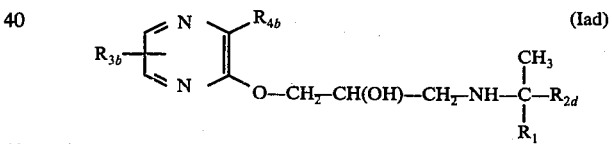

wherein $R_1$ and $R_{4b}$ have the above meanings, $R_{2d}$ denotes methyl, $R_{3b}$ denotes hydrogen, bromine, chlorine, lower alkyl with up to 4 C atoms, lower alkoxy-lower alkyl with up to 4 C atoms in each of the lower alkyl parts, lower alkoxy-lower alkenyl with up to 4 C atoms in the lower alkyl part and with up to 4 C atoms in the lower alkenyl part, lower alkanoylamino with up to 4 C atoms in the lower alkyl part, lower alkoxycarbonylamino with up to 4 C atoms in the lower alkyl part, lower alkanoylamino-lower alkyl with up to 4 C atoms in each of the lower alkyl parts and lower alkoxycarbonylamino-lower alkyl with up to 4 C atoms in each of the lower alkyl parts.

Further compounds to be singled out are pyrazines of the formula Iae

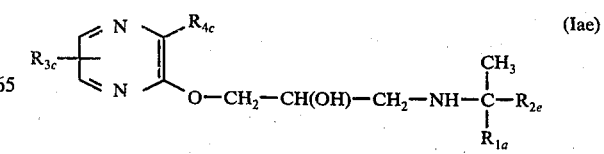

wherein $R_{1a}$ is hydrogen or methyl, $R_{2e}$ is lower alkyl with 1–4 C atoms or phenyl-lower alkyl with up to 4 C atoms in the lower alkyl part, $R_{3c}$ is hydrogen, halogen, lower alkyl with 1–4 C atoms, 2-$(C_{1-4})$-lower alkoxyethyl or 2-$(C_{1-4})$-lower alkoxycarbonylaminoethyl and $R_{4c}$ is hydrogen, halogen, lower alkoxy with 1–4 C atoms, lower alkoxy-lower alkoxy with up to 4 C atoms in each of the lower alkyl parts, lower alkenyloxy with up to 4 C atoms, lower alkylthio with up to 4 C atoms, lower alkyleneamino with 4–6 C atoms in the lower alkylene chain, hydroxy-lower alkyleneamino with 4–6 C atoms in the alkylene chain, oxalower alkyleneamino with 4–5 C atoms in the oxa-lower alkylene chain, lower alkylamino with up to 4 C atoms, di-lower alkylamino with up to 4 C atoms in each of the lower alkyl parts, phenylthio or N'-lower alkylaza-lower alkyleneamino with 4–6 C atoms in the lower alkyl parts, and in particular $R_{1a}$ is hydrogen or methyl, $R_{2e}$ is methyl or 2-phenylethyl, $R_{3c}$ is hydrogen, bromine, methyl, 2-methoxyethyl or 2-methoxycarbonylaminoethyl and $R_{4c}$ is hydrogen, chlorine, methoxy, 2-methoxyethoxy, allyloxy, ethylthio, morpholino, 4-hydroxypiperidino, dimethylamino, isopropylamino, phenylthio or N'-methylpiperazino, and especially the compounds mentioned in the examples.

In all the abovementioned groups the substituent $R_3$, $R_{3a}$, $R_{3b}$ and $R_{3c}$ is preferably in the para-position to the 3-amino-2-hydroxy-propoxy group but can also be in the meta-position.

Amongst the compounds of type $I_b$, pyridazines of the formula $I_{ba}$

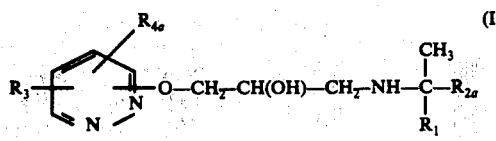

and their condensation products with aldehydes, ketones or carbonic acid and their corresponding pyridazine-N-oxides, wherein $R_1$, $R_{2a}$, $R_3$ and $R_{4a}$ have the above meanings, should be singled out.

Pyridazines of the formula $I_{bb}$

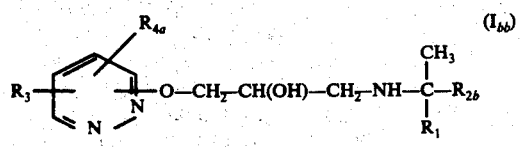

and their condensation products with aldehydes, ketones or carbonic acid, wherein $R_1$, $R_{2b}$, $R_3$ and $R_{4a}$ have the above meanings, should also be singled out.

Pyridazines of the formula $I_{bc}$

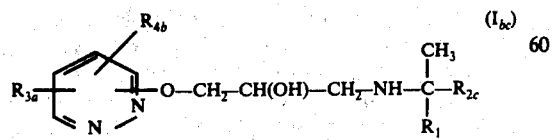

wherein $R_1$, $R_{2c}$, $R_{3a}$ and $R_{4b}$ have the above meanings, should also be singled out.

Pyridazines of the formula $I_{bd}$

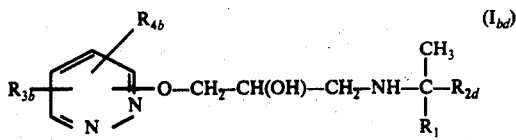

wherein $R_1$, $R_{2b}$, $R_{3b}$ and $R_{4b}$ have the above meanings, should also be singled out.

Further compounds to be singled out are particularly pyridazines of the formula $I_{be}$

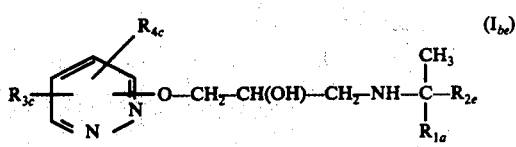

and their condensation products with aldehydes, wherein $R_{1a}$ is hydrogen or methyl, $R_{2e}$ is hydrogen or lower alkyl with up to 4 C atoms, $R_{3c}$ is hydrogen and $R_4$ is hydrogen, lower alkoxy, halogen, oxa-lower alkyleneamino with up to 6 C atoms in the lower alkylene part or hydroxyl and especially $R_{1a}$ is hydrogen, $R_{2e}$ is methyl, $R_{3c}$ is hydrogen and $R_4$ is hydrogen, methoxy, chlorine, morpholino or hydroxyl, and very particularly the compounds mentioned in the examples. Condensation products with aldehydes are preferably those with aryl-lower alkanals such as, for example, benzaldehyde.

In all the abovementioned groups, the substituent $R_3$, $R_{3a}$, $R_{3b}$ or $R_{3c}$ is preferably in the para-position to the 3-amino-2-hydroxy-propoxy group but can also be in the meta-position or ortho-position.

Amongst the compounds of the type $I_c$, pyrimidines of the formula $I_{ca}$

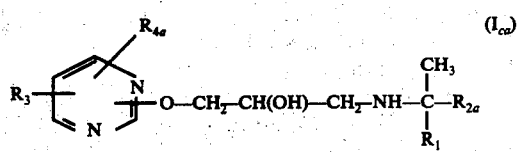

and their condensation products with aldehydes, ketones or carbonic acid and their corresponding pyrimidine-N-oxides, wherein $R_1$, $R_{2a}$, $R_3$ and $R_{4a}$ have the above meanings, should be singled out.

Pyrimidines of the formula $I_{cb}$

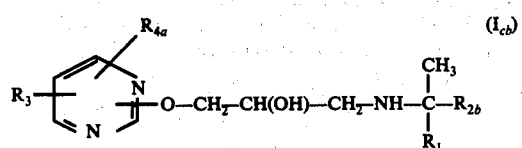

and their condensation products with aldehydes, ketones or carbonic acid, wherein $R_1$, $R_{2b}$, $R_3$ and $R_{4a}$ have the above meanings, should also be singled out.

Pyrimidines of the formula $I_{cc}$

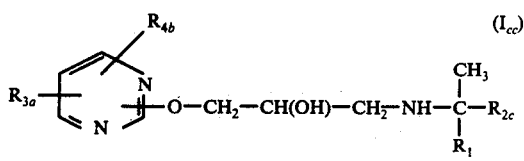

wherein $R_1$, $R_{2c}$, $R_{3a}$ and $R_{4b}$ have the above meanings, should also be singled out.

Pyrimidines of the formula $I_{cd}$

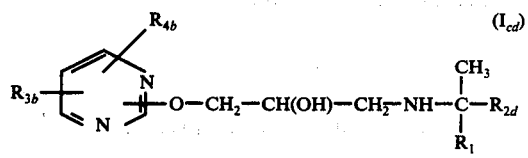

wherein $R_1$, $R_{2d}$, $R_{3b}$ and $R_{4b}$ have the above meanings, should also be singled out.

Further compounds which should be singled out are particularly pyrimidines of the formula $I_{ce}$

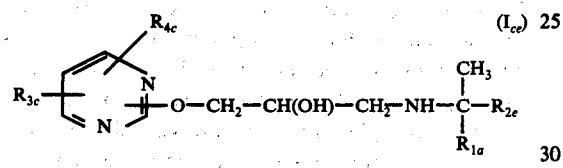

and their condensation products with aldehydes, wherein $R_{1a}$ is hydrogen or methyl, $R_{2e}$ is hydrogen or lower alkyl with up to 4 C atoms in the lower alkyl part, $R_{3c}$ is hydrogen, nitrile, di-lower alkylamino with up to 4 C atoms in each of the lower alkyl parts, lower alkoxycarbonylamino-lower alkyl with up to 4 C atoms in each of the lower alkyl parts or lower alkyl with up to 6 C atoms and $R_{4c}$ is hydrogen, lower alkanoylamino with up to 4 C atoms in the lower alkyl part, lower alkoxy-lower alkyl with up to 4 C atoms in each of the lower alkyl parts, phenyl, lower alkylthio-lower alkyl with up to 4 C atoms in each of the lower alkyl parts, lower alkylaminocarbonyl with up to 7 C atoms in the lower alkyl part or lower alkoxycarbonyl with up to 3 C atoms in the lower alkyl part, and in particular $R_{1a}$ is hydrogen, $R_{2e}$ is methyl, $R_{3c}$ is hydrogen, nitrile, dimethylamino, 2-methoxycarbonylaminoethyl, methyl or ethyl and $R_{4c}$ is hydrogen, acetylamino, 2-methoxyethyl, phenyl, methylthiomethyl, n-hexylaminocarbonyl or ethoxycarbonyl, and very particularly the compounds mentioned in the examples. Condensation products with aldehydes are preferably those with aryl-lower alkanals, such as, for example, benzaldehyde.

In all the abovementioned groups, the substituent $R_3$, $R_{3a}$, $R_{3b}$ or $R_{3c}$ is preferably in the para-position to the 3-amino-2-hydroxy-propoxy group but can also be in the meta-position or ortho-position.

Amongst the compounds of type $I_d$, there should be singled out pyridines of the formula $I_{da}$

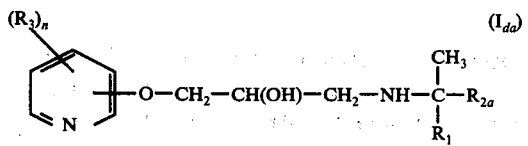

and their condensation products with aldehydes, ketones and carbonic acid and their corresponding pyridine-N-oxides, wherein $R_1$, $R_3$ and n have the above meaning and $R_{2a}$ denotes lower alkyl with up to 4 C atoms, benzyl, halogenobenzyl, trifluoromethylbenzyl, lower alkylbenzyl with up to 7 C atoms in the lower alkyl part, lower alkoxybenzyl with up to 7 C atoms in the lower alkyl part, carboxy-lower alkyl with up to 4 C atoms in the lower alkyl part, lower alkoxycarbonyl-lower alkyl with up to 4 C atoms in each of the lower alkyl parts, carbamoyl-lower alkyl with up to 4 C atoms in the lower alkyl part, lower alkylaminocarbonyl-lower alkyl with up to 4 C atoms in each of the lower alkyl parts, di-lower alkylaminocarbonyl-lower alkyl with up to 4 C atoms in each of the lower alkyl parts, N'-methylpiperazinocarbonyl-lower alkyl, N'(β-hydroxyethyl)-piperazino-carbonyl-lower alkyl, morpholinocarbonyl-lower alkyl, thiomorpholinocarbonyl-lower alkyl, 2,6-dimethylthiomorpholinocarbonyl-lower alkyl with up to 7 C atoms in the lower alkyl part or cyano-lower alkyl with up to 4 C atoms in the lower alkyl part.

Further compounds to be singled out are those of the formula $I_{db}$

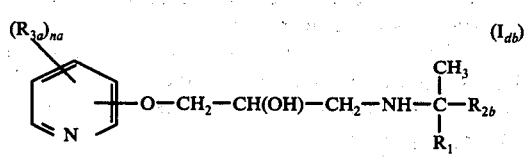

wherein $R_1$ has the above meaning and $n_a$ is 1 or 2, $R_{3a}$ denotes halogen, nitrile, nitro, lower alkyl with up to 4 C atoms, lower alkenyl with up to 4 C atoms, phenyl, halogenophenyl, trifluoromethylphenyl, lower alkylphenyl with up to 7 C atoms in the lower alkyl part, lower alkoxyphenyl with up to 4 C atoms in the lower alkyl part, hydroxy-lower alkyl with up to 7 C atoms in the lower alkyl part, lower alkoxy with up to 7 C atoms in the lower alkyl part, hydroxyl, lower alkoxy-lower alkenyl with up to 4 C atoms in the lower alkyl part and with up to 4 C atoms in the lower alkenyl part, lower alkoxy-lower alkyl with up to 4 C atoms in each of the lower alkyl parts, lower alkoxy-lower alkoxy with up to 4 C atoms in each of the lower alkyl parts, lower alkenyloxy with up to 4 C atoms in the lower alkenyl part, lower alkylthio-lower alkoxy with up to 7 C atoms in each of the lower alkyl parts, lower alkylthio with up to 7 C atoms in the lower alkyl part, lower alkylthio-lower alkyl with up to 7 C atoms in each of the lower alkyl parts, lower alkanoylamino with up to 7 C atoms in the lower alkyl part, lower alkoxycarbonylamino with up to 7 C atoms in the lower alkyl part, lower alkanoylamino-lower alkyl with up to 4 C atoms in each of the lower alkyl parts, lower alkoxycarbonylamino-lower alkyl with up to 4 C atoms in the lower alkyl parts, lower alkylamino with up to 7 C atoms in the lower alkyl part, di-lower alkylamino with up to 7 C atoms in each of the lower alkyl parts, pyrrolidino, piperidino, 4-hydroxypiperidino, morpholino, thiomorpholino or 2,6-dimethylthiomorpholino or optionally substituted carbamoyl, $R_{2b}$ denotes lower alkyl with up to 4 C atoms, benzyl, carbamoylmethyl, lower alkylaminocarbonylmethyl with up to 7 C atoms in the lower alkyl part, di-lower alkylaminocarbonylmethyl with up to 7 C atoms in each of the lower alkyl parts, pyrrolidinocarbonylmethyl, piperidinocarbonylmethyl, piperazinocarbonylmethyl, N'-methylpiperazinocarbonylmethyl, N'-(β-hydroxyethyl)-piperazinocarbonylmethyl, morpholinocarbonylmethyl, thiomorpholinocarbonylmethyl, 2,6-dimethylthiomorpholinocarbonylmethyl or cyanomethyl.

Further compounds to be singled out are pyridines of the formula $I_{dc}$

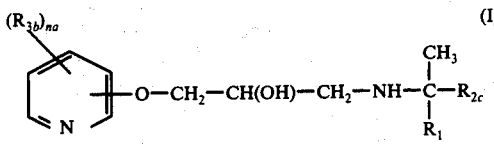

wherein $R_1$ and $n_a$ have the above meanings, $R_{3b}$ denotes chlorine, bromine, nitrile, nitro, hydroxyl, lower alkyl with up to 4 C atoms, lower alkenyl with 3 or 4 C atoms, phenyl, chlorophenyl, bromophenyl, trifluoromethylphenyl, lower alkylphenyl with up to 4 C atoms in the lower alkyl part, lower alkoxyphenyl with up to 4 C atoms in the lower alkyl part, hydroxy-lower alkyl with up to 4 C atoms, lower alkoxy with up to 4 C atoms, lower alkoxyalkenyl with up to 4 C atoms in the lower alkyl part and 3 or 4 C atoms in the lower alkenyl part, lower alkoxy-lower alkyl with up to 4 C atoms in each of the lower alkyl parts, lower alkoxy-lower alkoxy with up to 4 C atoms in each of the lower alkyl parts, lower alkenyloxy with 3 or 4 C atoms, lower alkylthio with up to 4 C atoms, lower alkanoylamino with up to 4 C atoms in the lower alkyl part, lower alkoxycarbonylamino with up to 4 C atoms in the lower alkyl part, lower alkanoylamino-lower alkyl with up to 4 C atoms in each of the lower alkyl parts, lower alkoxycarbonylaminolower alkyl with up to 4 C atoms in each of the lower alkyl parts, lower alkylamino with up to 4 C atoms in the lower alkyl part, di-lower alkylamino with up to 4 C atoms in each of the lower alkyl parts, pyrrolidino, piperidino, 4-hydroxypiperidino, morpholino, thiomorpholino or 2,6-dimethylthiomorpholino, carbamoyl, lower alkylaminocarbonyl with 1–4 C atoms in the lower alkyl part, di-lower alkylaminocarbonyl with 1–4 C atoms in each of the lower alkyl parts, lower alkyleneaminocarbonyl with 5 C atoms in the alkyleneamino chain, oxa-, thia- or aza-lower alkyleneaminocarbonyl each with 4 C atoms in the rings or carbamoyl-lower alkyl with up to 4 C atoms in the lower alkyl part and $R_{2c}$ denotes lower alkyl with up to 4 C atoms, benzyl, carbamoylmethyl or cyanomethyl.

Further compounds to be singled out are pyridines of the formula $I_{dd}$

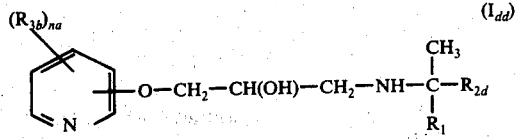

wherein $R_1$, $R_{3b}$ and $n_a$ have the above meanings and $R_{2d}$ denotes methyl.

Further compounds, to be singled out very particularly, are pyridines of the formula $I_{de}$

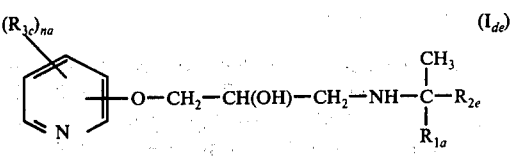

and their corresponding pyridine-N-oxides and their condensation products with aldehydes, wherein $n_a$ is 1, 2 or 3, $R_{1a}$ is hydrogen or methyl, $R_{2e}$ is lower alkyl with up to 4 C atoms or phenyl-lower alkyl with up to 5 C atoms in the lower alkyl part, $R_{3c}$ is halogen, nitro, nitrile, lower alkyl with up to 4 C atoms, lower alkoxy with up to 4 C atoms, optionally substituted phenyl, Di-$(C_{1-4})$-lower alkylamino, $(C_{1-4})$-lower alkylamino, lower alkyoxy-lower alkyl with up to 4 C atoms in each of the lower alkyl parts, lower alkanoylamino with up to 5 C atoms in the lower alkanoyl part, lower alkenyloxy with up to 4 C atoms in the lower alkenyl part, lower alkanoylamino-lower alkyl with up to 5 C atoms in the lower alkanoyl part and with up to 4 C atoms in the lower alkyl part, hydroxyl, hydroxy-lower alkyl with up to 4 C atoms in the lower alkyl part, $(C_{1-4})$-lower alkoxycarbonylamino-lower alkyl with up to 4 C atoms in the lower alkyl part, amino-lower alkyl with up to 4 C atoms in the lower alkyl part, lower alkylaminocarbonyl with up to 6 C atoms in the lower alkyl part, lower alkyleneaminocarbonyl with up to 5 C atoms in the lower alkylene chain or aminocarbonyl-lower alkyl with up to 4 C atoms in the lower alkyl part, and condensation products with aldehydes, preferably condensation products with optionally substituted benzaldehyde, and in particular $n_a$ is 1, 2 or 3, $R_{1a}$ is hydrogen or methyl, $R_{2e}$ is methyl or 2-phenylethyl and $R_{3c}$ is chlorine, nitro, methyl, ethyl, n-propyl, n-butyl, nitrile, methoxy, ethoxy, allyloxy, phenyl, methylamino, dimethylamino, 2-aminoethyl, aminomethyl, 2-methoxyethyl, hydroxyl, hydroxymethyl, ethylamino, acetylamino, acetylaminomethyl, 2-methoxycarbonylaminoethyl, methoxycarbonylaminomethyl, 2-ethoxycarbonylaminoethyl, n-butoxycarbonylaminomethyl, 2-[n-butoxycarbonylamino]-ethyl, methylaminocarbonyl, n-butylaminocarbonyl, n-hexylaminocarbonyl, pyrrolidinocarbonyl or aminocarbonylmethyl, and condensation products with benzaldehyde, and very particularly the compounds mentioned in the examples.

In all the preceding groups, the 3-amino-2-hydoxypropoxy radical can occupy positions 2, 3 or 4 of the pyridine ring but preferably occupies position 3 or very particularly position 2.

In all the abovementioned groups, the substituents $R_3$ can, in the case of $n$ being 2 or 3, be identical or different from one another.

In all the abovementioned groups, one of the substituents $R_3$, $R_{3a}$, $R_{3b}$ or $R_{3c}$ is preferably in the orthoposition or very particularly in the para-position to the 3-amino-2-hydroxy-propoxy radical.

The new compounds are obtained according to methods which are in themselves known.

Thus, a compound of the formula II

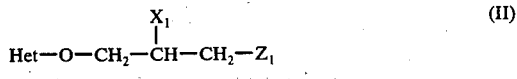

can be reacted with a compound III

Z$_2$—C(CH$_3$)R$_1$R$_2$ (III)

wherein Het, R$_1$ and R$_2$ have the above meanings and one of the radicals Z$_1$ and Z$_2$ is amino and the other is a reactive, esterified hydroxyl group and X$_1$ is hydroxyl, or Z$_1$ together with X$_1$ form an epoxy group if Z$_2$ is amino.

Compounds of type Ia, Ib or Ic can be manufactured, for example, according to the following methods.

It is possible, for example, to react a compound of the formula IIa, or the corresponding pyrazine-N-oxide

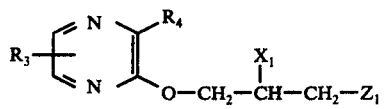
(IIa)

or of the formula IIb, or the corresponding pyridazine-N-oxide

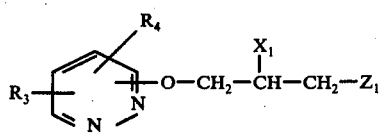
(IIb)

or of the formula IIc, or the corresponding pyrimidine-N-oxide

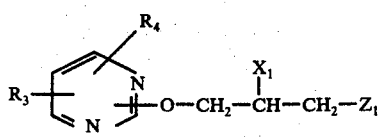
(IIc)

with a compound of the formula III

Z$_2$—C(CH$_3$)R$_1$R$_2$ (III)

wherein R$_1$, R$_2$, R$_3$, R$_4$, Z$_1$ and Z$_2$ have the above meanings.

Thus it is possible to react a compound of the formula IIaa

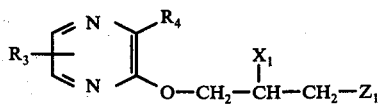
(IIaa)

or of the formula IIba

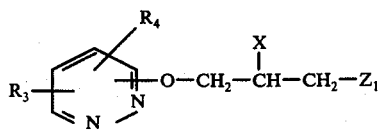
(IIba)

or of the formula IIca

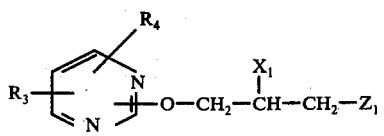
(IIca)

wherein R$_3$ and R$_4$ have the above meanings, X$_1$ represents a hydroxyl group and Z$_1$ represents a reactive esterified hydroxyl group, or X$_1$ and Z$_1$ together form an epoxy group, with an amine of the formula NH$_2$—C(CH$_3$)R$_1$R$_2$, wherein R$_1$ and R$_2$ have the above meanings.

A reactive, esterified hydroxyl group is, in particular, a hydroxyl group esterified with a strong inorganic or organic acid, above all a hydrogen halide acid, such as hydrochloric acid, hydrobromic acid or hydriodic acid, or sulphuric acid or a strong organic sulphonic acid such as, for example, benzenesulphonic acid, 4-bromobenzenesulphonic acid, 4-toluenesulphonic acid or methanesulphonic acid. Thus Z in particular represents chlorine, bromine or iodine.

This reaction is carried out in the usual manner. If a reactive ester is used as the starting material, the reaction is preferably carried out in the presence of a basic condensation agent and/or using an excess of amine. Suitable basic condensation agents are, for example, alkali metal hydroxides, such as sodium hydroxide or potassium hydroxide, alkali metal carbonates, such as potassium carbonate, and alkali metal alcoholates, for example alkali metal lower alkanolates, such as sodium methylate, potassium ethylate and potassium tertiary butylate.

It is also possible to react a compound of the formula IIab

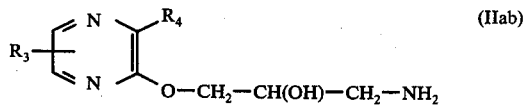
(IIab)

or IIbb

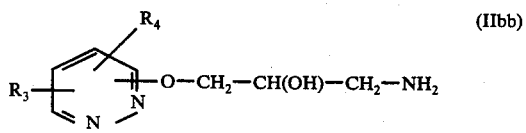
(IIbb)

or IIcb

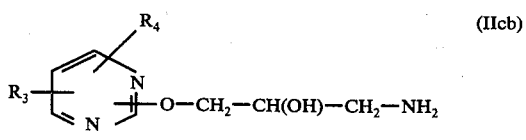
(IIcb)

wherein R$_3$ and R$_4$ have the above meanings, with a compound of the formula Z$_2$—C(CH$_3$)R$_1$R$_2$, wherein R$_1$ and R$_2$ have the above meanings and Z$_2$ is a reactive esterified hydroxyl group.

This reaction is carried out in the usual manner, preferably in the presence of a basic condensation agent and/or with an excess of amine. Suitable basic condensation agents are, for example, alkali metal alcoholates, especially sodium lower alkanolates or potassium lower alkanolates, for example sodium methylate, or alkali metal carbonates, such as sodium carbonate or potassium carbonate.

It is also possible to react a compound of the formula IV

Het — Z (IV)

wherein Z is a nucleophilically removable radical and Het has the above meaning, with a compound of the formula V

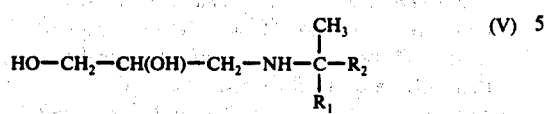

or with the corresponding condensation products with aldehydes, ketones or carbonic acid, wherein $R_1$ and $R_2$ have the above meanings.

A group Z which can be removed nucleophilically is, for example, a halogen atom, such as a chlorine, bromine or iodine atom, a nitro group, a lower alkylsulphonyloxy group, such as the methylsulphonyloxy group, a lower alkylsulphonyl group, such as the methylsulphonyl group, a lower alkylsulphinyl group, such as the methylsulphinyl group, a lower alkoxy group such as the methoxy or ethoxy group, or an ammonium group, such as the trimethylammonium or triethylammonium group. In the above terms, lower alkyl preferably has up to 7 C atoms and especially up to 4 C atoms.

Thus it is possible to react a compound of the formula IVa, or a corresponding pyrazine-N-oxide

or of the formula IVb, or a corresponding pyridazine-N-oxide

wherein Z preferably occupies the 3-position or 6-position of the pyridazine nucleus, or of the formula IVc, or a corresponding pyrimidine-N-oxide

wherein Z preferably occupies the 2-position, 4-position or 6-position of the pyrimidine ring, and $R_3$ and $R_4$ have the above meanings, with a compound of the formula V

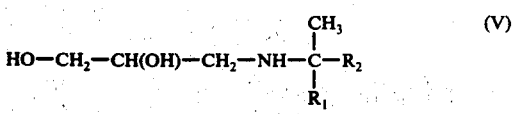

or with the corresponding condensation products with aldehydes, ketones or carbonic acid, wherein $R_1$ and $R_2$ have the above meanings.

This reaction is carried out in the usual manner, preferably in the presence of a basic condensation agent. Examples of suitable basic condensation agents are alkali metal hydroxides, such as sodium hydroxide or potassium hydroxide, alkali metal hydrides, such as sodium hydride or potassium hydride, and alkali metal alcoholates, such as sodium methylate, potassium ethylate and especially potassium tertiary butylate.

It is also possible, in a compound of the formula I, or in a corresponding N-oxide, wherein Het, $R_1$ and $R_2$ have the above meanings and which possesses a removable radical on the nitrogen atom of the amino group and/or on the hydroxyl group, to split off this radical or radicals.

Such radicals which can be split off are in particular radicals which can be split off by solvolysis or by reduction.

Radicals which can be split off by solvolysis are, in particular, radicals which can be split off by hydrolysis or ammonolysis.

Radicals which can be split off by hydrolysis are, for example, acyl radicals, such as optionally functionally modified carboxyl groups, for example oxycarbonyl radicals, such as alkoxycarbonyl radicals, for example the tert.-butoxycarbonyl radical or the ethoxycarbonyl radical, aralkoxycarbonyl radicals, such as phenyl-lower alkoxycarbonyl radicals, for example a carbobenzoxy radical, halogenocarbonyl radicals, for example the chlorocarbonyl radical and also arylsulphonyl radicals, such as toluenesulphonyl or bromobenzenesulphonyl radicals, and optionally halogenated, such as fluorinated, lower alkanoyl radicals, for example the formyl, acetyl or trifluoroacetyl radical, or a benzoyl radical, or nitrile groups or silyl radicals, such as tri-lower alkylsilyl radicals, for example the trimethylsilyl radical.

Radicals on the hydroxyl group which can be split off by hydrolysis are, amongst those mentioned, in particular oxycarbonyl radicals and lower alkanoyl radicals or benzoyl radicals such as, for example, those mentioned above.

Radicals on the amino group which can be split off by hydrolysis are not only those mentioned but also doubly bonded radicals, for example an alkylidene or benzylidene radical, or a phosphoranylidene group such as the triphenylphosphoranylidene group, in which case the nitrogen atom then carries a positive charge.

Further radicals on the hydroxyl group and on the amino group which can be split off by hydrolysis are divalent radicals, such as optionally substituted methylene. Possible substituents of the methylene radical are any desired organic radicals, the nature of a substituent of a methylene radical being immaterial with regard to the hydrolytic splitting-off of the radical. Examples of possible methylene substituents are aliphatic or aromatic radicals, such as lower alkyl, for example as mentioned above, and aryl, for example phenyl or pyridyl. The hydrolysis can be effected in the usual manner, especially in a basic medium or preferably in an acid medium, for example by means of mineral acids, such as hydrochloric acid.

Compounds with radicals which can be split off by hydrolysis are, for example, also compounds of the formula VIa

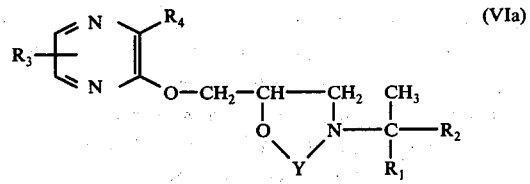

and of the formula VIb

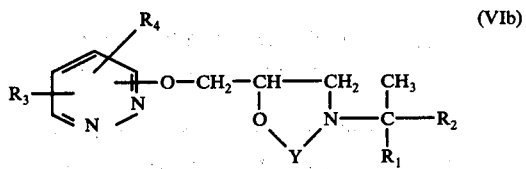

and of the formula VIc

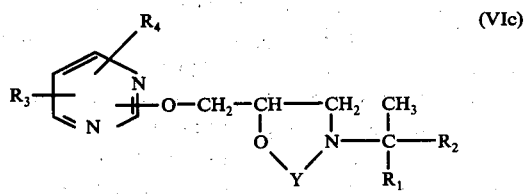

wherein $R_1$, $R_2$, $R_3$ and $R_4$ have the above meanings and Y represents a thiocarbonyl radical.

The hydrolysis is carried out in the usual manner, for example in the presence of hydrolysing agents, for instance in the presence of acid agents, such as, for example, aqueous mineral acids, such as sulphuric acid or hydrogen halide acid, or in the presence of basic agents, for example alkali metal hydroxides, such as sodium hydroxide. Oxycarbonyl radicals, arylsulphonyl radicals and nitrile groups can advantageously be split off by acid agents, such as by hydrogen halide acid, especially hydrobromic acid. Splitting off with, for example, aqueous hydrobromic acid, optionally mixed with acetic acid, is particularly suitable for this purpose. Nitrile groups are in particular split off by hydrobromic acid at an elevated temperature, such as in boiling hydrobromic acid, by the cyanogen bromide method (v. Braun).

Further it is possible to split off, for example, a tert.-butoxycarbonyl radical under anhydrous conditions by treatment with a suitable acid, such as trifluoroacetic acid.

In the case of the hydrolysis of compounds of the formula VIa, VIb, or VIc, in particular, acid agents are suitably used.

Radicals which can be split off by reduction are, for example, α-arylalkyl radicals, such as benzyl radicals, or α-aralkoxycarbonyl radicals, such as benzyloxycarbonyl radicals, which can be split off in the usual manner by hydrogenolysis, especially by catalytically activated hydrogen, such as by hydrogen in the presence of a hydrogenation catalyst, for example Raney nickel. Further radicals which can be split off by reduction are, for example, 2-halogeno-alkoxycarbonyl radicals, such as the 2,2,2-trichloroethoxy-carbonyl radical or the 2-iodoethoxy-carbonyl or 2,2,2-tribromoethoxy-carbonyl radical, which can be split off in the usual manner, especially by metallic reduction (so-called nascent hydrogen). Nascent hydrogen can be obtained by the action of metal or metal alloys, such as amalgams, on agents which yield hydrogen, such as carboxylic acids, alcohols or water, and in particular zinc or zinc alloys together with acetic acid can be used. The reduction of 2-halogeno-alkoxycarbonyl radicals can furthermore be effected by chromium-(II) compounds, such as chromium-(II) chloride or chromium-(II) acetate. A radical which can be split off by reduction can also be an arylsulphonyl group, such as the toluenesulphonyl group, which can be split off in the usual manner by reduction with nascent hydrogen, for example by means of an alkali metal, such as lithium or sodium, in liquid ammonia, or electrolytically, and can in particular be split off from a N atom. In carrying out the reduction, care must be taken that other reducible groups shall not be attacked.

It is also possible to reduce a compound corresponding to the formula I, or a corresponding pyrazine-N-oxide, pyridazine-N-oxide or pyrimidine-N-oxide, wherein the nitrogen of the propoxy chain is bonded to one of its substituents by a double bond, or wherein one of the carbon atoms bonded to the nitrogen atom carries a hydroxyl group.

Thus, for example, a Schiff's base of the formula VIIa

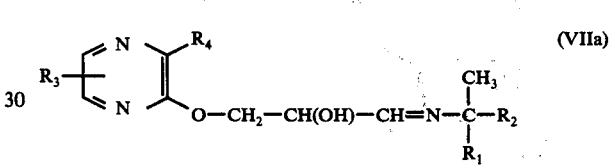

or of the formula VIIb

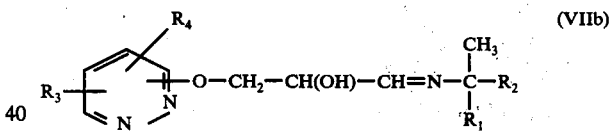

or of the formula VIIc

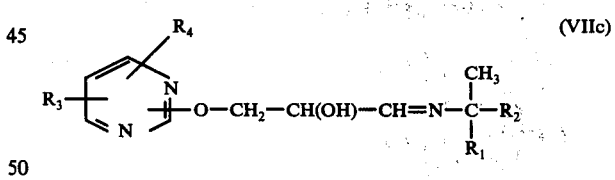

wherein $R_1$, $R_2$, $R_3$ and $R_4$ have the above meanings, or a Schiff's base of the formula VIIIa

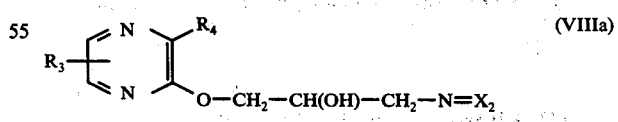

or of the formula VIIIb

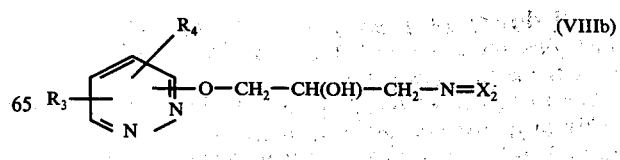

or of the formula VIIIc

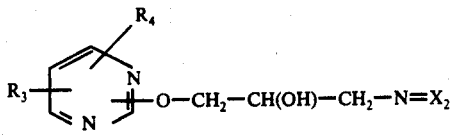 (VIIIc)

wherein $R_3$ and $R_4$ have the above meanings and $-X_2H$ represents $-CH(CH_3)R_2$, with $R_2$ having the above meaning, or a ring tautomer corresponding to the formula VIIIa, of the formula IXa

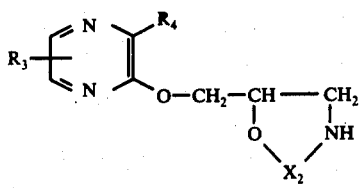 (IXa)

or of the formula IXb corresponding to the formula VIIIb

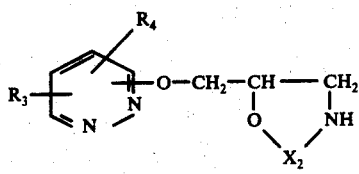 (IXb)

or of the formula IXc corresponding to the formula VIIIc

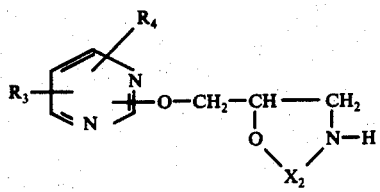 (IXc)

wherein $R_3$ and $R_4$ and $-X_2H$ have the above meanings and wherein compounds of the formulae VIIIa and IXa, or VIIIb and IXb, or VIIIc and IXc can also be present alongside one another, can be reduced.

This reduction is effected in the usual manner, for example with a di-light metal hydride, such as an alkali metal borohydride or alkali metal aluminium hydride, for example lithium aluminium hydride, with an alkali metal cyanoborohydride, for example sodium cyanoborohydride, with a hydride, such as diborane, or with hydrogen in the presence of a hydrogenation catalyst, for example platinum, palladium or nickel, such as Raney nickel. It is necessary to ensure that during the reduction other reducible groups are not attacked.

It is also possible to react a compound of the formula X or the corresponding pyrimidine-N-oxide

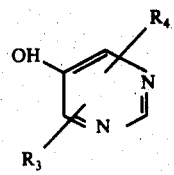 (X)

wherein $R_3$ and $R_4$ have the above meanings, with a compound of the formula Xa

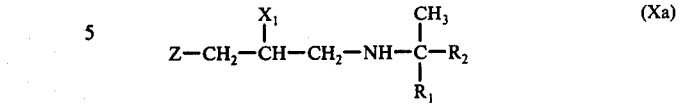 (Xa)

wherein Z represents a reactive esterified hydroxyl group and $X_1$ denotes the hydroxyl group and $R_1$ and $R_2$ have the above meanings, or wherein $X_1$ and Z together form an epoxy group, or with the corresponding cyclised compound of the formula Xb

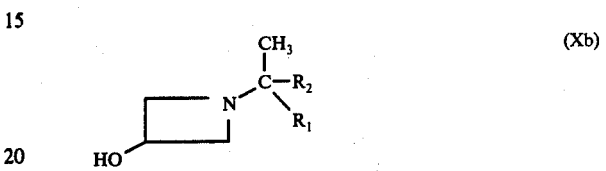 (Xb)

A reactive esterified hydroxyl group is in particular a hydroxyl group esterified by a strong inorganic or organic acid, above all a hydrogen halide acid, such as hydrochloric acid, hydrobromic acid or hydriodic acid, or sulphuric acid or a strong organic sulphonic acid such as, for example, benzenesulphonic acid, 4-bromobenzenesulphonic acid, 4-toluenesulphonic acid or methanesulphonic acid. Thus, Z in particular represents chlorine, bromine or iodine.

This reaction is carried out in the usual manner. If reactive esters are used as the starting material, the compound of the formula X can perferentially be used in the form of its metal alcoholate, such as alkali metal alcoholate, for example sodium alcoholate, or the reaction is carried out in the presence of an acid-binding agent, especially of a condensation agent which can form a salt with the compound of the formula X, such as an alkali metal alcoholate. If starting compounds of the formula Xb are used, the basic condensation agent used is preferably an alkali metal hydroxide, such as, for example, potassium hydroxide or sodium hydroxide.

Compounds of the formula I, wherein Het is pyridyl and $R_1$ and $R_2$ have the above meanings, can be prepared, for example, according to the following methods:

For example, a compound of the formula XI or the corresponding pyridine-N-oxide

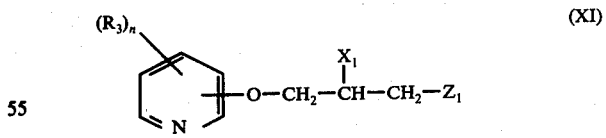 (XI)

can be reacted with a compound of the formula III $$Z_2-C(CH_3)R_1R_2 \quad \text{(III)}$$

wherein $R_1$, $R_2$ and $R_3$ have the above meanings and one of the radicals $Z_1$ and $Z_2$ is amino and the other is a reactive esterified hydroxyl group and $X_1$ is hydroxyl, or $Z_1$ together with $X_1$ forms an epoxy group if $Z_2$ is amino.

Thus, a compound of the formula XIa or the corresponding pyridine-N-oxide

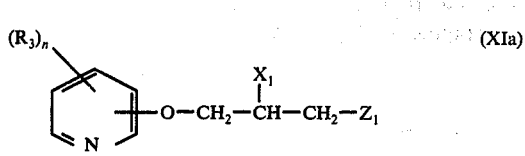

wherein $R_3$ and n have the above meanings, $X_1$ represents the hydroxyl group and $Z_1$ represents a reactive esterified hydroxyl group, or $X_1$ and $Z_1$ together form an epoxy group, can be reacted with an amine of the formula $NH_2—C(CH_3)R_1R_2$, wherein $R_1$ and $R_2$ have the above meanings.

A reactive, esterified hydroxyl group is in particular a hydroxyl group esterified by a strong inorganic or organic acid, above all a hydrogen halide acid, such as hydrochloric acid, hydrobromic acid or hydriodic acid, or sulphuric acid or a strong organic sulphonic acid, such as, for example, benzenesulphonic acid, 4-bromobenzenesulphonic acid, 4-toluenesulphonic acid or methanesulphonic acid. Thus Z in particular represents chlorine, bromine or iodine.

This reaction is carried out in the usual manner. If a reactive ester is used as the starting material, the reaction is preferably carried out in the presence of a basic condensation agent and/or with an excess of amine. Examples of suitable basic condensation agents are alkali metal hydroxides, such as sodium hydroxide or potassium hydroxide, alkali metal carbonates, such as potassium carbonate, and alkali metal alcoholates, for example alkali metal lower alkanolates, such as sodium methylate, potassium ethylate and potassium tertiary butylate.

Thus it is also possible to react a compound of the formula XII

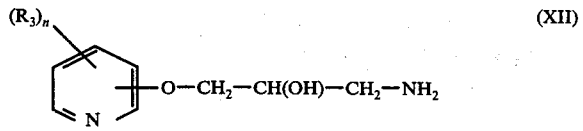

wherein $R_3$ and n have the above meanings, with a compound of the formula $Z_2—C(CH_3)R_1R_2$, wherein $R_1$ and $R_2$ have the above meanings and $Z_2$ is a reactive esterified hydroxyl group.

This reaction is carried out in the usual manner, preferably in the presence of a basic condensation agent and/or with an excess of amine. Examples of suitable basic condensation agents are alkali metal alcoholates, especially sodium alcoholate or potassium alcoholate, or alkali metal carbonates, such as sodium carbonate or potassium carbonate.

It is also possible to react a compound of the formula XIII or the corresponding pyridine-N-oxide

wherein $R_3$ and n have the above meanings, and Z is a radical which can be split off nucleophilically, the group Z being in the 2-position, 4-position or 6-position of the pyridine ring, with a compound of the formula XIV

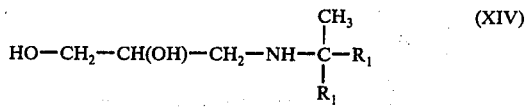

or with the corresponding condensation products with aldehydes, ketones or carbonic acid, wherein $R_1$ and $R_2$ have the above meanings. A group Z which can be split off nucleophilically is, for example, a halogen atom, such as a chlorine, bromine or iodine atom, a nitro group, a lower alkylsulphonyloxy group such as the methylsulphonyloxy group, a lower alkylsulphonyl group, such as the methylsulphonyl group, a lower alkylsulphinyl group, such as the methylsulphinyl group, a lower alkoxy group, such as the methoxy or ethoxy group, or an ammonium group, such as the trimethylammonium or triethylammonium group. In the above terms, lower alkyl preferably has up to 7 C atoms and especially up to 4 C atoms.

This reaction is carried out in the usual manner, preferably in the presence of a basic condensation agent. Suitable basic condensation agents are, for example, alkali metal hydroxides, such as sodium hydroxide or potassium hydroxide, alkali metal hydridides, such as sodium hydride or potassium hydride and alkali metal alcoholates, especially sodium alcoholates or potassium alcoholates, for example sodium methylate, potassium ethylate and especially potassium tertiary butylate.

It is also possible to react a compound of the formula XV or the corresponding pyridine-N-oxide

wherein $R_3$ and n have the above meanings, with a compound of the formula XVI

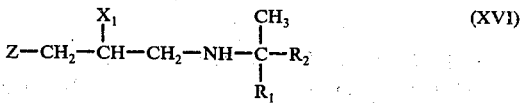

wherein $Z$, $X_1$, $R_1$ and $R_2$ have the above meanings, or with the corresponding cyclised compound of the formula XVIa

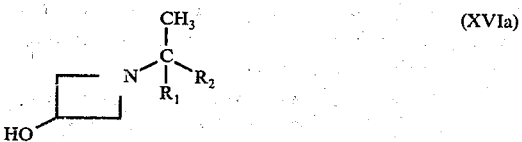

This reaction is carried out in the usual manner. If reactive esters are used as the starting material, the compound of the formula XV can preferably be used in the form of its metal alcoholate, such as alkali metal alcoholate, for example sodium alcoholate, or the reaction is carried out in the presence of an acid-binding agent, especially of a condensation agent which can form a salt with the compound of the formula XV, such as an alkali metal alcoholate. If starting compounds of the formula XVIa are used, the basic condensation agent used is preferably an alkali metal hydroxide, such as, for example, potassium hydroxide or sodium hydroxide.

It is also possible, in a compound of the formula I or in the corresponding pyridine-N-oxide, wherein $R_1$, $R_2$, $R_3$ and n have the above meanings and which possesses a radical which can be split off on the nitrogen atom of the amino group and/or on the hydroxyl group, to split off this radical or these radicals. Such radicals which can be split off are in particular radicals which can be split off by solvolysis or reduction.

Radicals which can be split off by solvolysis are in particular radicals which can be split off by hydrolysis or ammonolysis.

Radicals which can be split off by hydrolysis are, for example, acyl radicals, such as optionally functionally modified carboxyl groups, for example oxycarbonyl radicals, such as alkoxycarbonyl radicals, for example the tert.butoxycarbonyl radical or the ethoxycarbonyl radical, aralkoxycarbonyl radicals, such as phenyl-lower alkoxycarbonyl radicals, for example a carbobenzoxy radical, and halogenocarbonyl radicals, for example the chlorocarbonyl radical, and also arylsulphonyl radicals, such as toluenesulphonyl radicals or bromobenzenesulphonyl radicals, and optionally halogenated, such as fluorinated, lower alkanoyl radicals, for example the formyl, acetyl or trifluoroacetyl radical, or benzoyl radical, or nitrile groups or silyl radicals, such as tri-lower alkylsilyl radicals, for example the trimethylsilyl radical.

Suitable radicals on the hydroxyl group which can be split off by hydrolysis are, amongst those mentioned, especially oxycarbonyl radicals and lower alkanoyl radicals or benzoyl radicals, such as, for example, those mentioned above.

Possible radicals on the amino group which can be split off by hydrolysis are not only those mentioned but also doubly bonded radicals, for example an alkylidene radical or benzylidene radical or a phosphoranylidene group, such as the triphenylphosphoranylidene group, in which case the nitrogen atom then carries a positive charge.

Further radicals on the hydroxyl group and on the amino group which can be split off by hydrolysis are divalent radicals, such as optionally substituted methylene. Possible substituents of the methylene radical are any desired organic radicals, the nature of a substituent of a methylene radical being immaterial with regard to the hydrolytic splitting-off. Possible methylene substituents are, for example, aliphatic or aromatic radicals, such as lower alkyl, for example as mentioned above, aryl, for example phenyl, or pyridyl. The hydrolysis can be carried out in the usual manner, especially in a basic medium or preferably in an acid medium, for example with mineral acids, such as hydrochloric acid.

Compounds with radicals which can be split off by hydrolysis are, for example, also compounds of the formula

XVII (XVII)

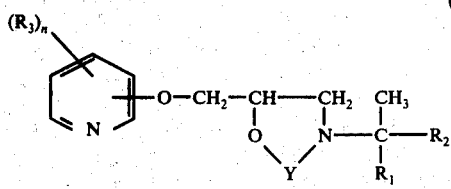

wherein $R_1$, $R_2$, $R_3$ and n have the above meanings and Y represents a thiocarbonyl radical.

The hydrolysis is carried out in the usual manner, for example in the presence of hydrolysing agents, for example in the presence of acid agents, such as, for example, aqueous mineral acids, such as sulphuric acid or hydrogen halide acid, or in the presence of basic agents, for example alkali metal hydroxides, such as sodium hydroxide. Oxycarbonyl radicals, arylsulphonyl radicals and nitrile groups can advantageously be split off by acid agents, such as by hydrogen halide acid, especially hydrobromic acid. A particularly suitable method of splitting off is, for example, by means of aqueous hydrobromic acid, optionally mixed with acetic acid. Nitrile groups are in particular split off by hydrobromic acid at an elevated temperature, such as in boiling hydrobromic acid, by the cyanogen bromide method (v. Braun).

It is also possible, for example, to split off a tert.-butoxycarbonyl radical under anhydrous conditions by treatment with a suitable acid, such as trifluoroacetic acid.

In the hydrolysis of compounds of the formula XVII, in particular, acid agents are suitably used.

Radicals which can be split off by reduction are, for example, α-arylalkyl radicals, such as benzyl radicals, or α-aralkoxycarbonyl radicals, such as benzyloxycarbonyl radicals, which can be split off in the customary manner by hydrogenolysis, especially by catalytically activated hydrogen, such as by hydrogen in the presence of a hydrogenation catalyst, for example Raney nickel. Examples of further radicals which can be split off by reduction are 2-halogeno-alkoxycarbonyl radicals, such as the 2,2,2-trichloroethoxy-carbonyl radical or the 2-iodoethoxy-carbonyl or 2,2,2-tribromoethoxy-carbonyl radical, which can be split off in the usual manner, especially by metallic reduction (so-called nascent hydrogen). The nascent hydrogen can be obtained by the action of metal or metal alloys, such as amalgams, on agents which yield hydrogen, such as carboxylic acids, alcohols or water, and in particular zinc or zinc alloys together with acetic acid can be used. The reduction of 2-halogeno-alkoxycarbonyl radicals can also be effected by chromium-(II) compounds such as chromium-(II) chloride or chromium-(II) acetate. A radical which can be split off by reduction can also be an arylsulphonyl group, such as the toluenesulphonyl group, which can be split off, especially split off from a N atom, in the usual manner by reduction with nascent hydrogen, for example by means of an alkali metal, such as lithium or sodium, in liquid ammonia, or electrolytically. In carrying out the reduction, care must be taken that other reducible groups are not attacked.

It is also possible to reduce a compound which corresponds to the formula I, or the corresponding pyridine-N-oxide, wherein the nitrogen of the propoxy chain is bonded by one of its substituents by a double bond, or wherein one of the carbon atoms bonded to the nitrogen atom carries a hydroxyl group.

Thus, for example, it is possible to reduce a Schiff's base of the formula XVIII

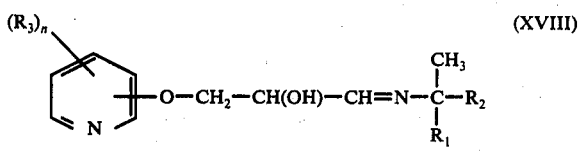

wherein $R_1$, $R_2$, $R_3$ and n have the above meanings, or of the formula XIX

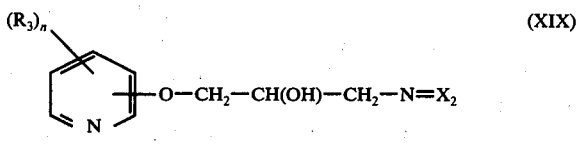

wherein $R_3$ and n have the above meanings and $-X_2H$ represents $-CH(CH_3)R_2$, with $R_2$ having the above meaning, or a ring tautomer corresponding to the formula XIX, of the formula XX

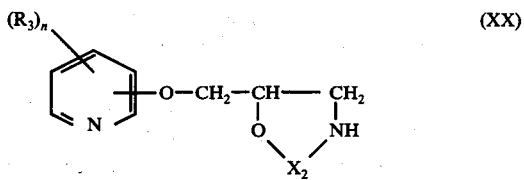

wherein $R_3$ and n have the above meanings and $-X_2H$ is $-CH(CH_3)R_2$, with $R_2$ having the above meaning, it also being possible for compounds of the formulae XIX and XX to be present alongside one another.

This reduction is effected in the customary manner, for example with a di-light metal hydride, such as an alkali metal borohydride or alkali metal aluminium hydride, for example lithium aluminium hydride, with a hydride, such as diborane, or with hydrogen in the presence of a hydrogenation catalyst, for example platinum, palladium or nickel, such as Raney nickel. In carrying out the reduction care must be taken that other reducible groups are not attacked.

In resulting compounds it is possible, within the scope of the end products, to modify, introduce or split off substituents in the usual manner; alternatively, resulting compounds can be converted into other end products in the usual manner.

Thus, in resulting compounds with a C—C double bond, this double bond can be converted into a C—C single bond in the usual manner by catalytic hydrogenation, such as by hydrogen in the presence of a hydrogenation catalyst, for example platinum, palladium or nickel, such as Raney nickel. In doing so, care must be taken that other reducible groups are not attacked. Thus care must be taken especially in the reduction with Raney nickel and hydrogen that halogen atoms which may be present and are bonded to aromatic rings are not replaced by hydrogen. In addition, care must be taken with regard to a thioether grouping in the case of all reductions, especially catalytic hydrogenations. Sulphur-resistant catalysts should be used preferably, and if appropriate the hydrogen absorption should be followed volumetrically and the hydrogenation discontinued after the calculated amount has been absorbed.

In resulting compounds with one or more phenyl nuclei, this nucleus or these nuclei can be halogenated. This can be effected in the usual manner, especially without raising the temperature or with cooling and in the presence of a catalyst, such as iron, iodine, iron-III chloride, aluminium chloride or the corresponding bromides.

Free carboxyl-lower alkyl groups $R_2$ can be esterified in the usual manner, for example by reaction with an appropriate alcohol, advantageously in the presence of an acid, such as a mineral acid, for example sulphuric acid or hydrochloric acid, or in the presence of a water-binding agent, such as dicyclohexylcarbodiimide, or by reaction with an appropriate diazo compound, for example a diazoalkane. The esterification can also be carried out by reaction of a salt, preferably of an alkali metal salt, of the acid with a reactively esterified alcohol, for example a halide, such as the chloride, of the corresponding alcohol.

Free carboxy-lower alkyl groups can be amidised in the usual manner, for example by reaction with ammonia or a primary or secondary amine, advantageously in the presence of a water-binding agent such as dicyclohexylcarbodiimide.

In compounds which carry an esterified carboxy-lower alkyl group $R_2$, the latter can be converted into the free carboxy-lower alkyl group $R_2$ in the usual manner, for example by hydrolysis, preferably in the presence of strong bases, such as an alkali metal hydroxide, for example sodium hydroxide or potassium hydroxide, or strong acids, for example a strong mineral acid, such as a hydrogen halide acid, for example hydrochloric acid or sulphuric acid.

In compounds which contain an esterified carboxy-lower alkyl group $R_2$, the latter can be converted into the corresponding carbamoyl-lower alkyl compound in the usual manner by aminolysis with a primary or secondary amine or with ammonia.

Compounds which carry a carbamoyl-lower alkyl group $R_2$ can be dehydrated to the corresponding cyano-lower alkyl compounds in the usual manner, for example by the action of dehydrating agents, such as phosphorus pentoxide or phosphorus oxychloride, preferably at elevated temperatures.

Compounds which carry a cyano-lower alkyl group $R_2$ can be saponified in the usual manner, for example in the presence of concentrated aqueous acids or alkali metal hydroxides, to give the corresponding carbamoyl-lower alkyl compounds, or directly to the carboxy-lower alkyl compounds.

Compounds which carry a cyano-lower alkyl group $R_2$ can be saponified in the usual manner, for example by addition of alcohols in the presence of anhydrous hydrogen chloride and subsequent decomposition of the resulting imido-ester, for example in water, to give the corresponding esterified carboxy-lower alkyl groups $R_2$.

It is also possible, in resulting compounds in which $R_3$ and/or $R_4$ is lower alkylamino, to convert the lower alkylamino group or groups in the usual manner into a di-lower alkylamino group $R_3$ and/or $R_4$. This reaction is carried out with a reactive ester of a corresponding alcohol, such as Z-lower alkyl, wherein Z has the above meaning, preferably in the presence of a basic condensation agent. Suitable basic condensation agents are nitrogen bases, alkali metal hydroxides, alkali metal carbonates and alkali metal alcoholates such as, for example, pyridine, triethylamine, sodium hydroxide, potassium hydroxide, sodium carbonate, potassium carbonate, sodium methylate, potassium methylate, sodium ethylate or potassium ethylate.

It is also possible, in resulting compounds in which $R_3$ and/or $R_4$ is halogen, to replace the halogen group or groups in the usual manner by lower alkylamino, di-lower alkylamino, lower alkyleneamino, hydroxy-lower alkyleneamino, oxa-lower alkyleneamino, thia-lower alkyleneamino or aza-lower alkyleneamino by means of a corresponding amine, or to replace them by lower alkoxy, lower alkenyloxy, lower alkoxy-lower alkoxy or hydroxyl by means of a corresponding alcohol, or to replace them by lower alkylthio by means of a corresponding mercaptan. For these reactions, a basic condensation agent is preferably used, such as, for example, nitrogen bases, alkali metal hydroxides, alkali metal carbonates and alkali metal alcoholates, such as, for example, pyridine, triethylamine, sodium hydroxide, potassium hydroxide, sodium methylate, potassium methylate, sodium ethylate or potassium ethylate.

It is further possible, in resulting compounds which are substituted by halogen in the heterocyclic structure and/or which carry halogen-substituted phenyl groups, to remove the halogen atoms by catalytic hydrogenation. The reaction is carried out with hydrogen and the customary hydrogenation catalysts, such as Raney nickel or palladium on charcoal.

It is further possible, in a compound of the formula XXIIIa, or in a corresponding pyrazine-N-oxide

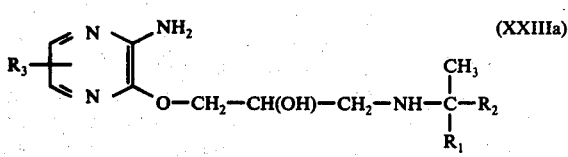

(XXIIIa)

or of the formula XXIIIb, or in a corresponding pyridazine-N-oxide

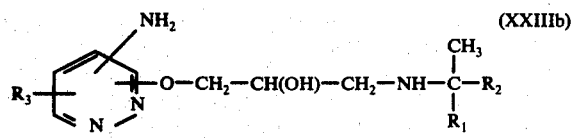

(XXIIIb)

or of the formula XXIIIc, or in a corresponding pyrimidine-N-oxide

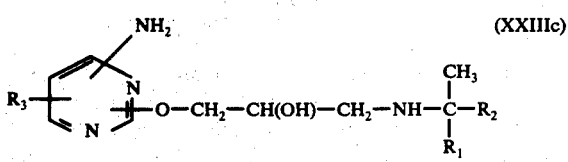

(XXIIIc)

to convert the primary amino group into a lower alkylamino or di-lower alkylamino group by reaction with a compound of the formula XXIV

Z — lower alkyl        (XXIV)

wherein Z is a reactive esterified hydroxyl group.

This reaction is carried out in the usual manner, preferably in the presence of a basic condensation agent. Suitable basic condensation agents are nitrogen bases, such as pyridine or triethylamine, alkali metal hydroxides, such as sodium hydroxide or potassium hydroxide, alkali metal carbonates, such as sodium carbonate or potassium carbonate, and alkali metal alcoholates, such as sodium methylate, sodium ethylate, potassium methylate or potassium ethylate.

It is also possible to convert the primary amino group or groups into the acylamino group or groups in a compound of the formula XXVa or in a corresponding pyrazine-N-oxide

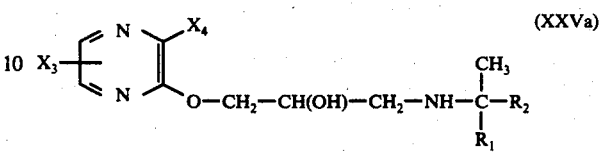

(XXVa)

wherein $R_1$ and $R_2$ have the above meanings and $X_3$ is amino or identical to $R_3$ and $X_4$ is amino or identical to $R_4$, or of the formula XXVb, or in a corresponding pyridazine-N-oxide

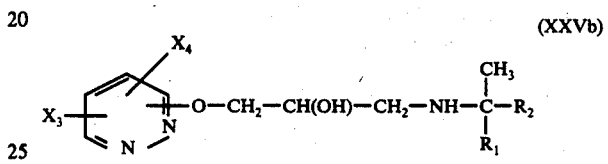

(XXVb)

wherein $R_1$ and $R_2$ have the above meanings and $X_3$ is amino or identical to $R_3$ and $X_4$ is amino or identical to $R_4$, or of the formula XXVc, or in a corresponding pyrimidine-N-oxide

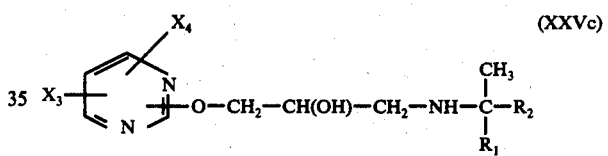

(XXVc)

wherein $R_1$ and $R_2$ have the above meanings $X_3$ is amino or identical to $R_3$ and $X_4$ is amino or identical to $R_4$, or of the formula XXVd or in a corresponding pyridine-N-oxide

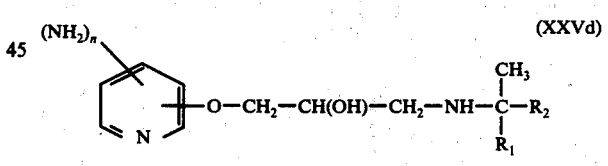

(XXVd)

wherein $n$, $R_1$ and $R_2$ have the above meanings.

The reaction is carried out with a customary acylating agent, such as a reactive derivative of a carboxylic acid, especially of an optionally substituted benzoic acid or of a lower alkanecarboxylic acid, for example of acetic acid, or of an aryl-lower alkanecarboxylic acid, for example of phenylacetic acid. Particularly suitable acylating agents are the anhydride or the ketone of one of the acids mentioned or the mixed anhydride of these acids with a strong inorganic acid, such as a hydrogen halide acid, especially hydrochloric acid or hydrobromic acid, or with an organic acid, or an activated amide or an activated ester of one of the acids mentioned.

Activated esters are, for example, esters with electron-attracting structures, such as esters of phenol, thiophenol, p-nitrophenol, cyanomethyl alcohol and the like. Activated amides are, for example, the N-acyl derivatives of pyrazoles such as 3,5-dimethylpyrazole or imidazoles, such as imidazole itself. Further suitable acylating agents are activated formic acid esters such as, for example, halogenoformic acid esters, especially chloroformic acid esters. Depending on the nature of the acylating component, it can be desirable to use a condensation agent. Thus, disubstituted carbodiimides assist the reaction of the acids, whilst bases, such as tertiary amines, for example tri-lower alkylamines, N,N-di-lower alkylanilines or aromatic tertiary nitrogen bases, such as pyridine or quinoline, or inorganic bases, such as alkali metal hydroxides or alkaline earth metal hydroxides, alkali metal carbonates or alkaline earth metal carbonates, alkali metal bicarbonates or alkaline earth metal bicarbonates, for example sodium hydroxide, potassium hydroxide or calcium hydroxide, or sodium carbonate or bicarbonate, potassium carbonate or bicarbonate or calcium carbonate or bicarbonate, or acylate ions assist the reaction of acid anhydrides, acid halides and activated formic acid esters.

It is also possible, in a compound of the formula XXVd, or in a corresponding pyridine-N-oxide, to convert the primary amino group or groups into a lower alkylamino or di-lower alkylamino group by reaction with a compound of the formula XXVI lower alkyl — Z     (XXVI)

wherein Z is a reactive esterified hydroxyl group.

This reaction is carried out in the usual manner, preferably in the presence of a basic condensation agent. Suitable basic condensation agents are nitrogen bases, such as pyridine or triethylamine, alkali metal hydroxides such as sodium hydroxide or potassium hydroxide, alkali metal carbonates such as sodium carbonate or potassium carbonate and alkali metal alcoholates such as sodium methylate, sodium ethylate, potassium methylate or potassium ethylate.

Furthermore it is possible, in resulting compounds of the formula I which are substituted by alkylthio in the heterocyclic structure, to remove the alkylthio group or groups by hydrogenation. The hydrogenation is preferably carried out in the presence of Raney nickel and preferably in a lower alkanol, such as methanol or ethanol. The reaction is preferably carried out at an elevated temperature, for example at the reflux temperature of the solvent.

It is furthermore possible, in resulting compounds of the formula I, wherein $R_3$ and/or $R_4$ denotes lower alkylsulphonyl, to replace the lower alkylsulphonyl group or groups by hydroxyl, lower alkoxy, lower alkoxy-lower alkoxy, lower alkenyloxy, lower alkylthio-lower alkoxy, lower alkylthio, phenylthio, lower alkylamino, di-lower alkylamino, lower alkyleneamino, oxa-lower alkyleneamino, aza-lower alkyleneamino or thia-lower alkyleneamino. The replacement is effected in the usual manner, preferably in the presence of a basic condensation agent, such as alkali metal hydroxides, for example sodium hydroxide or potassium hydroxides, or alkali metal alcoholates, for example sodium methylate, sodium ethylate, potassium methylate or potassium ethylate. Furthermore it is possible, in resulting compounds of the formula Ia which carry a di-lower alkylamino group in the 3-position, 5-position or 6-position, or in resulting compounds of the formulae Ic and Id, which carry a di-lower alkylamino group in the 2-position, 4-position or 6-position, or in resulting compounds of the formula Ib which carry a di-lower alkylamino group in the 3-position or 6-position, to replace this di-lower alkylamino group by the hydroxyl group. The replacement is effected in the usual manner, preferably in the presence of an acid condensation agent, such as aqueous mineral acids, for example dilute sulphuric acid or hydrogen halide acids, such as hydrochloric acid.

Furthermore it is possible, in resulting compounds of the formula I which carry an amino-lower alkyl group, to acylate this amino-lower alkyl group. The acylation is effected in the usual manner with a suitable acylating agent, for example a corresponding acid halide, such as an acid chloride, or a corresponding anhydride or a corresponding halogenoformic acid ester, for example a chloroformic acid ester. Furthermore it is possible, in resulting compounds of the formula Id, wherein $R_3$ denotes a nitro group, to reduce this nitro group to the amino group. This reduction is effected in the usual manner, for example with catalytically activated hydrogen and preferably in a high-boiling solvent, such as, for example, dimethylformamide or dioxane. Possible hydrogenation catalysts are the customary catalysts, such as Raney nickel, palladium on charcoal, platinum and the like.

Condensation products of the formula Iy can be obtained by reacting an amine of the formula I with an aldehyde or ketone of the formula X=O, wherein X has the above meaning, or with a reactive carbonyl derivative thereof.

Reactive carbonyl derivatives are above all acetals, ketals, hemithioketals and thioketals, especially dimethyl- or diethyl-acetals, -ketals or -thioketals, or acylals, especially those with acetic acid or with a hydrogen halide acid, for example compounds of the formulae $XCl_2$ or $XBr_2$, wherein X has the above meaning.

This reaction is carried out in the usual manner, in the presence or absence of a solvent, at room temperature or preferably at elevated temperature, if necessary in the presence of a condensation agent, especially of an acid condensation agent.

Condensation products of the formula Iz can be obtained by reacting an amine of the formula I with carbonic acid or with one of its reactive derivatives.

Reactive carbonic acid derivatives are, for example, carbonyl halides, such as, in particular, phosgene or carbonyl bromide, and also carbonic acid monoesters or diesters, such as lower alkyl esters, for example carbonic acid dimethyl ester and chloroformic acid methyl ester.

This reaction is carried out in the usual manner, preferably in the presence of a solvent and at lowered temperature, room temperature or raised temperature, if necessary in the presence of a condensation agent, especially of a basic condensation agent.

Correspondingly, a condensation product of the formula Iy or Iz can be converted in the usual manner, by hydrolysis, into an amine of the formula I, for example in a basic medium or preferably in an acid medium.

In resulting compounds of the formula I, wherein $R_3$ denotes nitrile, the nitrile group can be converted into the aminomethyl group in the usual manner. Preferably, the conversion is effected by hydrogenation by means of catalytically activated hydrogen in the presence of ammonia. Possible hydrogenation catalysts are the customary noble metal catalysts, such as palladium on charcoal or platinum, and also, above all, Raney nickel.

Furthermore, resulting mono-N-oxides and di-N-oxides can be converted into the corresponding non-oxidised compounds in the usual manner. The reaction can be effected, for example, with sulphurous acid at room temperature or slightly elevated temperature, with phosphorus oxychloride or above all by catalytic hydrogenation. Suitable hydrogenation catalysts are, for example, noble metal catalysts, such as platinum or palladium on charcoal, and also Raney nickel.

Furthermore, non-oxidised compounds can be converted into the corresponding N-oxides in the usual manner. The oxidation is effected with one of the customary oxidising agents, such as organic per-acids, for example peracetic acid, perbenzoic acid or m-chloroperbenzoic acid, or with hydrogen peroxide, for example a hydrogen peroxide/glacial acetic acid mixture. The reaction is carried out at room temperature or elevated temperature. If perbenzoic acid or m-chloroperbenzoic acid is used, the reaction is preferably carried out in a chlorinated hydrocarbon, such as, for example, methylene chloride or chloroform.

The reactions mentioned can optionally be carried out simultaneously or successively and in optional sequence.

The reactions mentioned are carried out in the usual manner in the presence or absence of diluents, condensation agents and/or catalytic agents, at lowered, ordinary or raised temperature and in a closed vessel if appropriate.

Depending on the process conditions and starting materials, the end products are obtained in the free form or in the form of their acid addition salts which is also included in the invention. Thus, for example, basic, neutral or mixed salts and at times also hemihydrates, monohydrates, sesquihydrates or polyhydrates thereof, can be obtained. The acid addition salts of the new compounds can be converted into the free compound in a manner which is in itself known, for example with basic agents, such as alkalis or ion exchangers. On the other hand, the resulting free bases can form salts with organic or inorganic acids. The acids used to produce acid addition salts are in particular those suitable for forming therapeutically usable salts. As examples of such acids there may be mentioned hydrogen halide acids, sulphuric acids, phosphoric acids, nitric acid, perchloric acid and aliphatic alicyclic, aromatic or heterocyclic carboxylic acids or sulphonic acids, such as formic acid, acetic acid, propionic acid, succinic acid, glycollic acid, lactic acid, malic acid, tartaric acid, citric acid, ascorbic acid, maleic acid, fumaric acid or pyruvic acid, phenylacetic acid, benzoic acid, anthranilic acid, p-hydroxybenzoic acid, salicylic acid, embonic acid, methanesulphonic acid, ethanesulphonic acid, hydroxyethanesulphonic acid and ethylenesulphonic acid, halogenobenzenesulphonic acids, toluenesulphonic acid, naphthalenesulphonic acid, sulphanilic acid or cyclohexylaminesulphonic acid.

These or other salts of the new compounds such as, for example, the picrates or perchlorates, can also be used for purifying the resulting free bases by converting the free bases into salts, isolating the latter and again liberating the bases from the salts. Because of the close relationships between the new compounds in the free form and in the form of their salts the free compounds are to be understood, in the preceding and subsequent text, where appropriate also to include the corresponding salts, in respect of general sense and intended use.

The invention also relates to those embodiments of the process according to which a compound obtainable as an intermediate product at any stage of the process is used as the starting material and the missing process steps are carried out, or the process is stopped at any stage or a starting material is formed under the reaction conditions or a reaction component is present in the form of its salts, if appropriate.

Thus it is possible to react an amine of the formula IIab, IIbb, IIcb or XII with an aldehyde or ketone of the formula $O=X_2$, wherein $X_2$ has the above meaning, in the presence of a suitable reducing agent, such as one of those mentioned above. This gives, as the intermediate product, a compound of the formula VIIIa, VIIIb, VIIIc or XIX or of the formula IXa, IXb, IXc or XX, which is then reduced in accordance with the invention.

Depending on the choice of the starting materials and procedures the new compounds can be in the form of optical antipodes or racemates or, if they contain at least two asymmetric carbon atoms, also of isomer mixtures, (racemate mixtures).

Resulting isomer mixtures (racemate mixtures) can be separated into the two stereoisomeric (diastereomeric) pure racemates on the basis of the physico-chemical differences of the constituents in a known manner, for example by chromatography and/or fractional crystallisation.

Resulting racemates can be resolved into the diastereomers according to known methods, for example by recrystallisation from an optically active solvent, with the aid of micro-organisms or by reaction with an optically active acid which forms salts with the racemic compound and separation of the salts obtained in this manner, for example on the basis of their differing solubilities, and the antipodes can be liberated from the diastereomers by the action of suitable agents. Particularly customary optically active acids are, for example, the D- and L-forms of tartaric acid, di-o-toluyltartaric acid, malic acid, mandelic acid, camphorsulphonic acid, glutamic acid, aspartic acid or quinic acid. Advantageously, the more active of the two antipodes is isolated.

Appropriately, the starting materials used to carry out the reactions according to the invention are those which lead to the initially particularly mentioned groups of end product and especially to the end products which have specifically been described or singled out.

The starting materials are known or can, if they are new, be obtained according to methods which are in themselves known.

Compounds of the formulae IIa, IIb, IIc or XI can be obtained, for example, when $(R_3)(R_4)$-pyrazinols or -pyridazinols or -pyrimidinols or $(R_3)_n$-pyridinols are reacted with epichlorohydrin. Compounds VIa, VIb, VIc or XVII can be obtained, for example, when a $(R_3)(R_4)$-halogenopyrazine or -halogenopyridazine or -halogenopyrimidine or a $(R_3)_n$-halogenopyridine is reacted with a compound XXIII

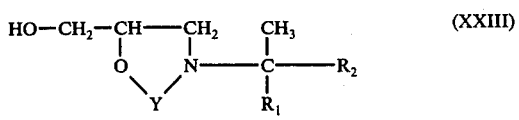

wherein $R_1$, $R_2$ and Y have the above meanings. Compounds of the formulae Xa, Xb, Xc or XXI can be obtained, for example, when $(R_3)(R_4)$-pyrazinols or -pyridazinols or -pyrimidinols or $(R_3)_n$-pyridinols are reacted with compounds of the formula XXIV

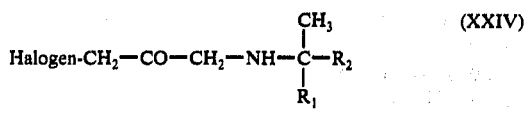

(XXIV)

wherein $R_1$ and $R_2$ have the above meanings.

The starting materials can also be present in the form of optical antipodes.

The new compounds can be used as medicaments, for example in the form of pharmaceutical preparations, in which they or their salts are present as a mixture with a pharmaceutical, organic or inorganic, solid or liquid excipient which is suitable, for example, for enteral or parenteral administration. Possible substances for forming the excipient are those which do not react with the new compounds such as, for example, water, gelatine, lactose, starch, magnesium stearate, talc, vegetable oils, benzyl alcohols, gum, polyalkylene glycols, white petroleum jelly, cholesterol or other known medicinal excipients. The pharmaceutical preparations can be in the form of, for example, tablets, dragees, capsules, suppositories, ointments or creams or in a liquid form, as solutions (for example as an elixir or syrup), suspensions or emulsions. They are optionally sterilised and/or contain auxiliaries, such as preservatives, stabilisers, wetting agents or emulsifiers, salts for regulating the osmotic pressure or buffers. They can also contain yet other therapeutically valuable materials. The preparations, which can also be used in veterinary medicine, are formulated according to customary methods.

The daily dose is about 40–150 mg in the case of a warm-blooded animal of about 75 kg body weight.

The examples which follow illustrate the invention without however limiting it.

EXAMPLE 1

39.7 g of 5-bromo-3-morpholinyl-2-(3′-bromo-2′-hydroxy-propoxy)-pyrazine and 41 g of isopropylamine in 500 ml of methanol are heated to the reflux temperature for 15 hours. The reaction mixture is then evaporated in a waterpump vacuum. The residue is partitioned between 2 N hydrochloric acid and ether. The aqueous phase is rendered alkaline with concentrated sodium hydroxide solution and extracted by shaking with ether. The combined ether extracts are dried over sodium sulphate and evaporated in a waterpump vacuum. The crude base is thus obtained, and gives, with ethereal hydrochloric acid, in methanol, 5-bromo-3-morpholinyl-2-(3′-isopropylamino-2′-hydroxypropoxy)-pyrazine hydrochloride, melting point 202°–203° C.

5-Bromo-3-morpholinyl-2-(3′-bromo-2′-hydroxy-propoxy)-pyrazine, used as the starting material, can be prepared as follows:

(1a) 149 g of 2,3-dichloropyrazine, 300 g of morpholine and 400 ml of water are stirred for 16 hours at 40° C. The reaction mixture is then extracted by shaking with ether. The ether extracts are washed with water until neutral, dried over sodium sulphate and evaporated in a waterpump vacuum. The residue is distilled in a waterpump vacuum. 2-Chloro-3-morpholinyl-pyrazine, boiling point 162°–165° C./15 mm Hg, is thus obtained.

(1b) 120 g of 2-chloro-3-morpholinyl-pyrazine and 70 g of allyl alcohol are dissolved in 640 ml of hexamethyl-phosphoric acid triamide. 28.8 g of sodium hydride are introduced into this solution over the course of 30 minutes at 0° C. The mixture is then stirred for a further hour at 0° C. and thereafter for 1 hour at 30° C. and 15 hours at room temperature, until the reaction has subsided. The reaction mixture is then poured out onto 2 liters of ice water. After the excess sodium hydride present has been decomposed, the mixture is extracted by shaking with ether. The ether extracts are washed with water until neutral, dried over sodium sulphate and evaporated in a waterpump vacuum. The residue is distilled in a high vacuum. 2-Allyloxy-3-morpholinyl-pyrazine, boiling point 105°–106° C./0.03 mm Hg, is thus obtained.

(1c) 32 g of 2-allyloxy-3-morpholinyl-pyrazine are dissolved in 350 ml of dimethylsulphoxide and 2.7 ml of water. 52 g of N-bromosuccinimide are introduced into this solution over the course of 30 minutes, whilst stirring. In the course thereof, the reaction temperature rises to 35° C. The reaction mixture is stirred for a further 30 minutes, then diluted with approx. 500 ml of water and extracted by shaking with ether. The ether extracts are washed with water, dried over sodium sulphate and evaporated in a waterpump vacuum. 5-Bromo-3-morpholinyl-2-(3′-bromo-2′-hydroxy-propoxy)-pyrazine is thus obtained.

EXAMPLE 2

71 g of 5-bromo-3-dimethylamino-2-(3′-bromo-2′-hydroxy-propoxy)-pyrazine and 71 g of isopropylamine in 1 liter of methanol are boiled for 15 hours under reflux. The reaction mixture is then evaporated in a waterpump vacuum. The residue is partitioned between 2 N hydrochloric acid and ether. The aqueous phase is rendered alkaline with concentrated sodium hydroxide solution and extracted by shaking with ether. The combined ether extracts are dried over sodium sulphate and evaporated in a waterpump vacuum. The crude base is thus obtained, which with fumaric acid in methanol/ether gives 5-bromo-3-dimethylamino-2-(3′-isopropylamino-2′-hydroxy)-pyrazine hydrogen fumarate, melting point 146°–147° C.

5-Bromo-3-dimethylamino-2-(3′-bromo-2′-hydroxy-propoxy)-pyrazine, used as the starting material, can be prepared as follows:

(2a) 74 g of 2,3-dichloro-pyrazine are added dropwise over the course of 15 minutes, whilst stirring, to 350 ml of a 40% strength aqueous solution of dimethylamine. Whilst doing so, the reaction temperature is kept at 30° C. by cooling. When the exothermic reaction has subsided the mixture is stirred for a further 15 hours at room temperature. The reaction mixture is then extracted by shaking with ether. The ether extracts are washed with water until neutral, dried over sodium sulphate and evaporated in a waterpump vacuum. The residue is distilled in a waterpump vacuum. 2-Chloro-3-dimethylamino-pyrazine, boiling point 100°–102° C./10 mm Hg, is thus obtained.

(2b) 47 g of 2-chloro-3-dimethylamino-pyrazine and 35 g of allyl alcohol are dissolved in 300 ml of hexamethylphosphoric acid triamide. 14.4 g of sodium hydride are introduced into this solution at 0° C. over the course of 30 minutes. The mixture is then stirred for a further hour at 0° C. and for 15 hours at room temperature. The reaction mixture is then poured into 2 liters of ice water. After excess sodium hydride has been decomposed, the mixture is extracted by shaking with ether. The ether extracts are washed with water until neutral, dried over sodium sulphate and evaporated in a waterpump vacuum. The residue is distilled under reduced pressure. 2-Allyloxy-3-dimethylamino-pyrazine, boiling point 110°–115° C./10 mm Hg, is thus obtained.

(2c) 45 g of 2-allyloxy-3-dimethylamino-pyrazine are dissolved in 600 ml of dimethylsulphoxide and 9 ml of water. 89 g of N-bromosuccinimide are introduced into this solution over the course of 30 minutes, whilst stirring. At the same time the temperature is kept at 35° C. by external cooling. The mixture is then stirred for a further hour at room temperature and is thereafter diluted with 2 liters of ice water and extracted by shaking with ether. The ether extracts are washed with water, dried over sodium sulphate and evaporated in a waterpump vacuum. 5-Bromo-3-dimethylamino-2-(3'-bromo-2'-hydroxy-propoxy)-pyrazine is thus obtained.

EXAMPLE 3

7.5 g of 5-bromo-3-morpholinyl-2-(3'-isopropylamino-2'-hydroxy-propoxy)-pyrazine are dissolved in 80 ml of methanol and hydrogenated in the presence of 0.4 g of palladium on charcoal (5% strength) at 20°–30° C. under normal pressure. After 10 minutes, the reaction is complete and the calculated amount of hydrogen has been taken up. The catalyst is then filtered off and the filtrate is evaporated in a waterpump vacuum. The residue is partitioned between water and ether. The aqueous phase is rendered alkaline with concentrated sodium hydroxide solution and extracted by shaking with ether. The ether extracts are washed with water, dried over sodium sulphate and evaporated in a waterpump vacuum. 3-Morpholinyl-2-(3'-isopropylamino-2'-hydroxy-propoxy)-pyrazine, melting point 74°–76° C., is thus obtained.

The hydrochloride prepared therefrom crystallises from methanol-acetone, melting point 136°–137° C.

EXAMPLE 4

Analogously to the description in Example 3, 6.7 g of 5-bromo-3-dimethylamino-2-(3'-isopropylamino-2'-hydroxy-propoxy)-pyrazine give 3-dimethylamino-2-(3'-isopropylamino-2'-hydroxy-propoxy)-pyrazine hydrochloride, melting point 130–131° C.

EXAMPLE 5

53 g of 2-(3'-bromo-2'-hydroxy-propoxy)-3-chloropyrazine and 59 g of isopropylamine in 500 ml of methanol are boiled for 15 hours under reflux. The reaction mixture is then evaporated in a waterpump vacuum. The residue is partitioned between 2 N hydrochloric acid and ether. The hydrochloric acid phase is rendered alkaline with concentrated sodium hydroxide solution and extracted by shaking with ether. The ether extracts are washed with water, dried over sodium sulphate and evaporated in a waterpump vacuum. The residue crystallises from ether. 3-Chloro-2-(3'-isopropylamino-2'-hydroxy-propoxy)-pyrazine, melting point 99°–100° C., is thus obtained.

The hydrochloride prepared therefrom crystallises from methanol-ether, melting point 183° C.

2-(3'-Bromo-2'-hydroxy-propoxy)-3-chloro-pyrazine used as the starting material, can be prepared as follows:

(5a) 59.6 g of 2,3-dichloropyrazine and 92.8 g of allyl alcohol are dissolved in 400 ml of dimethylsulphoxide. 9.6 g of sodium hydride are introduced into this solution over the course of 30 minutes at 0°–5° C., whilst stirring. The mixture is then stirred for 15 hours at room temperature. Thereafter the reaction mixture is poured into 2 liters of ice water and extracted by shaking with ether. The ether extracts are washed with water, dried over sodium sulphate and evaporated in a waterpump vacuum. The residue is distilled in a high vacuum. 2-Allyloxy-3-chloro-pyrazine, boiling point 42°–44° C./0.03 mm Hg, is thus obtained.

(5b) 34 g of 2-allyloxy-3-chloro-pyrazine and 7.2 ml of water are dissolved in 500 ml of dimethylsulphoxide. 71 g of N-bromosuccinimide are introduced over the course of 30 minutes whilst stirring and keeping the reaction temperature at 30° C. by cooling. Thereafter the mixture is stirred for a further 30 minutes at room temperature and is then diluted with 1 liter of water. The reaction mixture is then extracted by shaking with ether. The ether extracts are washed with water, dried over sodium sulphate and evaporated in a waterpump vacuum. Crude 2-(3'-bromo-2'-hydroxy-propoxy)-3-chloro-pyrazine is thus obtained.

EXAMPLE 6

Analogously to Example 1, 39.7 g of 5-bromo-3-morpholinyl-2-(3'-bromo-2'-hydroxy-propoxy)-pyrazine and 51 g of tert.-butylamine give 5-bromo-3-morpholinyl-2-(3'-tert.-butylamino-2'-hydroxy-propoxy)-pyrazine, melting point 104°–105° C.

EXAMPLE 7

Analogously to Example 3, 3.9 g of 5-bromo-3-morpholinyl-2-(3'-tert.-butylamino-2'-hydroxy-propoxy)-pyrazine give 3-morpholinyl-2-(3'-tert.-butylamino-2'-hydroxy-propoxy)-pyrazine hydrochloride, melting point 175°–176° C.

EXAMPLE 8

7.5 g of 3-chloro-2-(3'-isopropylamino-2'-hydroxy-propoxy)-pyrazine and 3.2 g of sodium methylate in 150 ml of methanol are boiled for 10 hours under reflux. The reaction mixture is then evaporated in a waterpump vacuum. The residue is partitioned between 2 N hydrochloric acid and ether. The acid aqueous phase is rendered alkaline with concentrated sodium hydroxide solution and extracted by shaking with ether. The ether extracts are washed with water, dried over sodium sulphate and evaporated in a waterpump vacuum. The crude base is thus obtained, from which 3-methoxy-2-(3'-isopropylamino-2'-hydroxy-propoxy)-pyrazine hydrochloride, melting point 152°–153° C., is obtained by reaction with ethereal hydrochloric acid in methanol.

EXAMPLE 9

Analogously to the description in Example 1, 37 g of 5-bromo-3-isopropylamino-2-(3'-bromo-2'-hydroxy-1-propoxy)-pyrazine give 5-bromo-3-isopropylamino-2-(3'-isopropylamino-2'-hydroxy-1-propoxy)-pyrazine, melting point 108°–109° C. when crystallised from ether.

5-Bromo-3-isopropylamino-2-(3'-bromo-2'-hydroxy-propoxy)-pyrazine used as the starting material, can be prepared analogously to the description in Example 1, as follows:

(9a) 149 g (1.0 mol) of 2,3-dichloro-pyrazine and 1.4 liters of an aqueous 40% strength solution of isopropylamine give 2-chloro-3-isopropylamino-pyrazine, boiling point 120° C.–121° C./12 mm Hg.

(9b) 86 g of 2-chloro-3-isopropylamino-pyrazine give 2-allyloxy-3-isopropylamino-pyrazine, boiling point 121°–123° C./12 mm Hg.

(9c) 39 g of 2-allyloxy-3-isopropylamino-pyrazine give 5-bromo-3-isopropylamino-2-(3'-bromo-2'-hydroxy-propoxy)-pyrazine.

EXAMPLE 10

Analogously to the description in Example 3, 7 g of 5-bromo-3-isopropylamino-2-(3'-isopropylamino-2'-hydroxy-propoxy)-pyrazine give 3-isopropylamino-2-(3'-isopropylamino-2'-hydroxy-propoxy)-pyrazine dihydrochloride, melting point 198°–200° C.

EXAMPLE 11

10.7 g of 2-chloro-3-morpholinyl-5-methyl-pyrazine and 16.6 g of 2-phenyl-3-isopropyl-5-hydroxymethyloxazolidine are dissolved in 130 ml of hexamethylphosphoric acid triamide. 3.6 g of a 50% strength suspension of sodium hydride in paraffin oil are introduced into this solution over the course of 30 minutes at 0°–5° C., whilst stirring. The mixture is then stirred for 1 hour at 0°–5° C. and 24 hours at room temperature. The reaction mixture is then poured onto 500 ml of ice water and extracted by shaking with ether. The ether extracts are washed with water and evaporated in a waterpump vacuum. The residue is taken up in 200 ml of 1 N sulphuric acid and the reaction mixture is stirred for 15 hours at room temperature and then extracted by shaking with ether. The acid aqueous phase is rendered alkaline with concentrated sodium hydroxide solution and is then extracted by shaking with ether. The ether extracts are washed with water, dried over sodium sulphate and evaporated in a waterpump vacuum. The residue crystallises from etherpentane. 2-(3'-Isopropylamino-2'-hydroxy-propoxy)-3-morpholinyl-5-methyl-pyrazine, melting point 77°–78° C., is thus obtained.

The hydrogen fumarate preferred therefrom, using fumaric acid, crystallises from methanol-ether, melting point 183°–184° C.

2-Chloro-3-morpholinyl-5-methyl-pyrazine, used as the starting material, can be prepared as follows:

16.3 g of 2,3-dichloro-5-methyl-pyrazine and 100 ml of morpholine are warmed to 100° C. for 6 hours. The reaction mixture is then diluted with 200 ml of ether and again extracted by shaking with water. The ether phase is dried over sodium sulphate and evaporated in a water-pump vacuum. The residue is distilled in a waterpump vacuum. 2-Chloro-3-morpholinyl-5-methyl-pyrazine, boiling point 166°–167° C./15 mm Hg, is thus obtained.

EXAMPLE 12

Analogously to the description in Example 3, 4.9 g of 3-chloro-2-(3'-isopropylamino-2'-hydroxy-propoxy)-pyrazine give 2-(3'-isopropylamino-2'-hydroxy-propoxy)-pyrazine. The fumarate prepared therefrom by means of fumaric acid crystallises from isopropanol, melting point 136°–137° C.

EXAMPLE 13

Analogously to the description in Example 11, 8.5 g of 2-chloro-3-allyloxy-pyrazine give 2-(3'-isopropylamino-2'-hydroxy-propoxy)-3-allyloxy-pyrazine.

The fumarate prepared therefrom by means of fumaric acid crystallises from methanol-acetone, melting point 149°–150° C.

EXAMPLE 14

20 g of isopropylamine are added to a solution of 15.0 g of 3-chloro-2-(2',3'-epoxy-propoxy)-pyridine in 100 ml of isopropanol and the mixture is then heated to the boil under reflux for 3 hours. The reaction mixture is evaporated in vacuo, the residue is dissolved in 300 ml of ethyl acetate and the solution is extracted with 100 ml of 2 N hydrochloric acid. The hydrochloric acid extract is rendered alkaline with 30 ml of concentrated sodium hydroxide solution and is extracted 3 times with 100 ml of ethyl acetate at a time. The organic phases are each washed with 10 ml of sodium chloride solution, combined and dried over magnesium sulphate. 2-(3'-Isopropylamino-2'-hydroxy-propoxy)-3-chloro-pyridine is thus obtained; it is recrystallised from ether-petroleum ether and then melts at 71°–73° C. The hydrochloride melts at 167°–169° C. (from methanol-acetone).

3-Chloro-2-(2',3'-epoxy-propoxy)-pyridine, used as the starting material, can be prepared as follows:

(14a) 108 g of 2,2-dimethyl-4-hydroxymethyldioxolane are added dropwise to a suspension of 16.5 g of sodium hydride in 600 ml of 1,2-dimethoxyethane in such a way that the reaction remains under control. The mixture is then stirred for 1 hour at a bath temperature of 50°–60° C. 100.0 g of 2,3-dichloropyridine are added in portions to the resulting jelly-like suspension, under reflux. The reaction mixture, which reverts to being less viscous, is stirred for a further 3 hours under reflux after completion of the addition. The solvent is evaporated off in vacuo and the residue is partitioned between 2 liters of ether and 200 ml of water. The ether phase is dried over magnesium sulphate. The product which remains after evaporating off the ether is distilled in a high vacuum. 3-Chloro-2-[2',2'-dimethyl-1',3'-dioxolanyl-(4')]-methoxy-pyridine boils at 95–100° C./0.01 mm Hg.

(14b) 320 ml of 2 N hydrochloric acid are added to a solution of 157 g of 3-chloro-2-[2',2'-dimethyl-1',3'-dioxolanyl-(4')]-methoxy-pyridine in 100 ml of ethanol and the mixture is stirred for 2 hours at room temperature. After evaporating off the ethanol, the product is dissolved in a minimum amount of water (approx. 100 ml), the solution is washed with 100 ml of ether and the aqueous phase is rendered alkaline with concentrated sodium hydroxide solution. The oil which separates out is extracted 3 times with 200 ml of ethyl acetate at a time. The extracts are each washed with 20 ml of sodium chloride solution, dried and evaporated. The resulting 3-chloro-2-(2',3'-dihydroxy-propoxy)-pyridine boils at 142°–145° C./0.015 mm Hg.

(14c) 25.2 g of methanesulphonic acid chloride are added dropwise over the course of 1 hour to a solution of 40.6 g of 3-chloro-2-(2',3'-dihydroxy-propoxy)-pyridine in 100 ml of pyridine whilst stirring and cooling at 0°–5° C. The reaction mixture is then stirred further for 5 hours at room temperature and is subsequently poured onto 200 ml of ice water. The oil which separates out is isolated as in Example (1b). Crude 3-chloro-2-(3'-methanesulphonyloxy-2'-hydroxy-propoxy)-pyridine is thus obtained and is converted further in the crude state.

(14d) 67 g of crude 3-chloro-2-(3'-methanesulphonyloxy-2'-hydroxy-propoxy)-pyridine, 400 ml of methylene chloride, 240 ml of 1 N sodium hydroxide solution and 5 g of tetrabutylammonium chloride are stirred for 15 hours at room temperature. The methylene chloride phase is separated off, washed twice with 40 ml of water at a time, dried and evaporated. 3-Chloro-2-(2',3'-epoxypropoxy)-pyridine is isolated as a light yellow oil from the evaporation residue by distillation at 115°-130° C./0.03 mm Hg.

EXAMPLE 15

22 g of crude 2-methoxy-3-(3'-methanesulphonyloxy-2'-hydroxy-propoxy)-pyridine, 50 ml of isopropylamine and 150 ml of isopropanol are heated for 16 hours under reflux. After working up analogously to Example 14, 3-(3'-isopropylamino-2'-hydroxypropoxy)-2-methoxy-pyridine is obtained, which melts at 50°-65° C. after recrystallisation from ether-pentane. After reaction with half the equivalent amount of fumaric acid, the neutral fumarate of melting point 146°-147° C. (recrystallised from acetone) is obtained.

2-Methoxy-3-(3'-methanesulphonyloxy-2'-hydroxy-propoxy)-pyridine, used as the starting material, is obtained as follows:

(15a) 26 g of 3-[1',3'-dioxolan-2'-on-yl-(4')]methoxy-2-nitro-pyridine are heated with a solution of 7.5 g of sodium in 500 ml of absolute methanol to the boil under reflux for 15 hours. The solution is cooled, neutralised with 2 N hydrochloric acid and evaporated in vacuo. The residue is boiled with 500 ml of chloroform and the solution is filtered and evaporated. The evaporation residue contains crude 3-(2',3'-dihydroxy-propoxy)-2-methoxy-pyridine as a yellowish oil.

(15b) 9.0 g of methanesulphonic acid chloride are added dropwise, whilst stirring, to 14.8 g of 3-(2',3'-dihydroxy-propoxy)-2-methoxy-pyridine dissolved in 100 ml of anhydrous pyridine, at −10° to −15° C. The reaction mixture is then stirred for a further 3 hours at −10° C. The pyridine is then evaporated off as completely as possible on a rotary evaporator at 10 mm Hg and the resulting crude 2-methoxy-3-(3'-methanesulphonyloxy-2'-hydroxy-propoxy)-pyridine is reacted with isopropylamine without having been purified further.

EXAMPLE 16

20 ml of 2 N hydrochloric acid are added to a solution of 6.5 g of 2-[3'-isopropyl-2'-phenyl-oxazolidinyl-(5')]-methoxy-6-methoxy-pyridine in 40 ml of ethyleneglycol dimethyl ether and 10 ml of ethanol and the mixture is stirred for 2 hours at room temperature. The solution is then evaporated in vacuo and the residue is partitioned between 30 ml of water and 50 ml of ether. The aqueous phase is rendered strongly alkaline with concentrated sodium hydroxide solution and is extracted 3 times with 100 ml of ethyl acetate at a time. After drying and evaporation, 2-(3'-isopropylamino-2'-hydroxy-propoxy)-6-methoxy-pyridine is obtained, of which the neutral fumarate melts at 140°-141° C. (when recrystallised from methanol/acetone).

EXAMPLE 17

7.4 g of 2-[3'-isopropyl-2'-phenyl-oxazolidinyl(5')]-methoxy-4-phenyl-pyridine are hydrolysed analogously to Example 16 and give 2-(3'-isopropylamino-2'-hydroxypropoxy)-4-phenyl-pyridine, of which the neutral fumarate melts at 171°-173° C. (recrystallisation from methanol/acetone).

EXAMPLE 18

6.8 g of crude 2-[3'-isopropyl-2'-phenyl-oxazolidinyl-(5')]-methoxy-5-nitropyridine are hydrolysed analogously to Example 16, the mixture is then brought to pH 9 with saturated sodium carbonate solution and the product is isolated further as in Example 16. 2-(3'-Isopropylamino-2'-hydroxy-propoxy)-5-nitro-pyridine of melting point 117°-123° C. (when recrystallised from isopropanol) is thus obtained.

EXAMPLE 19

33 g of crude 3-(2',3'-epoxy-propoxy)-6-methylpryidine, 350 ml of isopropanol and 75 ml of isopropylamine are heated to the boil under reflux for 12 to 14 hours. The mixture is worked up analogously to Example 14. 3-(3'-Isopropylamino-2'-hydroxy-propoxy)-6-methyl-pyridine, thus obtained boils at 135°-150° C./0.2 mm Hg in a bulb tube. Its neutral fumarate melts at 171°-173° C. (when recrystallised from methanol/acetone).

3-(2',3'-Epoxy-propoxy)-6-methyl-pyridine, required as the starting material, is prepared as follows:

(19a) 22 g of 6-methyl-3-pyridinol, 50 g of potassium carbonate and 80 ml of epichlorohydrin in 500 ml of acetone are heated to the boil under reflux for 18 to 20 hours, whilst stirring. The undissolved constituents are filtered off and the filtrate is evaporated at 30 to 40° C. bath temperature in vacuo. 3-(2',3'-Epoxy-propoxy)-6-methyl-pyridine, thus obtained, is processed further without additional purification.

EXAMPLE 20

(a) 4.9 g of 5-hydroxy-methyl-3-isopropyl-2-phenyloxazolidine are added to a suspension of 0.5 g of sodium hydride in 40 ml of ethylene glycol dimethyl ether. The reaction mixture is stirred for 2 hours at 40°-50° C., 2.9 g of 2-chloro-6-methoxypyridine are then added and the mixture is heated for 14 hours under reflux. The solution of 2-[3'-isopropyl-2'-phenyl-oxazolidinyl-(5')]-methoxy-6-methoxy-pyridine, thus obtained, can be hydrolysed as indicated in Example 16 without isolating the product. The following compounds can also be prepared analogously to the above description:

(b) 2-[3'-Isopropyl-2'-phenyl-oxazolidinyl-(5')]-methoxy-4-phenyl-pyridine from 2-bromo-4-phenyl-pyridine.

(c) 2-[3'-Isopropyl-2'-phenyl-oxazolidinyl-(5')]-methoxy-5-nitropyridine from 2-chloro-5-nitro-pyridine.

(d) 2-[3'-Isopropyl-2'-phenyl-oxazolidinyl-(5')]-methoxy-3-methyl-pyridine from 2-chloro-3-methyl-pyridine.

(e) 2-[3'-Isopropyl-2'-phenyl-oxazolidinyl-(5')]-methoxy-5-methylaminocarbonyl-pyridine from 6-chloro-N-methylnicotinic acid amide.

The starting material for Example (20e) can be prepared as follows:

42 g of 6-hydroxynicotinic acid are introduced over the course of 1 hour into a suspension of 126 g of phosphorus pentachloride in 300 ml of toluene. The reaction mixture is heated to the boil for 3 hours and is then evaporated under reduced pressure. The crude crystalline evaporation residue is dissolved in 200 ml of chloroform and added dropwise to 300 ml of a 16% strength solution of methylamine in absolute ethanol, whilst cooling with ice. After the addition, the reaction mixture is stirred for a further 3 hours and is then filtered and evaporated under reduced pressure. The evaporation residue is dissolved in ethyl acetate, the solution is washed with 2 N sodium carbonate solution and the product is recrystallised from ethanol-ether. 6-Chloro-N-methylnicotinic acid amide, thus isolated, melts at 149°–151° C.

EXAMPLE 21

40 of crude 2-[3'-isopropyl-2'-phenyloxazolidinyl-(5')]-methoxy-3-methylpyridine, dissolved in 150 ml of ethanol, are hydrolysed with 30 ml of 6 N hydrochloric acid for 3 hours at 20° C. and the product is worked up analogously to Example 16. 2-(3'-Isopropylamino-2'-hydroxy-propoxy)-3-methylpyridine is thus obtained, which distils in a bulb tube at 130°–140° C./0.03 mm Hg, and of which the fumarate melts at 153°–155° C. (when recrystallised from methanol-acetone).

EXAMPLE 22

22 g of 2-[3'-isopropyl-2'-phenyl-oxazolidinyl(5')]-methoxy-5-methyl-aminocarbonyl-pyridine are dissolved in 200 ml of ethanol and hydrolysed with 30 ml of 6 N hydrochloric acid for 3–4 hours at 20° C., and the product is worked up analogously to Example 16. 2-(3'-Isopropylamino-2'-hydroxy-propoxy)-5-methylaminocarbonyl-pyridine of melting point 118–120° C. is thus obtained.

EXAMPLE 23

25 g of crude 3-(2',3'-epoxy-propoxy)-2-pyrrolidinocarbonyl-pyridine, dissolved in 350 ml of isopropanol, are boiled with 150 ml of isopropylamine for 3 hours under reflux. After evaporating the mixture and working up the residue analogously to Example 14, 3-(3'-isopropylamino-2'-hydroxy-propoxy)-2-pyrrolidinocarbonylpyridine, melting at 108°–111° C. (when recrystallised from ethyl acetate-ether) is obtained.

The starting material is obtained by reaction of 2-pyrrolidinocarbonyl-3-hydroxypyridine with epichlorohydrin analogously to Example (19a).

EXAMPLE 24

4.2 g of sodium hydride dispersion (55% strength) are initially introduced into 150 ml of dimethoxyethane and a solution of 24.3 g of 2-phenyl-3-isopropyl-5-hydroxymethyl-oxazolidine in 50 ml of dimethoxyethane is added dropwise whilst stirring and passing nitrogen into the mixture. The whole is stirred for 1.5 hours at 45° C. After addition of 19.96 g of 3-chloro-6-morpholinopyridazine, the reaction mixture is heated under reflux for 24 hours and is then acidified with hydrochloric acid (15% strength) at 20° C. and stirred well for 2 hours. The dimethoxyethane is evaporated off in vacuo at 40° C. and the residue containing hydrochloric acid is extracted with ether. The acid phase is rendered alkaline with 5 N sodium hydroxide solution and extracted with chloroform. The extract is washed with saturated sodium chloride solution, filtered through cottonwool and evaporated in vacuo, and the residue is purified by chromatography on silica gel (eluant: chloroform/methanol = 9/1).

After recrystallisation from methylene chloride/ether, the 3-(3'-isopropylamino-2'-hydroxy-propoxy)-6-morpholino-pyridazine obtained melts at 112°–113° C.

EXAMPLE 25

12.5 g of 2-[3'-isopropyl-2'-phenyl-oxazolidinyl(5')]-methoxy-pyrimidine are taken up in 60 ml of 1 N sulphuric acid. The mixture is heated to the boil for half an hour and cooled, the benzaldehyde which has separated out is extracted with ether and the water phase is separated off, mixed with the amount of barium hydroxide solution required to neutralise the sulphuric acid, and filtered. The filtrate is evaporated in vacuo. The resulting oil is distilled in a bulb tube. After a small amount of first runnings, 2-(3'-isopropylamino-2'-hydroxy-propoxy)-pyrimidine is obtained at 140° C./0.05 mm Hg as a colourless oily distillate. Its hydrogen oxalate melts at 181°–182° C. (from acetone).

EXAMPLE 26

13.3 g of 2-(3'-p-toluenesulphonyloxy-2'-hydroxy-propoxy)-pyrimidine are dissolved in 100 ml of isopropanol and 22 ml of isopropylamine and kept for 48 hours at room temperature. The volatile constituents are then distilled off in vacuo, the oily residue is taken up in acetone and a solution of 4 g of oxalic acid in acetone is added. 2-(3'-Isopropylamino-2'-hydroxy-propoxy)-pyrimidine hydrogen oxalate is obtained and is recrystallised from methanol-acetone. Melting point 181°–182° C.

2-(3'-p-Toluenesulphonyloxy-2'-hydroxy-propoxy)-pyrimidine, required as the starting material, can be prepared as follows:

(26a) 6.6 g of 2,2-dimethyl-1,3-dioxolane-4-methanol are added to a suspension of 1.2 g of sodium hydride in 50 ml of dimethoxyethane and the mixture is stirred for 2 hours at room temperature. 5.7 g of 2-chloropyrimidine are then added. The reaction mixture is heated to the boil for 2 hours and is then evaporated in vacuo. The residue is distilled in a bulb tube. After a small amount of first runnings, 2-[2',2'-dimethyl-1',3'-dioxolane-(4')]-methoxy-pyrimidine distils as a colourless oil at 200° C./19 mm Hg.

(25b) 16 g of 2-[2',2'-dimethyl-1',3'-dioxolane(4')]-methoxy-pyrimidine, 20 ml of water and 2 ml of 2 N sulphuric acid are heated to the boil for 15 minutes. The mixture is then cooled, the amount of barium hydroxide solution required to neutralise the acid is added, and the whole is filtered. The filtrate is evaporated and the oil which remains is distilled in a bulb tube, whereupon 2-(2',3'-dihydroxy-propoxy)-pyrimidine is obtained as a colourless oily distillate at 180°–190° C./0.4 mm Hg.

(25c) 13.6 g of p-toluenesulphonyl chloride are introduced over the course of 15 minutes, whilst stirring, into a solution of 11.8 g of 2-(2',3'-dihydroxy-propoxy)-pyrimidine in 18 ml of pyridine which is cooled to −10° C. The reaction mixture is kept at 0° C. for 15 hours. Ice is then added followed by 20 ml of 6 N hydrochloric acid introduced whilst stirring. The mixture is then twice extracted with 150 ml of methylene chloride at a time. The extracts are washed with sodium bicarbonate solution, dried over sodium sulphate and evaporated. 2-(3'-p-Toluenesulphonyloxy-2'-hydroxy-propoxy)-pyrimidine is obtained as a yellowish oil.

EXAMPLE 27

The following compounds can be prepared analogously to the description in Examples 1–13:

(1) 2-(3'-Isopropylamino-2'-hydroxy-propoxy)-3-morpholino-5-(2'-methoxyethyl)-pyrazine,
(2) 2-(3'-isopropylamino-2'-hydroxy-propoxy)-3-morpholino-5-(2'-methoxycarbonylaminoethyl)-pyrazine,
(3) 2-(3'-isopropylamino-2'-hydroxy-propoxy)-5-hydroxy-pyrazine.

EXAMPLE 28

The following compounds can also be prepared analogously to the description in Examples 14 to 23:
(a) 3-(3'-Isopropylamino-2'-hydroxy-propoxy)-2-(n-butylaminocarbonyl)-pyridine, melting point 65–67° C.,
(b) 2-(3'-isopropylamino-2'-hydroxy-propoxy)-3-propyl-pyridine,
(c) 2-(3'-isopropylamino-2'-hydroxy-propoxy)-3-nitropyridine,
(d) 3-dimethylamino-2-(3'-isopropylamino-2'-hydroxy-propoxy)-pyridine,
(e) 2-(3'-isopropylamino-2'-hydroxy-propoxy)-5-methoxypyridine,
(f) 2-(3'-isopropylamino-2'-hydroxy-propoxy)-5-(2'-methoxyethyl)-pyridine,
(g) 5-acetylaminomethyl-2-(3'-isopropylamino-2'-hydroxy-propoxy)-pyridine,
(h) 2-chloro-3-(3'-isopropylamino-2'-hydroxy-propoxy)-pyridine,
(i) 2-(3'-isopropylamine-2'-hydroxy-propoxy)-3,5-dimethyl-pyridine,
(j) 2-(3'-isopropylamino-2'-hydroxy-propoxy)-3-chloro-5-(2'-methoxyethyl)-pyridine,
(k) 2-(3'-isopropylamino-2'-hydroxy-propoxy)-5-carbonylmethyl-pyridine,
(l) 2-(3'-isopropylamino-2'-hydroxy-propoxy)-3-allyloxypyridine,
(m) 3-(3'-isopropylamino-2'-hydroxy-propoxy)-6-hydroxy-pyridine,
(n) 2-(3'-isopropylamino-2'-hydroxy-propoxy)-5-hydroxypyridine.

EXAMPLE 29

The following compounds can also be synthesised analogously to the description in Examples 24–26:
(1) 2-(3'-Isopropylamino-2'-hydroxy-propoxy)-4-acetylamino-5-cyano-pyrimidine,
(2) 2-(3'-isopropylamino-2'-hydroxy-propoxy)-5-(2'-methoxycarbonylaminoethyl)-pyrimidine,
(3) 2-(3'-isopropylamino-2'-hydroxy-propoxy)-6-methyl-pyrimidine,
(4) 2-(3'-isopropylamino-2'-hydroxy-propoxy)-5-phenyl-pyrimidine,
(5) 3-(3'-isopropylamino-2'-hydroxy-propoxy)-6-methoxy-pyridazine, melting point 115°–116° C.,
(6) 3-(3'-isopropylamino-2'-hydroxy-propoxy)-6-chloro-pyridazine, melting point 98°–99° C.,
(7) 3-(3'-isopropylamino-2'-hydroxy-propoxy)-pyridazine, melting point 91°–93° C.

EXAMPLE 30

Tablets contanining 50 mg of active substance are prepared in the usual manner to have the following composition:

| Composition | |
|---|---|
| 2-(3'-Tert.-butylamino-2'-hydroxy-propoxy)-3-morpholinopyrazine | 50 mg |
| Wheat starch | 59 mg |
| Lactose | 70 mg |
| Colloidal silica | 10 mg |
| Talc | 10 mg |
| Magnesium stearate | 1 mg |
| | 200 mg |

Preparation

The 2-(3'-tert.-butylamino-2'-hydroxy-propoxy)-3-morpholinopyrazine is mixed with a part of the wheat starch, with lactose and with colloidal silica and the mixture is forced through a sieve, giving a powder mixture. A further part of the wheat starch is worked into a paste with a five-fold amount of water on a waterbath and the powder mixture is kneaded with this paste until a slightly plastic mass has been produced.

The plastic mass is forced through a sieve of about 3 mm mesh width and dried and the resulting dry granules are again forced through a sieve. The residual wheat starch, talc and magnesium stearate are then mixed in and the mixture is pressed to give tablets weighing 200 mg and having a breaking groove.

The daily dose is about ½ to 4 tables in the case of a warm-blooded animal of about 75 kg body weight, but it is also possible to administer the corresponding dose of active compound in a single tablet of appropriate composition.

EXAMPLE 31

60 ml of 4 N hydrochloric acid are added to a solution of 34 g of 2-[3'-isopropyl-2'-phenyl-oxazolidinyl(5')]-methoxy-4-methyl-pyridine in 200 ml of ethanol and the mixture is left to stand overnight at room temperature. The solvent is evaporated off in vacuo and the residue is dissolved in approx. 200 ml of water. This solution is extracted with 100 ml of ether. The aqueous phase is separated off, rendered strongly alkaline with concentrated potassium hydroxide solution and extracted with methylene chloride. After drying the extract and evaporating the solvent, a dark oil is obtained, which is distilled in a bulb tube at 120°–130° C./0.1 mm Hg. 2-(3'-Isopropylamino-2'-hydroxy-propoxy)-4-methyl-pyridine thus obtained, is mixed with half the equivalent amount of fumaric acid, dissolved in methanol, the solution is evaporated in vacuo and acetone is added to the residue. The neutral fumarate of melting point 136°–139° C. hereupon crystallises.

EXAMPLE 32

60 ml of 4 N hydrochloric acid are added to a solution of 40 g of 2-[3'-isopropyl-2'-phenyl-oxazolidinyl(5')]-methoxy-5-methyl-pyridine in 200 ml of ethanol and the mixture is left to stand overnight at room temperature. The solvent is evaporated off in vacuo and the residue is dissolved in approx. 200 ml of water. This solution is extracted with 100 ml of ether. The aqueous phase is separated off, rendered strongly alkaline with concentrated potassium hydroxide solution and extracted with methylene chloride. After drying the extract and evaporating off the solvent, a dark oil is obtained, which is distilled in a bulb tube at 120°–130° C./0.1 mm Hg. 2-(3'-Isopropylamino-2'-hydroxy-propoxy)-5-methyl-pyridine thus obtained, crystallises: Melting point 62°–67° C. Half the equivalent amount of fumaric acid, dissolved in methanol, is added, the solution is evaporated in vacuo and acetone is added to the residue. The neutral fumarate of melting point 149°–151° C. hereupon crystallises.

EXAMPLE 33

60 ml of 4 N hydrochloric acid are added to a solution of 35 g of 2-[3'-isopropyl-2'-phenyl-oxazolidinyl-(5')]-methoxy-6-methyl-pyridine in 200 ml of ethanol and the mixture is left to stand for 1 hour at room temperature. The solvent is evaporated off in vacuo and the residue is dissolved in approx. 200 ml of water. This solution is extracted with 100 ml of ether. The aqueous phase is separated off, rendered strongly alkaline with concentrated potassium hydroxide solution and extracted with methylene chloride. After drying the extract and evaporating off the solvent, a dark oil is obtained, which is distilled in a bulb tube at 130° C./0.04 mm Hg. Half the equivalent amount of fumaric acid, dissolved in methanol, is added to the 2-(3'-isopropylamino-2'-hydroxy-propoxy)-6-methylpyridine thus obtained, the solution is evaporated in vacuo and acetone is added to the residue. Hereupon, the neutral fumarate of melting point 164°–165° C. crystallises.

EXAMPLE 34

60 ml of 4 N hydrochloric acid are added to a solution of 40 g of 2-[3'-isopropyl-2'-phenyl-oxazolidinyl(5')]-methoxy-3-ethoxy-pyridine in 200 ml of ethanol and the mixture is left to stand overnight at room temperature. The solvent is evaporated off in vacuo and the residue is dissolved in approx. 200 ml of water. This solution is extracted with 100 ml of ether. The aqueous phase is separated off, rendered strongly alkaline with concentrated potassium hydroxide solution and extracted with ethyl acetate. After drying the extract and evaporating off the solvent, a dark oil is obtained, which is distilled in a bulb tube at 130°–140° C./0.03 mm Hg. Half the equivalent amount of fumaric acid, dissolved in methanol, is added to the 2-(3'-isopropylamino-2'-hydroxy-propoxy)-3-ethoxypyridine thus obtained, the solution is evaporated in vacuo and methyl ethyl ketone is added to the residue. Hereupon, the neutral fumarate of melting point 142°–144° C. crystallises.

EXAMPLE 35

A solution of 30 g of 2-[3'-isopropyl-2'-phenyloxazolidinyl-(5')]-methoxy-3-chloro-5-(methylaminocarbonyl)-pyridine in 260 ml of 2 N sulphuric acid is stirred for 4 hours at room temperature. This solution is extracted with 100 ml of ether. The aqueous phase is separated off, rendered strongly alkaline with concentrated potassium hydroxide solution and extracted with ethyl acetate. After drying the extract and evaporating off the solvent, a dark oil is obtained, which crystallises from ether. 2-(3'-Isopropylamino-2'-hydroxy-propoxy)-3-chloro-5-(methylaminocarbonyl)-pyridine, thus obtained, melts at 130°–132° C. Half the equivalent amount of fumaric acid, dissolved in methanol, is added, the solution is evaporated in vacuo and acetone is added to the residue. Hereupon, the neutral fumarate of melting point 133°–136° C. crystallises.

EXAMPLE 36

A solution of 32 g of 2-[3'-isopropyl-2'-phenyloxazolidinyl-(5')]-methoxy-3-chloro-5-n-hexylaminocarbonylpyridine in 260 ml of 2 N sulphuric acid is stirred for 4 hours at room temperature. This solution is extracted with 100 ml of ether. The aqueous phase is separated off, rendered strongly alkaline with concentrated potassium hydroxide solution and extracted with ethyl acetate. After drying the extract and evaporating the solvent, a dark oil is obtained, which crystallises from ether. 2-(3'-Isopropylamino-2'-hydroxy-propoxy-3-chloro-5-n-hexylaminocarbonylpyridine, thus obtained, melts at 131°–132° C. Half the equivalent amount of fumaric acid, dissolved in methanol, is added thereto, the solution is evaporated in vacuo and acetone is added to the residue. Hereupon, the neutral fumarate of melting point 170°–172° C. crystallises.

EXAMPLE 37

A solution of 28 g of 2-[3'-isopropyl-2'-phenyloxazolidinyl-(5')]-methoxy-5-cyano-pyridine in 260 ml of 2 N sulphuric acid is left to stand for 4 hours at room temperature. This solution is extracted with 100 ml of ether. The aqueous phase is separated off, rendered strongly alkaline with concentrated potassium hydroxide solution and extracted with methylene chloride. After drying the extract and evaporating off the solvent, a dark oil is obtained, which crystallises from methylene chloride-ether. 2-(3'-Isopropylamino-2'-hydroxy-propoxy)-5-cyanopyridine thus obtained melts at 124°–126° C.

EXAMPLE 38

12.5 g of 2-(3'-isopropylamino-2'-hydroxy-propoxy)-5-cyano-pyridine are dissolved in 100 ml of methanol. 5–7 g of ammonia are added to the solution and after adding 3 g of Raney nickel hydrogenation is carried out at 70°–80° C. and 40 bars initial pressure of hydrogen, until the absorption of hydrogen ceases. The catalyst is filtered off, the solution is evaporated and the residue is distilled in a bulb tube at 140° C./0.01 mm Hg. 5-Aminomethyl-2-(3'-isopropylamino-2'-hydroxy-propoxy)-pyridine is thus obtained as a slightly yellowish oil.

EXAMPLE 39

28.7 g of 2-(3'-isopropylamino-2'-hydroxy-propoxy)-5-nitro-pyridine are dissolved in 300 ml of methanol and hydrogenated, with addition of 3 g of Raney nickel, at room temperature and atmospheric pressure until the theoretical amount of hydrogen has been absorbed. The catalyst is filtered off under nitrogen and the filtrate is evaporated. The crude 5-amino-2-(3'-isopropylamino-2'-hydroxy-propoxy)-pyridine thus obtained is dissolved in 150 ml of dichloromethane and 14.3 ml of acetic anhydride are added dropwise whilst stirring. In the course thereof, the temperature of the solution rises to the refluxing temperature. After the dropwise addition of the anhydride, the reaction mixture is stirred for a further 20–30 minutes. After extracting the solution by shaking with 90 ml of 2 N sodium carbonate solution, the organic phase is extracted with a total of 200 ml of 2 N hydrochloric acid and the acid aqueous extract is treated with active charcoal (approx. 10 g) and evaporated in vacuo. The resulting dark oil is dissolved in the minimum amount of water required and the solution is rendered alkaline with concentrated sodium hydroxide solution. The crude base is isolated by extraction with dichloromethane. 5-Acetamido-2-(3'-isopropylamino-2'-hydroxy-propoxy)-pyridine of melting point 138°–141° C. crystallises from butanone. It forms a hydrochloride of melting point 204°–206° C. (from methanolacetone).

EXAMPLE 40

A solution of 25 g of crude 2-[3'-isopropyl-2'-phenyl-oxazolidinyl-(5')]-methoxy-5-(2'-aminoethyl)-pyridine in 150 ml of 4 N sulphuric acid is reacted analogously to Example 35 and worked up. This gives crude 5-(2'-aminoethyl)-2-(3'-isopropylamino-2'-hydroxypropoxy)-pyridine of sufficient purity for further reactions. Pure product is obtained by distillation in a bulb tube at 140°–150° C./0.005 mm Hg.

EXAMPLE 41

5.4 ml of chloroformic acid methyl ester are added dropwise, whilst stirring, to 12.4 g of 5-(2'-aminoethyl)-2-(3'-isopropylamino-2'-hydroxy-propoxy)-pyridine, dissolved in a mixture of 45 ml of isopropanol and 45 ml of water, at a temperature of 20°–35° C., with cooling by means of ice water, if necessary. The reaction mixture is stirred further for one hour at room temperature and is evaporated in vacuo, and the evaporation residue is dissolved in approx. 30 ml of water. This solution is extracted with 20 ml of ethyl acetate and the acid aqueous phase is rendered alkaline with concentrated sodium hydroxide solution. The oil which precipitates is extracted with dichloromethane. After drying the solution over magnesium sulphate and evaporating off the solvent, 2-(3'-isopropylamino-2'-hydroxy-propoxy)-5-(2'-methoxycarbonylaminoethyl)-pyridine is obtained, melting at 97°–99° C. after recrystallisation from a little butanone.

EXAMPLE 42

If 8.9 ml of chloroformic acid n-butyl ester are used instead of 5.4 ml of chloroformic acid methyl ester, 5-(2'-n-butoxycarbonylaminoethyl)-2-(3'-isopropylamino-2'-hydroxy-propoxy)-pyridine is obtained analogously to Example 41; it melts at 93°–95° C. after crystallisation from butanone and forms a neutral fumarate of melting point 145°–147° C.

EXAMPLE 43

Analogously to Example 41, using 14.1 g of 5-(2'-aminoethyl)-3-chloro-2-(3'-isopropylamino-2'-hydroxy-propoxy)-pyridine instead of 5-(2'-aminoethyl)-2-(3'-isopropylamino-2'-hydroxy-propoxy)-pyridine gives 3-chloro2-(3'-isopropylamino-2'-hydroxy-propoxy)-5-(2'-methoxycarbonylaminoethyl)-pyridine of melting point 99°–101° C. (from ether). This compound forms a neutral fumarate of melting point 179°–180° C. (from ethanol). The starting material can be prepared as follows:
(a) The crude 5,6-dichloronicotinic acid chloride obtained from 279 g of 2-hydroxy-5-pyridinecarboxylic acid, is reduced with 185 g of sodium borohydride in 3.2 liters of water analogously to the method of F. E. Ziegler and J. G. Sweeny, J. Org. Chem. 34, 3545 (1969) to give 2,3-dichloro-5-hydroxymethylpyridine, melting point 72°–75° C.
(b) 2,3-Dichloro-5-hydroxymethyl-pyridine is reacted in a known manner with thionyl chloride to give 5-chloromethyl-2,3-dichloro-pyridine and the latter is reacted with sodium cyanide, without additional purification (for example analogously to L. A. Carlson et al., Acta Pharm. Suecica 9, 411 (1972)). 5,6-Dichloro-pyridine-3-acetonitrile, thus obtained, melts at 72°–75° C. after recrystallisation from ether.
(c) 85.5 g of (5,6-dichloro-3-pyridine)-acetonitrile in 200 ml of methanol are reduced analogously to Example 40 a) with 18.5 g of sodium borohydride in 65 ml of concentrated sodium hydroxide solution and 20 g of Raney nickel. 5-(2'-Aminoethyl)-2,3-dichloro-pyridine is obtained from the resulting crude product by distillation in a bulb tube at 95°–115° C. bath temperature and 0.08 mm Hg.
(d) 12 g of sodium hydride dispersion (55% strength) are added in portions to 44 g of 5-(2'-aminoethyl)-2,3-dichloro-pyridine and 55 g of 5-hydroxymethyl-3-isopropyl-2-phenyl-oxazolidine, dissolved in 500 ml of 1,2-dimethoxyethane, whilst cooling with ice at 0°–10° C. The reaction mixture is then stirred for 2 hours at room temperature and 16 hours under reflux. Working up gives crude 5-(2'-aminoethyl)-3-chloro-2-[3'-isopropyl-2'-phenyl-oxazolidinyl-(5')]-methoxy-pyridine, which is hydrolysed without further purification, analogously to Example 37), to give 5-(2'-aminoethyl)-3-chloro-2-(3'-isopropylamino-2'-hydroxy-propoxy)-pyridine (boiling point 165°–185° C./0.06 mm Hg).

EXAMPLE 44

6 g of 5-aminomethyl-2-(2'-hydroxy-3'-isopropylamino-propoxy)-pyridine dissolved in 25 ml of isopropanol and 25 ml of water are reacted analogously to Example 41) with 2.3 ml of chloroformic acid methyl ester, and worked up, and give 2-(2'-hydroxy-3'-isopropylaminopropoxy)-5-methoxy-carbonylaminomethyl-pyridine of melting point 96°–97° C. (from ether). The neutral fumarate of this compound melts at 138°–140° C.

EXAMPLE 45

Analogously to Example 44), using 3.7 ml of chloroformic acid n-butyl ester instead of the methyl ester gives 2-(2'-hydroxy-3'-isopropylamino-propoxy)-5-(n-butoxycarbonyl-aminomethyl)-pyridine of melting point 85°–87° C. (sintering from 79° C. onwards), after recrystallisation from dichloromethane-ether.

EXAMPLE 46

60 ml of 4 N hydrochloric acid are added to a solution of 24 g of 2-[3'-tert.-butyl-2'-phenyl-oxazolidinyl-(5')]-methoxy-3-ethoxy-pyridine in 100 ml of ethanol and the mixture is left to stand for 2 hours at room temperature. The solvent is evaporated off in vacuo and the residue is dissolved in approx. 100 ml of water. This solution is extracted with 100 ml of ether. The aqueous phase is separated off, rendered strongly alkaline with concentrated potassium hydroxide solution and extracted with ether. After drying, and evaporating off the solvent, a dark oil is obtained, which is distilled in a bulb tube at 130° C./0.03 mm Hg. 2-(3'-tert.Butylamino-2'-hydroxy-propoxy)-3-ethoxy-pyridine, thus obtained, is mixed with half the equivalent amount of fumaric acid, dissolved in methanol, the solution is evaporated in vacuo and butanone is added to the residue. This results in the crystallisation of the neutral fumarate of melting point 170°–172° C., crystal transition at 161°–163° C.

EXAMPLE 47

19.5 g of crude 3-(2',3'-epoxy-propoxy)-2-nitro-pyridine, dissolved in 300 ml of isopropanol, are boiled with 100 ml of isopropylamine for 4 hours under reflux. After working up analogously to Example 14), 3-(2'-hydroxy-3'-isopropylamino-propoxy)-2-nitro-pyridine is obtained, melting at 99°–101° C. after crystallisation from ether.

The starting material is obtained as follows:

(a) 28 g of 2-nitro-3-pyridinol, 200 ml of epichlorohydrin and 60 g of potassium carbonate in 500 ml of acetonitrile are boiled for 8 hours under reflux, whilst stirring. Filtration and evaporation of the reaction mixture gives crude 3-(2',3'-epoxy-propoxy)-2-nitro-pyridine as a yellow oil.

EXAMPLE 48

5.2 g of 2-[(3'-isopropyl-oxazolidin-2'-on-5'-yl)-methoxy]-4-phenyl-pyridine in a mixture of 70 ml of ethanol and 20 ml of 2 N sodium hydroxide solution are boiled for 16 hours under reflux. The reaction mixture is evaporated in vacuo and is then partitioned between 100 ml of ether and 20 ml of water. The organic phase is separated off and extracted with 40 ml of 2 N hydrochloric acid. The hydrochloric acid extract is rendered alkaline with concentrated sodium hydroxide solution and the oil which has separated out is again extracted with ether. 2-(2'-Hydroxy-3'-isopropylamino-propoxy)-4-phenylpyridine, isolated in this way, forms a neutral fumarate of melting point 171°–173° C.

EXAMPLE 49

60 ml of 4 N hydrochloric acid are added to a solution of 48 g of 2-[3'-isopropyl-2'-phenyl-oxazolidinyl-(5')]-methoxy-3-chloro-pyridine in 200 ml of ethanol and the mixture is left to stand for 3 hours at room temperature. The solvent is evaporated off in vacuo and the residue is dissolved in approx. 200 ml of water. This solution is extracted with 100 ml of ether. The aqueous phase is separated off, rendered strongly alkaline with concentrated potassium hydroxide solution and extracted with methylene chloride. After drying and evaporation of the solvent, an oil is obtained from which 2-(3'-isopropylamino-2'-hydroxy-propoxy)-3-chloro-pyridine is isolated as the hydrochloride by adding a solution of hydrochloric acid in methanol until the pH is 2–3. The hydrochloride melts at 167°–169° C. after recrystallisation from methanolacetone.

EXAMPLE 50

60 ml of 4 N hydrochloric acid are added to a solution of approx. 35 g of 4-[3'-isopropyl-2'-phenyl-oxazolidinyl-(5')]-methoxy-3-methyl-pyridine in 100 ml of ethanol and the mixture is left to stand for 2 hours at room temperature. The solvent is evaporated off in vacuo and the residue is dissolved in approx. 100 ml of water. This solution is extracted with 100 ml of ether. The aqueous phase is separated off, rendered strongly alkaline with concentrated potassium hydroxide solution and extracted with methylene chloride. After drying and evaporation of the solvent, a yellow oil is obtained, which is distilled in a bulb tube at 145° C./0.02 mm Hg. 4-(3'-Isopropylamino-2'-hydroxy-propoxy)-3-methyl-pyridine, thus obtained, is mixed with the equivalent amount of fumaric acid, dissolved in methanol, the solution is evaporated in vacuo and isopropanol is added to the residue. Hereupon, the acid fumarate of melting point 167°–169° C. crystallises.

EXAMPLE 51

5.3 g of 5-(2'-aminoethyl)-3-chloro-2-(3'-isopropylamino-2'-hydroxy-propoxy)-pyridine are reacted analogously to Example 41) with 2.2 g of chloroformic acid ethyl ester in a mixture of 25 ml of isopropanol and 25 ml of water and after recrystallisation from acetone-ether, 5-(2'-ethoxy-carbonylamino-ethyl)-3-chloro-2-(3'-isopropylamino-2'-hydroxy-propoxy)-pyridine of melting point 120°–122° C. is obtained. It gives a neutral fumarate of melting point 149°–151° C. (from ethanol-acetone).

EXAMPLE 52

32 g of crude 2-[(3'-isopropyl-2'-phenyl-oxazolidin-5'-yl)-methoxy]-3-chloro-5-[(tetrahydropyran-2'-yloxy)-methyl]-pyridine are dissolved in 250 ml of 2 N sulphuric acid and the solution is left to stand for 4 hours at room temperature and is then extracted with 100 ml of ether. The aqueous phase is evaporated to approx. 50 ml in vacuo, rendered alkaline with concentrated sodium hydroxide solution and extracted with three times 150 ml of methylene chloride. 3-Chloro-2-(2'-hydroxy-3'-isopropylamino-propoxy)-5-hydroxy-methyl-pyridine, obtained after drying and evaporation of the solvent, distils as a colourless oil in a bulb tube at 170°–180° C./0.04 mm Hg and forms a neutral fumarate of melting point 205°–207° C. (from methanol).

EXAMPLE 53

A solution of 45 g of crude 3-methyl-2-[2-phenyl-3-(4-phenyl-2-butyl)-oxazolidin-5-yl]-methoxy-pyridine in 200 ml of ethanol is hydrolysed with 120 ml of 4 N hydrochloric acid for 3 hours at 20° C. analogously to Example 31, and the mixture is worked up. Distillation in a bulb tube at 140°–150° C./0.04 mm Hg gives 2-[2'-hydroxy-3'-(1-methyl-3-phenyl-propylamino)-propoxy]-3-methyl-pyridine as a light yellow oil.

The starting material can be prepared as follows:
(a) 31.1 g of 2-phenyl-3-(1-phenyl-3-butyl)-5-hydroxymethyl-oxazolidine, dissolved in 150 ml of dimethylformamide, are reacted with 6.5 g of sodium hydride dispersion (55% strength) and subsequently with 34.4 g of 2-bromo- b 3-methyl-pyridine over the course of 18 hours. Crude 3-methyl-3-[2-phenyl-3-(4-phenyl-3-butyl)-oxazolidin-5-yl]-methoxy-pyridine is thus obtained.

EXAMPLE 54

A mixture of 6.1 g of 6-methyl-3-pyridinol, 5.5 g of 1-isopropyl-3-azetidinol, 0.3 g of potassium hydroxide and 25 ml of benzyl alcohol is stirred for 16 hours under nitrogen in a bath at 150° C. After cooling, the reaction mixture is diluted with 50 ml of ether and extracted with 30 ml of 4 N hydrochloric acid. The aqueous phase is separated off, rendered alkaline with concentrated sodium hydroxide solution and extracted with 100 ml of methylene chloride. 3-(3'-Isopropylamino-2'-hydroxy-propoxy)-6-methyl-pyridine is isolated from the crude product thus obtained by bulb tube distillation at 130°–140° C. bath temperature and 0.04 mm Hg. It is identical in its properties with the product obtained in Example 19.

EXAMPLE 55

14.8 g of 3-benzyloxy-2-(2'-hydroxy-3'-isopropylamino-propoxy)-6-methyl-pyridine, dissolved in 150 ml of dioxane, are hydrogenated with addition of 1.5 g of palladium on charcoal, as the catalyst. After the theoretical amount of hydrogen has been absorbed, the hydrogenation stops. The catalyst is filtered off, the filtrate is evaporated and the oil which remains is treated with a solution of 2.6 g of fumaric acid in approx. 50 ml of methanol. This solution is filtered and evaporated in vacuo to give an oil, and 50 ml of isopropanol are added to the residue. Hereupon, the neutral fumarate of 2-(2'-hydroxy-3'-isopropylamino-propoxy)-

6-methyl-3-pyridinol, of melting point 198°–200° C., crystallises.

EXAMPLE 56

Catalytic debenzylation of 6-benzyloxy-2-(2'-hydroxy-3'-isopropylamino-propoxy)-pyridine analogously to Example 55 gives 6-(2'-hydroxy-3'-isopropylamino-propoxy)-2-pyridinol, melting point 177°–178° C. (from methanol-ether), The starting material can be obtained as follows:
(a) 2,6-Dichloropyridine is reacted with 1-equivalent of sodium benzylate in dimethylformamide to give 2-benzyloyxy-6-chloro-pyridine (boiling point 95°–100° C./0.01 mm Hg).
(b) 2-Benzyloxy-6-chloro-pyridine is converted into 2-benzyloxy-6-(2'-hydroxy-6'-isopropylamino-propoxy)-pyridine in the usual manner (boiling point 140°–150° C./0.02 mm Hg in a bulb tube, melting point 57°–64° C.).

EXAMPLE 57

Catalytic debenzylation of 3-benzyloxy-2-(2'-hydroxy-3'-isopropylamino-propoxy)-pyridine analogously to Example 55 gives 2-(2'-hydroxy-3'-isopropylamino-propoxy)-3-pyridinol.

The starting material can be obtained from 3-benzyloxy-2-nitro-pyridine in the usual manner.

EXAMPLE 58

A solution of 10 g of phosgene in 40 ml of toluene is added dropwise at 5°–10° C. to 15.6 g of 3-(2'-hydroxy-3'-isopropylamino-propoxy)-6-methyl-pyridine, dissolved in 75 ml of dioxane, in the presence of 8 ml of 2,6-lutidine, whilst stirring. The reaction mixture is stirred overnight at room temperature and is then evaporated in vacuo. The evaporation residue is rendered alkaline with a little concentrated sodium hydroxide solution and is extracted with 200 ml of ethyl acetate. The organic phase is evaporated, initially at approx. 20 mm Hg and then at 0.01 mm Hg/60° C. bath temperature. Approx. 50 ml of ether are added to the residue which remains, giving crystalline 3-isopropyl-5-[(6-methylpyridin-3-yloxy)methyl]-oxazolidin-2-one of melting point 86°–88° C.

EXAMPLE 59

A solution of 4.1 g of m-chloroperbenzoic acid in 30 ml of dichloromethane is added over the course of 10 minutes to a solution of 4.8 g of 3-isopropyl-5-[(6-methylpyridin-3-yloxy)methyl]-oxazolidin-2-one in 50 ml of dichloromethane, whilst stirring, and the mixture is left to stand overnight at room temperature. After dilution with 50 ml of dichloromethane the reaction mixture is extracted with 30 ml of saturated potassium bicarbonate solution at a time, dried over sodium sulphate and evaporated in vacuo. The crystalline residue is recrystallised from dichloromethane - ether. 3-[(3-Isopropyl-oxazolidin-2-on-5-yl)methoxy]-6-methyl-pyridine-1-oxide, thus obtained, melts at 137°–139° C.

EXAMPLE 60

4 ml of a 2 N solution of hydrogen chloride in methanol are added to a solution of 3.6 g of 2-(3'-amino-2'-hydroxy-propoxy)-3-methyl-pyridine and 1.5 g of sodium cyanoborohydride in 70 ml of methanol and 12 ml of acetone are added dropwise over the course of approx. 30 minutes, whilst stirring. The reaction mixture is stirred overnight at room temperature and is then evaporated in vacuo and the residue is acidified with 2 N hydrochloric acid. The aqueous solution is extracted once by shaking with 30 ml of ether. The hydrochloric acid phase is separated off and rendered alkaline with concentrated sodium hydroxide solution. 2-(2'-Hydroxy-3'-isopropylamino-propoxy)-3-methyl-pyridine is isolated by extraction with ethyl acetate and is identical with the material described in Example 21.

The starting material can be prepared as follows:
(a) Glycerol glycid and benzylamine are reacted in a known manner to give 3-benzylamino-1,2-propanediol (boiling point 160°–170° C./0.01 mm Hg),
(b) 3-benzylamino-1,2-propanediol and benzaldehyde are converted by azeotropic distillation with benzene, in a manner which is in itself known, into 3-benzyl-5-hydroxymethyl-2-phenyl-oxazolidine (boiling point 168°–171° C./0.005 mm Hg).
(c) The use of 2-bromo-3-methyl-pyridine and 3-benzyl-5-hydroxy-methyl-2-phenyl-oxazolidine gives 2-(3'-benzylamino-2'-hydroxy-propoxy)-3-methyl-pyridine in the usual manner. The latter melts at 77°–82° C. after recrystallisation from ethyl acetate-cyclohexane.
(d) Catalytic debenzylation of a solution of 28.3 g of 2-(3'-benzylamino-2'-hydroxy-propoxy)-3-methyl-pyridine in 300 ml of ethyl acetate, with the addition of a total of 12 g of palladium on charcoal (5% strength), gives 2-(3'-amino-2'-hydroxy-propoxy)-3-methylpyridine of boiling point 120°–130° C./0.07 mm Hg in a bulb tube.

EXAMPLE 61

27 g of crude 2,3-dichloro-5-[(tetrahydropyran-2-yloxy)-methyl]-pyridine are boiled for 16 hours under reflux with 25 g of 5-hydroxymethyl-3-isopropyl-2-phenyl-oxazolidine and 4.5 g of sodium hydride dispersion (55% strength) in 250 ml of 1,2-dimethoxyethane and the mixture is worked up in the usual manner. This gives crude 2-[(3'-isopropyl-2'-phenyl-oxazolidin-5'-yl)-methoxy]-3-chloro-5-[(tetrahydropyran-2-yloxy)-methyl]-pyridine.

The starting material can be prepared as follows: 2,3-Dichloro-5-hydroxymethyl-pyridine is converted by means of 2,3-dihydropyrane into 2,3-dichloro-5-[(tetrahydropyran-2-yloxy)-methyl]pyridine (boiling point 115°–123° C./0.08 mm Hg) in a known manner.

EXAMPLE 62

4.25 g of sodium hydride dispersion (55% strength) is introduced over the course of 1 hour into a solution of 16.0 g of 2,3-dichloro-5-methylaminocarbonyl-pyridine and 18.5 g of 5-hydroxymethyl-3-isopropyl-2-phenyl-oxazolidine in 250 ml of hexamethylphosphoric acid triamide, whilst stirring and cooling. The reaction mixture is stirred overnight at room temperature and then poured onto 250 ml of ice water, and extracted with three times 200 ml of ether. The combined ether extracts are evaporated and give crude 2-[3'-isopropyl-2'-phenyl-oxazolidinyl-(5')]-methoxy-3-chloro-5-methylaminocarbonyl-pyridine.

The starting material can be prepared via the following stages.
(a) A solution of 63 g of potassium chlorate in 750 ml of water is added dropwise to a suspension of 210 g of 2-hydroxypyridine-5-carboxylic acid in 1.5 liters of concentrated hydrochloric acid at 80°–85° C. In the course of the dropwise addition, a yellow solution is produced, from which crystals gradually separate out again. After the dropwise addition (1.5–2 hours) the reaction mixture is cooled in an ice bath and 2-hydroxy-3-chloropyridine-5-carboxylic acid, which has crystallised out, is filtered off (melting point 318°–322° C.).

(b) 45 g of 2-hydroxy-3-chloro-pyridine-5-carboxylic acid are added over the course of approx. 30 minutes, whilst stirring, to a suspension of 108 g of phosphorus pentachloride in 300 ml of toluene. The reaction mixture is boiled for 2 hours under reflux and is then thoroughly evaporated in vacuo on a rotary evaporator, ultimately at a bath temperature of 70°–80° C. The crude 5,6-dichloronicotinic acid chloride thus obtained is used in the crude form for the next stage.

(c) A solution of 30 g of crude 5,6-dichloronicotinic acid chloride in 150 ml of chloroform is added dropwise to a solution of 50 g of methylamine in 250 ml of ethanol whilst stirring and cooling at 10°–15° C. The reaction mixture is stirred for a further 2 hours at 20°–30° C. and is then evaporated in vacuo. The evaporation residue is taken up in ethyl acetate and this solution is washed with 2 N sodium carbonate solution, dried over magnesium sulphate and evaporated. The residue is recrystallised from ethanol-ether. 2,3-Dichloro-5-methylaminocarbonyl-pyridine, thus obtained, melts at 134°–138° C.

EXAMPLE 63

6.1 g of sodium hydride dispersion (55% strength) are added cautiously, in portions, to a solution of 46.8 g of 5-hydroxymethyl-3-isopropyl-2-phenyl-oxazolidine in 300 ml of 1,2-dimethoxyethane at 20°–40° C. and after foaming has ceased the mixture is stirred for a further 1–2 hours at 40° C. 11.0 g of 5-(2'-amino-ethyl)-2-chloro-pyridine are then added and the reaction mixture is stirred for 18 hours at 80° C. After evaporating off the solvent in vacuo, the evaporation residue is taken up in ether and the ether solution is washed with water, dried over magnesium sulphate and evaporated in vacuo. Crude 2-[3'-isopropyl-2'-phenyl-oxazolidinyl-(5')]-methoxy-5-(2'-aminoethyl)-pyridine is thus obtained.

The starting material can be prepared as follows: Approx. 10 g of Raney nickel suspension are added to a solution of 30.4 g of (6-chloro-3-pyridine)-acetonitrile in 90 ml of methanol and a solution of 7.6 g of sodium borohydride in 25 ml of 8 N sodium hydroxide solution is then added dropwise at 50°–60° C. The temperature is kept at 50°–60° C. by cooling. After the dropwise addition, the reaction mixture is stirred for a further 20 minutes at approx. 50° C. The mixture is then cooled, the nickel is filtered off and the filtrate is evaporated in vacuo. The dark red oil which remains is stirred for 1 hour with 15 g of solid potassium hydroxide and the resulting suspension is extracted with a total of 200 ml of dichloromethane. After drying the extract and evaporating off the solvent, an oil is obtained, from which 5-(2'-aminoethyl)-2-chloropyridine is isolated as a colourless oil by distillation in a high vacuum at 76°–80° C./0.02 mm Hg.

EXAMPLE 64

4.8 g of sodium hydride dispersion (55% strength) are cautiously added in portions to a solution of 27.5 g of 5-hydroxymethyl-3-isopropyl-2-phenyl-oxazolidine in 100 ml of dimethylformamide at 20°–40° C. and after foaming has ceased the mixture is stirred for a further 1–2 hours at 40° C. 12.7 g of 2-chloro-4-methyl-pyridine are then added and the reaction mixture is stirred for 2 hours at 80° C. After evaporating off the solvent in vacuo, the evaporation residue is taken up in ether and the ether solution is washed with water, dried over magnesium sulphate and evaporated in vacuo. Crude 2-[3'-isopropyl-2'-phenyl-oxazolidinyl-(5')]-methoxy-4-methyl-pyridine is thus obtained.

The following compounds can also be synthesised analogously: 2-[3'-Isopropyl-2'-phenyl-oxazolidinyl-(5')]-methoxy-5-methyl-pyridine, 2-[3'-isopropyl-2'-phenyl-oxazolidinyl-(5')]-methoxy-3-ethoxy-pyridine, 2-[3'-isopropyl-2'-phenyl-oxazolidinyl-(5')]-methoxy-6-methyl-pyridine, 2-[3'-isopropyl-2'-phenyl-oxazolidinyl-(5')]-methoxy-3-ethoxy-pyridine, 2-[3'-isopropyl-2'-phenyl-oxazolidinyl-(5')]-methoxy-5-cyanopyridine, 2-[3'-isopropyl-2'-phenyl-oxazolidinyl-(5')]-methoxy-3-chloropyridine and 4-[3'-isopropyl-2'-phenyl-oxazolidinyl-(5')-methoxy-3-methylpyridine.

EXAMPLE 65

2-[3'-Isopropyl-2'-phenyl-oxazolidinyl-(5')]-methoxy-3-chloro-5-n-hexylaminocarbonyl-pyridine can be prepared analogously to Example 62 using 15.6 g of 2,3-dichloro-5-n-hexylaminocarbonyl-pyridine, 13.6 g of 5-hydroxy-methyl-3-isopropyl-2-phenyl-oxazolidine and 3.15 g of sodium hydride dispersion (55% strength in oil) in 250 ml of hexamethylphosphoric acid triamide.

The starting material can be prepared analogously to Example (62c).

2,3-Dichloro-5-n-hexylamino-carbonylpyridine can be prepared using 30 g of n-hexylamine and melts at 87°–89° C. after recrystallisation from ether/n-hexane.

EXAMPLE 66

3-(2'-Methoxyethoxy)-2-(3'-isopropylamino-2'-hydroxy-propoxy)-pyrazine is obtained analogously to the description in Example 11 from 9.4 g (0.05 mol) of 2-chloro-3-(2'-methoxyethoxy)-pyrazine. The fumarate prepared therefrom with fumaric acid crystallises from methanol-acetone, melting point 120°–121° C.

2-Chloro-3-(2'-methoxyethoxy)-pyrazine used as the starting material, can be prepared as follows: 14.9 g (0.1 mol) of 2,3-dichloropyrazine and 30 g (0.5 mol) of ethylene glycol monomethyl ether are dissolved in 150 ml of hexamethylphosphoric acid triamide and 4.8 g (0.1 mol) of a 50% strength suspension of sodium hydride in paraffin oil is added in portions at 0°–5° C. The reaction mixture is then stirred for 15 hours at room temperature, poured into 1 liter of ice water and extracted by shaking with ether. The ether extracts are washed with water, dried over sodium sulphate and evaporated in a waterpump vacuum. The residue is distilled in a high vacuum. 2-Chloro-3-(2'-methoxyethoxy)-pyrazine, boiling point 74° C./0.003 mm Hg, $n_D^{22}$: 1.5118, is obtained.

EXAMPLE 67

Analogously to the description in Example 8, 7.5 g (0.03 mol) of 3-chloro-2-(3'-isopropylamino-2'-hydroxy-propoxy)-pyrazine, 2.8 g (0.045 mol) of ethylmercaptan and 2.4 g (0.045 mol) of sodium methylate in 150 ml of methanol, when refluxed for 30 hours, give the crude base 3-ethylthio-2-(3'-isopropylamino-2'-hydroxy-propoxy)-pyrazine, and this is converted, with 1.74 g of fumaric acid, into the fumarate of melting point 158°–160° C. when crystallised from methanol-ether.

EXAMPLE 68

9.8 g (0.04 mol) of 3-chloro-2-(3'-isopropylamino-2'-hydroxy-propoxy)-pyrazine and 12.1 g (0.12 mol) of 4-hydroxypiperidine are warmed to 130° C. for 1 hour. After cooling, the reaction mixture is taken up in a 1:3 chloroform-ether mixture and the solution is washed with 2 N sodium hydroxide solution and water. The organic phase is dried over sodium sulphate and evaporated in a waterpump vacuum. 3-(4'-Hydroxy-1'-piperidyl)-2-(3'-isopropylamino-2'-hydroxy-propoxy)-pyrazine, melting point 88°–91° C. from ether-pentane, is obtained. The cyclamate prepared therefrom with cyclohexylaminosulphonic acid crystallises from acetone; melting point 90°–92° C.

EXAMPLE 69

Analogously to the description in EXAMPLE 68, 9.8 g (0.04 mol) of 3-chloro-2-(3'-isopropylamino-2'-hydroxy-propoxy)-pyrazine and 12.0 g (0.12 mol) of N-methylpiperazine give 3-(4-methyl-1-piperazinyl)-2-(3'-isopropylamino-2'-hydroxy-propoxy)-pyrazine, melting point 62°–64° C. from petroleum ether. The fumarate prepared therefrom with fumaric acid crystallises from methanol, melting point 200°–201° C.

EXAMPLE 70

Analogously to the description in Example 11, 10.7 g (0.05 mol) of 2-chloro-3-morpholinyl-5-methyl-pyrazine and 15.5 g (0.05 mol) of 2-phenyl-3-(1-phenyl-3-butyl)-5-hydroxymethyl-oxazolidine give 2-[3'-(1-phenyl-3-butylamino)-2'-hydroxypropoxy]-3-morpholinyl-5-methyl-pyrazine from which the fumarate is obtained with 2.25 g of fumaric acid; the fumarate crystallises from methanol/acetone, melting point 134°–136° C.

EXAMPLE 71

Analogously to the description in Example 11, 11.1 g (0.05 mol) of 2-chloro-3-phenylthio-pyrazine and 13.2 g (0.06 mol) of 2-phenyl-3-isopropyl-5-hydroxymethyl-oxazolidine give 3-phenyl-thio-2-(3'-isopropylamino-2'-hydroxy-propoxy)-pyrazine, melting point 70°–71° C. when crystallised from ether-petroleum ether.

The fumarate, prepared therefrom, crystallises from isopropanol, melting point 167°–169° C.

2-Chloro-3-phenylthio-pyrazine, used as the starting material, can be prepared as follows:

22 g (0.2 mol) of thiophenol and 29.8 g (0.2 mol) of 2,3-dichloropyrazine are successively added dropwise to a solution of 10.8 g (0.2 mol) of sodium methylate in 200 ml of ethanol and the mixture is stirred for 1 hour. The reaction mixture is then cooled to 0° C. and the reaction product which has precipitated is filtered off and washed with ethanol and water. After drying, 2-chloro-3-phenylthiopyrazine, melting point 100°–111° C., is obtained.

EXAMPLE 72

Analogously to the description in Example 11, 8.2 g (0.05 mol) of 2,3-dichloro-5-methyl-pyrazine, 11 g (0.05 mol) of 2-phenyl-3-isopropyl-5-hydroxymethyl-oxazolidine and 3.4 g of a 50% strength suspension of sodium hydride in paraffin oil give 2-chloro-3-(3'-isopropylamino-2'-hydroxy-propoxy)-5-methyl-pyrazine, melting point 109°–110° C. when crystallised from benzene. The fumarate prepared therefrom by means of fumaric acid crystallises from methanol-ether, melting point 164°–165° C.

EXAMPLE 73

Analogously to the description in Example 3, 5.2 g (0.02 mol) of 2-chloro-3-(3'-isopropylamino-2'-hydroxy-1-propoxy)-5-methyl-pyrazine gives 3-(3'-isopropylamino-2'-hydroxy-propoxy)-5-methyl-pyrazine, melting point 78°–79° C. when crystallised from ether-petroleum ether. The hydrochloride prepared therefrom crystallises from methanol-acetone, melting point 125° C.

EXAMPLE 74

11.0 g of 2-phenyl-3-isopropyl-5-hydroxymethyl-oxazolidine are added to a suspension of 1.2 g of sodium hydride in 50 ml of dimethoxyethane and the mixture is stirred for 2 hours at room temperature. 5.7 g of 2-chloropyrimidine, dissolved in 20 ml of dimethoxyethane, are then added. The mixture is stirred for a further 2 hours at room temperature and is then heated to the boil for 17 hours. The inorganic salt which has precipitated is then filtered off, the filtrate is evaporated in vacuo and the residual 2-[3'-isopropyl-2'-phenyl-oxazolidinyl-(5')]-methoxypyrimidine is isolated as an oil.

EXAMPLE 75

8.5 g of 5-(N-hexylcarbamoyl)-2-[3'-isopropyl-2'-phenyl-oxazolidinyl-(5')]-methoxypyrimidine are taken up in 25 ml of 1 N hydrochloric acid. The mixture is heated to the boil for ten minutes and cooled, the benzaldehyde which has separated out is extracted with ether and the water phase which has been separated off is mixed with 13 ml of 2 N sodium hydroxide solution. The base, which separates out as an oil is extracted with ethyl acetate and the extract is washed with water, dried over sodium sulphate, filtered and evaporated under reduced pressure. The evaporation residue is crystallised from petroleum ether. 5-N-Hexylcarbamoyl)-2-(3'-isopropylamino-2'-hydroxypropoxy)-pyrimidine is obtained as colourless crystals of melting point 114°–115° C. Its hydrogen oxalate, prepared in acetone, melts at 149°–150° C.

EXAMPLE 76

8.2 g of 2-phenyl-3-isopropyl-5-hydroxy-methyl-oxazolidine are added to a suspension of 0.88 g of sodium hydride in 20 ml of dimethoxyethane and the mixture is stirred for 2 hours at room temperature. 9.0 g of 5-(N-hexylcarbamoyl)-2-chloropyrimidine, dissolved in 30 ml of dimethoxyethane, are then added dropwise. The mixture is then stirred for 18 hours at room temperature. The inorganic salt which has precipitated is then filtered off, the filtrate is evaporated in vacuo and the oil which remains contains 5-(N-hexylcarbamoyl)-2-[3'-isopropyl-2'-phenyl-oxazolidinyl-(5')]-methoxypyrimidine.

The starting material can be prepared as follows: 20.2 g of n-hexylamine are added dropwise over the course of one hour to a solution of 22.6 g of 2,4(6)-dichloro-pyrimidine-5-carboxylic acid chloride in 150 ml of diethyl ether at −10° C., whilst stirring, and the mixture is then stirred for a further hour at 0° C. The precipitate which has separated out is then filtered off. 5-(N-Hexylcarbamoyl)-2,4(6)-dichloropyrimidine is obtained as a colourless oil from the filtrate after distilling off the ether.

9.7 g of 5-(N-hexylcarbamoyl)-2,4(6)-dichloropyrimidine in 100 ml of 50% strength ethanol are heated to the boil with 20 g of zinc dust for 1½ hours, whilst stirring. After hot filtration and rinsing with ethanol, the filtrate is largely freed from the ethanol by distillation under reduced pressure. The oil which precipitates from the aqueous solution is extracted with ethyl acetate and the extract is washed with water, dried over sodium sulphate and evaporated. The oil which remains is chromatographed on 50 g of Merck Kieselgel 60 using benzene-ether (1:1). The fractions containing the product are combined. After distilling off the solvent, 5-(N-hexylcarbamoyl)-2-chloro-pyrimidine is obtained as a colourless oil which gives crystals of melting point 101°-102° C. from petroleum ether.

EXAMPLE 77

9.0 g of 2-dimethylamino-5-carboethoxy-4(6)-[3'-isopropyl-2'-phenyloxazolidinyl-(5')]-methoxypyrimidine are taken up in 45 ml of 1 N hydrochloric acid. The mixture is heated to the boil for ten minutes and cooled, the benzaldehyde which has separated out is extracted with ether and 23 ml of 2 N sodium hydroxide solution are added to the water phase which has been separated off. The base which separates out as an oil is extracted with ethyl acetate and the extract is washed with water, dried over sodium sulphate, filtered and evaporated under reduced pressure. The resulting oil is dissolved in a little acetone and a solution of 2.9 g of oxalic acid in acetone is added. 2-Dimethylamino-5-carboethoxy-4(6)-(3'-isopropylamino-2'-hydroxypropoxy)-pyrimidine oxalate is obtained and is recrystallised from methanol-acetone; melting point 155°-156° C.

EXAMPLE 78

4.8 g of 2-phenyl-3-isopropyl-5-hydroxymethyl-oxazolidine are added to a suspension of 0.53 g of sodium hydride in 20 ml of dimethoxyethane and the mixture is stirred for 2 hours at room temperature. 5.0 g of 2-dimethylamino-4-chloro-5-carboethoxypyrimidine, dissolved in 30 ml of dimethoxyethane, are then added dropwise. The mixture is then stirred for 18 hours at room temperature and finally for one hour at 80° C. The salt which has precipitated is then filtered off, the filtrate is evaporated in vacuo and the oil which remains contains the 2-dimethylamino-5-carboethoxy-4-[3'-isopropyl-2'-phenyloxazolidinyl-(5')]-methoxypyrimidine.

The starting material can be obtained as follows:

A suspension of 16 g of 2-dimethylamino-4-hydroxy-5-carboethoxy-pyrimidine in 100 ml of phosphorous oxychloride is heated to the boil for half an hour whilst stirring and is then filtered hot, and the filtrate is evaporated under reduced pressure. 200 g of ice are added to the oily residue. 200 ml of methylene chloride are added and 30% strength sodium hydroxide solution is then added, whilst cooling with ice, until the pH reaches 8. Inorganic salts which have precipitated are then filtered off and rinsed with methylene chloride. The organic phase is washed with water, dried over sodium sulphate and evaporated. 2-Dimethylamino-4-chloro-5-carboethoxypyrimidine is obtained as a yellowish oil which can be used further without purification.

EXAMPLE 79

0.195 g of crude 1-(2-methylthio-5-pyrimidinyloxy)-2,3-epoxypropane is dissolved in 10 ml of isopropanol and, after the addition of 1.5 ml of isopropylamine, the whole is refluxed for 18 hours, and the reaction mixture is subsequently concentrated in vacuo. The residue is dissolved in acetone, the solution is filtered until clear, and a solution of 0.1 g of oxalic acid in 0.5 ml of acetone is added to the filtrate. With trituration there crystallises 5-(3'-isopropylamino-2'-hydroxypropoxy)-2-methylthiopyrimidine-hydrogen-oxalate, which is recrystallised from methanol/acetone; m.p. 196°-197°.

The 1-(2-methylthio-5-pyrimidinyloxy)-2,3-epoxypropane used as starting material can be produced as follows:

0.9 ml of epichlorohydrin is added, with stirring, to 1.42 g of 5-hydroxy-2-methylthiopyrimidine and 2.1 g of potassium carbonate in 30 ml of acetone, and the whole is subsequently refluxed for 40 hours. The reaction mixture is filtered with suction, the filter residue is washed with acetone, and the filtrate is concentrated in vacuo. As residue there is obtained a brown oil consisting of crude 1-(2-methylthio-5-pyrimidinyloxy)-2,3-epoxypropane, which can be further used without purification.

EXAMPLE 80

7.0 g of 5-(2-methoxyethyl)-2-[3'-isopropyl-2'-phenyloxazolidinyl-(5')]-methoxypyrimidine are taken up in 24 ml of 1 N hydrochloric acid. The mixture is heated to the boil for ten minutes and cooled, the benzaldehyde which has separated out is extracted with ether and 12 ml of 2 N sodium hydroxide solution are added to the water phase which has been separated off. The base, which separates out as an oil, is extracted with ethyl acetate and the extract is washed with water, dried over sodium sulphate, filtered and evaporated under reduced pressure. The resulting oil is dissolved in a little isopropanol, a solution of 2.3 g of fumaric acid in 30 ml of isopropanol is added and the solvent is then largely distilled off. The resulting syrup is diluted with acetone, whereupon 5-(2-methoxyethyl)-2-(3'-isopropylamino-2'-hydroxy-propoxy)-pyrimidine hydrogen fumarate crystallises. Melting point 103°-104° C. after recrystallisation from methanol-acetone.

EXAMPLE 81

4.1 g of 2-phenyl-3-isopropyl-5-hydroxy-methyl-oxazolidine are added to a suspension of 0.48 g of sodium hydride in 10 ml of dimethoxyethane and the mixture is stirred for 2 hours at room temperature. 3.4 g of 5-(2-methoxyethyl)-2-chloropyrimidine, dissolved in 10 ml of dimethoxyethane are then added. The mixture is stirred at room temperature for a further 2 hours and is then heated to the boil for 3 hours. The inorganic salt which has precipitated is then filtered off, the filtrate is evaporated in vacuo and the oil which remains contains the 5-(2-methoxyethyl)-2-[3'-isopropyl-2'-phenyl-oxazolidinyl)-(5')]-methoxypyrimidine.

The starting material can be prepared as follows:

6.0 g of 5-(2-methylsulphonyloxyethyl)-uracil are suspended in 100 ml of absolute methanol and the suspension is heated to 120°-130° C. for one hour in a pressure vessel. After cooling to room temperature, the crystals obtained are filtered off and washed with methanol. 5-(2-Methoxyethyl)-uracil, melting point 232°-234° C., is obtained.

A suspension of 10.3 g of 5-(2-methoxyethyl)-uracil in 50 ml of phosphorus oxychloride is heated to the boil for 2 hours. The resulting solution is freed of excess phosphorus oxychloride by distillation under reduced pressure and the resulting oil is poured onto 200 g of ice. The product is then extracted with ether and the extract is washed with water and sodium bicarbonate solution, dried over sodium sulphate and evaporated. The resulting oil is taken up in hot hexane, the solution is filtered to remove undissolved impurities, and the product is freed from the solvent by distillation under reduced pressure. 5-(2-Methoxyethyl)-2,4(6)-dichloro-pyrimidine is obtained as a colourless oil which can be used for the next stage without purification.

8.7 g of 5-(2-methoxyethyl)-2,4(6)-dichloropyrimidine in 100 ml of 50% strength ethanol are heated to the boil with 20 g of zinc dust for 1½ hours, whilst stirring. After hot filtering and rinsing with ethanol, the filtrate is largely freed from ethanol by distillation under reduced pressure. The oil which precipitates from the aqueous solution is extracted with ethyl acetate and the extract is washed with water, dried over sodium sulphate and evaporated. The oil which remains is chromatographed on 50 g of Merck Kieselgel 60 using benzene-ethyl acetate (1:1). The fractions containing the product are combined. After distilling off the solvent, 5-(2-methoxyethyl)-2-chloropyrimidine is obtained as a colourless oil which gives crystals of melting point 25°–26° C. from petroleum ether.

EXAMPLE 82

4.9 g of 5-methylthiomethyl-2-[3'-isopropyl-2'-phenyl-oxazolidinyl-(5')]-methoxypyrimidine are taken up in 25 ml of 1 N hydrochloric acid. The solution is heated to the boil for ten minutes and cooled, the benzaldehyde which has separated out is extracted with ether and 13 ml of 2 N sodium hydroxide solution are added to the water phase which has been separated off. The base which separates out as an oil is extracted with ethyl acetate and the extract is washed with water, dried over sodium sulphate, filtered and evaporated under reduced pressure. The resulting oil is dissolved in a little isopropanol and a solution of 0.7 g of fumaric acid in 10 ml of isopropanol is added, whereupon 5-methylthiomethyl-2-(3'-isopropylamino-2'-hydroxypropoxy)-pyrimidine hydrogen fumarate crystallises. Melting point 142°–143° C. after recrystallisation from isopropanol.

EXAMPLE 83

3.1 g of 2-phenyl-3-isopropyl-5-hydroxymethyl-oxazolidine are added to a suspension of 0.33 g of sodium hydride in 10 ml of dimethoxyethane and the mixture is stirred for 2 hours at room temperature. 2.4 g of 5-methylthiomethyl-2-chloropyrimidine, dissolved in 10 ml of dimethoxyethane are then added. The mixture is stirred for a further 2 hours at room temperature and is subsequently heated to the boil for 3 hours. The inorganic salt which has precipitated is then filtered off, the filtrate is evaporated in vacuo and the oil which remains contains 5-methylthiomethyl-2-[3'-isopropyl-2'-phenyl-oxazolidinyl-(5')]-methoxypyrimidine.

The starting material can be prepared as follows:

Methylmercaptan is introduced into a solution of 14 g of 5-hydroxymethyluracil in 80 ml of trifluoroacetic acid over the course of one hour until saturation is reached, the temperature being kept at 25° C. The solution is then left to stand for 2 hours, the solvent is evaporated under reduced pressure and the residue is crystallised from glacial acetic acid. 5-Methylthiomethyluracil is obtained as colourless crystals of melting point 239°–241° C.

A suspension of 9.4 g of 5-methylthiomethyluracil in 100 ml of phosphorus oxychloride is heated to the boil for 2 hours whilst stirring and then filtered hot, and the filtrate is evaporated under reduced pressure. 200 g of ice are added to the oily residue, the product is extracted with ether and the extract is washed with water and sodium bicarbonate solution, dried over sodium sulphate and evaporated. 5-Methylthiomethyl-2,4(6)-dichloropyrimidine is obtained as a yellow oil which can be used without purification for the next stage.

6.6 g of 5-methylthiomethyl-2,4(6)-dichloropyrimidine in 60 ml of 50% strength ethanol are heated to the boil with 15 g of zinc dust for 1½ hours, whilst stirring. After hot filtration and rinsing with ethanol, the filtrate is largely freed from ethanol by distillation under reduced pressure. The oil which precipitates from the aqueous solution is extracted with ethyl acetate and the extract is washed with water, dried over sodium sulphate and evaporated. The oil which remains is chromatographed on 50 g of Merck Kieselgel 60 using benzene-ethyl acetate (1:1). The fractions containing the product are combined. After distilling off the solvent, 5-methylthiomethyl-2-chloropyrimidine is obtained, which gives crystals of melting point 56°–57° C. from petroleum ether.

EXAMPLE 84

20.5 g of 5-ethyl-4(6)-[3'-isopropyl-2'-phenyloxazolidinyl-(5')]-methoxypyrimidine are taken up in 75 ml of 1 N hydrochloric acid. The mixture is heated to the boil for ten minutes and cooled, the benzaldehyde which has separated out is extracted with ether and 38 ml of 2 N sodium hydroxide solution are added to the water phase which has been separated off. The base which separates out as an oil is extracted with ethyl acetate and the extract is washed with water, dried over sodium sulphate, filtered and evaporated under reduced pressure. The resulting oil, crystallised from cyclohexane, gives 5-ethyl-4(6)-(3'-isopropylamino-2'-hydroxypropoxy)-pyrimidine as colourless crystals of melting point 56°–58° C. Its hydrogen fumarate, prepared in isopropanol, melts at 136°–137° C.

Example 85

13.9 g of 2-phenyl-3-isopropyl-5-hydroxymethyloxazolidine are added to a suspension of 1.5 g of sodium hydride in 20 ml of dimethoxyethane and the mixture is stirred for 2 hours at room temperature. 9.0 g of 5-ethyl-4(6)-chloropyrimidine, dissolved in 50 ml of dimethoxyethane, are then added at 0° C. The mixture is then stirred for 18 hours at room temperature followed by a further hour at 80° C. The inorganic salt which has precipitated is then filtered off, the filtrate is evaporated in vacuo and the residual oil contains the 5-ethyl-4(6)-[3'-isopropyl-2'-phenyl-oxazolidinyl-(5')]-methoxypyrimidine.

The starting material can be prepared as follows:

140 g of Raney nickel are added in portions to a suspension of 52 g of 5-ethyl-4(6)-hydroxy-2-mercaptopyrimidine in 600 ml of water at 70°–80° C. over the course of one hour, whilst stirring, and the mixture is then heated to the boil for 4 hours under reflux. The nickel is then filtered off hot and rinsed with hot water, and the filtrate is evaporated completely under reduced pressure. The yellow oil which remains crystallises on cooling and gives 5-ethyl-4-hydroxypyrimidine after filtering off, and washing the filter residue with acetone and ether. Melting point 95°–97° C. (after sintering at 87°–88° C.).

10 g of 5-ethyl-4(6)-hydroxypyrimidine are added to a mixture of 12.5 ml of N,N-diethylaniline and 50 ml of phosphorus oxychloride and the mixture is heated to 100°–110° C. for 2 hours whilst stirring. The excess phosphorus oxychloride is then removed by distillation under reduced pressure and the residue is poured onto 100 g of ice. The product is extracted with ether and the extract is washed with water and sodium bicarbonate solution, dried over sodium sulphate and evaporated. The oil which remains gives, on distillation in vacuo, 5-ethyl-4-chloropyrimidine, boiling point 95°–98° C./25 mm Hg, as a colourless oil.

Example 86

10 g of crude 3-(2,3-epoxy-propoxy)-6-methylpyridine-1-oxide in 200 ml of isopropanol are heated to the boil under reflux with 25 ml of isopropylamine for 6 hours. The reaction mixture is then evaporated in vacuo, the residue is taken up in 300 ml of ethyl acetate and this solution is extracted with 30 ml of saturated potassium bicarbonate solution. The oil obtained crystallises from ether and thus gives 3-(2'-hydroxy-3'-isopropylaminopropoxy)-6-methyl-pyridine-1-oxide of melting point 87°–89° C.

The starting material can be prepared as follows:
(a) A solution of 12.2 g of m-chloroperbenzoic acid in 100 ml of dichloromethane is added dropwise over the course of approx. 10 minutes, whilst stirring, to a solution of 10 g of crude 3-(2,3-epoxy-propoxy)-6-methyl-pyridine in 100 ml of dichloromethane, the temperature of the solution rising to 32° C. The reaction mixture is stirred for a further 30 minutes and is then extracted with 40 ml of saturated potassium bicarbonate solution, dried and evaporated in vacuo. 3-(2,3-Epoxy-propoxy)-6-methylpyridine-1-oxide, thus obtained, is used further in the crude state.

EXAMPLE 87

A mixture of 0.3 g of 3-[(3-isopropyl-oxazolidin-2-on-5-yl)methoxy]-6-methyl-pyridine-1-oxide, 30 ml of ethanol, 1.0 g of sodium hydroxide and 1 ml of water is heated to the refluxing temperature for 6 hours whilst stirring. The precipitate is filtered off, the filtrate is evaporated in vacuo and the residue is dissolved in ethyl acetate. After drying the solution and evaporating the solvent, an oil is obtained, which crystallises from ether. After a further two crystallisations from ether, 3-(2'-hydroxy-3'-isopropylamino-propoxy)-6-methylpyridine-1-oxide melts at 87°–89° C.

Example 88

35 g of 2-phenyl-3-isopropyl-5-hydroxymethyloxazolidine are added to a suspension of 3.8 g of sodium hydride in 40 ml of dimethoxyethane and the mixture is stirred for 2 hours at room temperature. 23.5 g of 2-methylmercapto-4-chloropyrimidine, dissolved in 40 ml of dimethoxyethane, are then added dropwise. The mixture is then stirred for one hour at room temperature and thereafter for 4 hours under reflux. The inorganic salt which has precipitated is then filtered off and the filtrate is evaporated in vacuo. The oil which remains contains the 2-methylmercapto-4-[3'-isopropyl-2'-phenyl-oxazolidinyl(5')]-methoxy-pyrimidine.

Example 89

5.4 g of 2-methylmercapto-4-[3'-isopropyl-2'-phenyloxazolidinyl-(5')]-methoxypyrimidine are taken up in 20 ml of 1 N hydrochloric acid. The mixture is heated to the boil for ten minutes and cooled, the benzaldehyde which has separated out is extracted with ether and the water phase which has been separated off is mixed with 10 ml of 2 N sodium hydroxide solution. The base which separates out as an oil is extracted with ethyl acetate and the extract is washed with water, dried over sodium sulphate, filtered and evaporated under reduced pressure. From tetrachloromethane, the oil obtained gives crystalline 2-methylmercapto-4(6)-[3'-isopropylamino-2'-hydroxy-propoxy]-pyrimidine of melting point 82°–83° C.

Example 90

2.57 g of 2-methylmercapto-4(6)-(3'-isopropylamino-2'-hydroxypropoxy)-pyrimidine are dissolved in 20 ml of 0.5 N hydrochloric acid, 10 g of Raney nickel moist with water are added and the mixture is then heated to 60° C. for 6 hours, whilst stirring. Whilst doing so, the reaction mixture is constantly kept at pH 5–6 by occasional dropwise addition of dilute hydrochloric acid. Finally, the nickel sludge is filtered off and rinsed with water. The filtrates are combined, rendered alkaline with dilute potassium hydroxide solution and then saturated with potassium carbonate. The mixture is extracted with ethyl acetate, the extract is dried over sodium sulphate and filtered and the filtrate is evaporated in vacuo to give the crude product as a colourless oil. This product, together with 0.9 g of oxalic acid, is dissolved in 5 ml of methanol whilst warming. On cooling, 4(6)-(3'-isopropylamino-2'-hydroxypropoxy)-pyrimidine hydrogen oxalate is obtained; it is purified by recrystallisation from methanol. Melting point 164°–165° C.

EXAMPLE 91

3.2 g of crude 1-(5-pyrimidinyloxy)-2,3-epoxypropane is dissolved in 50 ml of isopropanol and, after the addition of 15 ml of isopropylamine, the whole is refluxed for 18 hours. The reaction mixture is then concentrated in vacuo, the residue is taken up in 25 ml of acetone, the solution is heated to boiling, and 25 ml of ethyl acetate is added. The solution is subsequently decanted from undissolved resins and afterwards concentrated in vacuo. The residue is dissolved in acetone, and a solution of 1.8 g of oxalic acid in 10 ml of acetone is added. Crystals precipitate which, after recrystallisation from methanol/acetone, yield 5-(3'-isopropylamino-2'-hydroxypropoxy)-pyrimidine-hydrogen-oxalate, m.p. 166°–167°.

The 1-(5-pyrimidinyloxy)-2,3-epoxypropane used as starting material can be produced as follows:
9 ml of epichlorohydrin is added, with stirring, to 8.6 g of 5-hydroxypyrimidine and 21 g of potassium carbonate in 300 ml of acetone, and the whole is subsequently refluxed for 40 hours. The precipitate is filtered off under suction, the filter residue is washed with acetone, and the filtrate is concentrated in vacuo. There is obtained as residue a brown oil consisting of crude 1-(5-pyrimidinyloxy)-2,3-epoxypropane, which can be further used without purification.

EXAMPLE 92

0.65 g of 5-allyloxy-2-(3'-isopropylamino-2-hydroxypropoxy)-pyrimidine and 0.092 g of rhodium-tris(triphenylphosphine)-dichloride are dissolved in 20 ml of 90% ethanol. After the addition of 0.05 ml of triethylamine, the reaction solution is refluxed for 4 hours. The reaction mixture is then concentrated under reduced pressure, the residue is repeatedly extracted with 10 ml of hot acetone each time, the acetone extracts are heated with 0.5 g of active charcoal to boiling, and subsequently filtered hot through kieselguhr (Hyflo). The filtrate is concentrated to a volume of 5 ml, and a solution of 0.3 g of oxalic acid in acetone is added. There crystallises on trituration 5-hydroxy-2-(3'-isopropylamino-2'-hydroxypropoxy)-pyrimidine-hydrogen-oxalate, which is recrystallised from methanol/acetone, m.p. 165°–166° (decomposition).

EXAMPLE 93

1.6 g of 5-allyloxy-2-[3'-isopropyl-2'-phenyloxazolidinyl-(5')]-methoxypyrimidine is taken up in 6 ml of 1N hydrochloric acid. The whole is refluxed for ten minutes and then cooled; the precipitated benzaldehyde is extracted with ether, and 3 ml of 2N sodium hydroxide solution is added to the separated water phase. The base precipitating in oily form is extracted with ethyl acetate; the extract is washed with water, dried over sodium sulphate, filtered and concentrated under reduced pressure. The oily base obtained is dissolved in a little acetone, and a solution of 0.5 g of oxalic acid in 2 ml of acetone is added, whereupon 5-allyloxy-2-(3'-isopropylamino-2'-hydroxypropoxy)-pyrimidine-hydrogen-oxalate crystallises, which is recrystallised from methanol/acetone; m.p. 152°–153°.

The 5-allyloxy-2-[3'-isopropyl-2'-phenyloxazolidinyl(5')]-methoxypyrimidine can be produced as follows:

To a suspension of 0.13 g of sodium hydride in 5 ml of dimethoxyethane there is added 1.2 g of 2-phenyl-3-isopropyl-5-hydroxymethyl-oxazolidine, and stirring is maintained for 2 hours at room temperature. There is then added 1.2 g of 5-allyloxy-2-methylsulphonyl-pyrimidine dissolved in 20 ml of dimethoxyethane. Stirring is continued for 2 hours at room temperature, and the mixture is subsequently refluxed for 10 hours. The precipitated inorganic salt is separated by filtration; the filtrate is concentrated in vacuo, and the oily 5-allyloxy-2-[3'-isopropyl-2'-phenyloxazolidinyl-(5')]-methoxypyrimidine remaining is further processed without additional purification.

The 5-allyloxy-2-methylsulphonyl-pyrimidine used as starting material can be obtained as follows:

4.5 g of 5-hydroxy-2-methylthiopyrimidine, 9.0 g of potassium carbonate and 3.9 g of allyl bromide are together refluxed in 50 ml of acetone, with stirring, for 4½ hours. The inorganic salts are removed by filtration, and the filtrate is concentrated under reduced pressure. The oil remaining yields, from petroleum ether, 5-allyloxy-2-methylthiopyrimidine, m.p. 41°–42°.

3.5 g of 5-allyloxy-2-methylthiopyrimidine is dissolved in 30 ml of glacial acetic acid, and 20 ml of 20% hydrogen peroxide is added. After 46 hours at 20°, the solution is concentrated under reduced pressure at 20°. The residue yields, after crystallisation from ether, 5-allyloxy-2-methylsulphonylpyrimidine, m.p. 66°.

EXAMPLE 94

40 g of crude 2-{[3'-tert.-butyl-2'-phenyl-oxazolidinyl-(5')]-methoxy}-3-ethoxy-6-methyl-pyridine is stirred in 150 ml of 2N sulphuric acid for 2 hours at 20°–30°. The solution is extracted with 50 ml of ether; the aqueous phase is separated, and rendered alkaline with conc. sodium hydroxide solution. Extraction of the alkaline phase with methylene chloride and removal of the solvent by evaporation yield 25 g of a yellow oil which distills in a bulb tube at 110°–115°/0.02 Torr. The resulting 3-ethoxy-2-(3'-tert.-butylamino-2'-hydroxypropoxy)-6-methyl-pyridine yields with the half equivalent amount of fumaric acid a neutral fumarate, m.p. 169°–170° (from methanol/acetone).

The starting material can be produced in the following manner:

4.8 g of a sodium hydride dispersion (55%) is added portionwise in the course of 1½ hours at 0°–5° to a solution of 17.1 g of 3-ethoxy-2-chloro-6-methylpyridine and 25.8 g of 5-hydroxymethyl-3-tert.-butyl-2-phenyloxazolidine in 300 ml of hexamethylphosphoric acid anhydride. The reaction mixture is thereupon stirred for 2 hours at 20°–30° and for 16 hours at 70°; it is then poured into ice water, and 2-{[3'-tert.-butyl-2'-phenyloxazolidinyl-(5')]-methoxy}-3-ethoxy-6-methylpyridine is extracted with about 500 ml of ether. The crude product remaining after the ether has been evaporated off is used in this condition in further processing.

EXAMPLE 95

13.0 g of 3-chloro-2-(3-tert.-butylamino-2-hydroxy-1-propyloxy)-pyrazine, 4.65 g of ethylmercaptan and 4.05 g of sodium methylate in 250 ml of methanol are refluxed for 30 hours. After processing according to Example 8, there is obtained 14.0 g of crude base, and from this, with ethereal hydrochloric acid, there is obtained 3-ethylthio-2-(3'-tert.-butylamino-2'-hydroxy-1-propyloxy)-pyrazine-hydrochloride, which is recrystallised from methanol/ether; m.p 147°–148°.

EXAMPLE 96

13.0 g of 3-chloro-2-(3-tert.-butylamino-2-hydroxy-1-propyloxy)-pyrazine, 3.6 g of methylmercaptan and 4.05 g of sodium methylate in 850 ml of methanol are refluxed for 30 hours. After processing according to Example 8, there is obtained 11.9 g of crude base, and from this, with the calculated amount of fumaric acid, there is obtained 3-methylthio-2-(3'-tert.-butylamino-2'-hydroxy-1'-propyloxy)-pyrazine-fumarate (2:1), which is recrystallised from isopropanol; m.p. 184°–185°.

EXAMPLE 97

44.7 g of 2,3-dichloropyrazine and 70.5 g of 2-phenyl-3-tert.-butyl-5-hydroxymethyl-oxazolidine are dissolved in 300 ml of hexamethylphosphoric acid triamide. Into this solution at 0°–5° C. there is introduced in the course of 1 hour, with stirring, 13.1 g of a 55% suspension of sodium hydride in paraffin. The reaction mixture is subsequently stirred for 15 hours at room temperature; it is then poured into ice water and extracted with ether. The combined ether extracts are concentrated in a water-jet vacuum; the oily residue is taken up in 300 ml of 2N sulphuric acid, the solution is stirred for 2 hours at room temperature, and subsequently extracted with ether. The aqueous phase is made alkaline with conc. sodium hydroxide solution, and extracted with benzene/ether (1:1). The benzene/ether extracts are washed with water, dried over sodium sulphate, and concentrated in a water-jet vacuum. The residue is recrystallised from benzene/petroleum ether; there is obtained 3-chloro-2-(3'-tert.-butylamino-2'-hydroxy-1'-propyloxy)-pyrazine; m.p. 105°–106°.

EXAMPLE 98

Tablets containing 50 mg of active substance are prepared in the usual manner to have the following composition:

| Composition | |
|---|---|
| 2-(3'-isopropylamino-2'-hydroxy-propoxy)-3-chloro-pyridine hydrochloride | 50 mg. |
| Wheat starch | 59 mg |
| Lactose | 70 mg |
| Colloidal silica | 10 mg |
| Talc | 10 mg |
| Magnesium stearate | 1 mg |
| | 200 mg |

Preparation

The 2-(3'-isopropylamino-2'-hydroxy-propoxy)-3-chloropyridine hydrochloride is mixed with a part of the wheat starch, with lactose and with colloidal silica and the mixture is forced through a sieve, giving a powder mixture. A further part of the wheat starch is worked into a paste with a five-fold amount of water on a waterbath and the powder mixture is kneaded with this paste until a slightly plastic mass has been produced.

The plastic mass is forced through a sieve of about 3 mm mesh width and dried and the resulting dry granules are again forced through a sieve. The residual wheat starch, talc and magnesium stearate are then mixed in and the mixture is pressed to give tablets weighing 200 mg and having a breaking groove.

The daily dose is about ½ to 4 tablets in the case of a warm-blooded animal of about 75 kg body weight, but it is also possible to administer the corresponding dose of active compound in a single tablet of appropriate composition.

EXAMPLE 99

Tablets containing 50 mg of active substance are prepared in the usual manner to have the following composition:

| Composition | |
|---|---|
| 3-ethylthio-2-(3'-isopropylamino-2'-hydroxy-propoxy)-pyrazine fumarate | 50 mg |
| Wheat starch | 59 mg |
| Lactose | 70 mg |
| Colloidal silica | 10 mg |
| Talc | 10 mg |
| Magnesium stearate | 1 mg |
| | 200 mg |

Preparation

The 3-ethylthio-2-(3'-isopropylamino-2'-hydroxy-propoxy)-pyrazine fumarate is mixed with a part of the wheat starch, with lactose and with colloidal silica and the mixture is forced through a sieve, giving a powder mixture. A further part of the wheat starch is worked into a paste with a five-fold amount of water on a waterbath and the powder mixture is kneaded with this paste until a slighthly plastic mass has been produced.

The plastic mass is forced through a sieve of about 3 mm mesh width and dried and the resulting dry granules are again forced through a sieve. The residual wheat starch, talc and magnesium stearate are then mixed in and the mixture is pressed to give tablets weighing 200 mg and having a breaking groove.

The daily dose is about ½ to 4 tablets in the case of a warm-blooded animal of about 75 kg body weight, but it is also possible to administer the corresponding dose of active compound in a single tablet of appropriate composition.

EXAMPLE 100

Tablets containing 50 mg of active substance are prepared in the usual manner to have the following composition:

| Composition: | |
|---|---|
| 5-hydroxy-2-(3'-isopropylamino-2'-hydroxy-propoxy)-pyrimidine hydrogen-oxalate | 50 mg |
| Wheat starch | 59 mg |
| Lactose | 70 mg |
| Colloidal silica | 10 mg |
| Talc | 10 mg |
| Magnesium stearate | 1 mg |
| | 200 mg |

Preparation

The 5-hydroxy-2-(3'-isopropylamino-2'-hydroxy-propoxy)-pyrimidine hydrogen-oxalate is mixed with a part of the wheat starch, with lactose and with colloidal silica and the mixture is forced through a sieve, giving a powder mixture. A further part of the wheat starch is worked into a paste with a five-fold amount of water on a waterbath and the powder mixture is kneaded with this paste until a slightly plastic mass has been produced.

The plastic mass is forced through a sieve of about 3 mm mesh width and dried and the resulting dry granules are again forced through a sieve. The residual wheat starch, talc and magnesium stearate are then mixed in and the mixture is pressed to give tablets weighing 200 mg and having a breaking groove.

The daily dose is about ½ to 4 tablets in the case of a warm-blooded animal of about 75 kg body weight, but it is also possible to administer the corresponding dose of active compound in a single tablet of appropriate composition.

I claim:

1. A compound of the formula

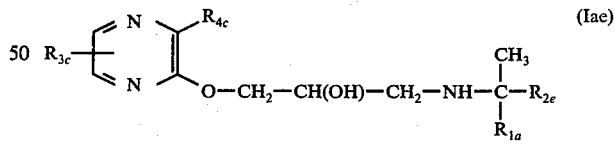

(Iae)

wherein $R_{1a}$ is hydrogen or methyl, $R_{2e}$ is methyl or 2-phenylethyl, $R_{3c}$ is hydrogen, hydroxy, bromine, methyl, 2-methoxyethyl or 2-methoxycarbonylaminoethyl, and $R_{4c}$ is hydrogen, chlorine, methoxy, 2-methoxyethoxy, allyloxy, methylthio, ethylthio, morpholino, 4-hydroxypiperidino, dimethylamino, isopropylamino, phenylthio or N'-methylpiperazino their antipodes or a therapeutically acceptable salt thereof.

2. The fumarate salt of the compound as claimed in claim 1 being 3-ethylthio-2-(3¹-isopropylamino-2¹-hydroxy-propoxy)-pyrazine.

3. A compound as claimed in claim 1 being 3-ethylthio-2-(3'-isopropylamino-2'-hydroxy-propoxy)-pyrazine or a therapeutically acceptable salt thereof.

4. A compound as claimed in claim 1 being 3-ethylthio-2-(3'-tert.-butylamino-2'-hydroxy-propoxy)-pyrazine or a therapeutically acceptable salt thereof.

5. The hydrochloride salt of the compound of claim 4.

6. A compound as claimed in claim 1 being 3-methylthio-2-(3'-tert.-butylamino-2'-hydroxy-propoxy)-pyrazine or a therapeutically acceptable salt thereof.

7. The fumarate salt of the compound of claim 6 formed with 1 mol of fumaric acid and 2 mol of the compound of claim 6.

8. A compound as claimed in claim 1 being 3-chloro-2-(3'-tert.-butylamino-2'-hydroxy-propoxy)-pyrazine or a therapeutically acceptable salt thereof.

9. A compound as claimed in claim 1 being 3-methoxy-2-(3'-isopropylamino-2'-hydroxy-propoxy)-pyrazine or a therapeutically acceptable salt thereof.

10. The hydrochloride salt of the compound of claim 9.

11. A pharmaceutical preparation useful as β-receptor blocking agent in the treatment of angina pectoris, hypertonia and disturbances of the rhythm of the heart comprising a therapeutically effective amount of a compound of the formula (Iae) as claimed in claim 1 wherein $R_{1a}$ and $R_{2e}$ have the meanings given, $R_{3c}$ and $R_{4c}$ have the meanings given except for hydrogen or a therapeutically acceptable salt of such a compound together with a pharmaceutically usable excipient.

12. A pharmaceutical preparation useful as β-receptor blocking agent in the treatment of angina pectoris, hypertonia and disturbances of the rhythm of the heart as claimed in claim 11 comprising a therapeutically effective amount of a compound selected from the group consisting of 3-ethylthio-2-(3'-isopropylamino-2'-hydroxy-propoxy)-pyrazine, 3-ethylthio-2-(3'-tert.-butylamino-2'-hydroxy-propoxy)-pyrazine, 3-methylthio-2-(3'-tert.-butylamino-2'-hydroxypropoxy)-pyrazine, 3-chloro-2-(3'-tert.-butylamino-2'-hydroxypropoxy)-pyrazine, 3-methoxy-2-(3'-isopropylamino-2'-hydroxypropoxy)-pyrazine or therapeutically acceptable salts thereof together with a pharmaceutically usable excipient.

13. A pharmaceutical preparation useful as β-receptor blocking agent in the treatment of angina pectoris, hypertonia and disturbances of the rhythm of the heart as claimed in claim 12 comprising a therapeutically effective amount of 3-ethylthio-2-(3'-tert.-butylamino-2'-hydroxy-propoxy)-pyrazine or a therapeutically acceptable salt thereof together with a pharmaceutically usable excipient.

14. A pharmaceutical preparation useful as cardiotonic in the treatment of insufficiency of the cardiac muscle comprising a therapeutically effective amount of a compound of the formula (Iae) as claimed in claim 1 wherein $R_{1a}$ and $R_{2e}$ have the meanings given, $R_{3c}$ and $R_{4c}$ denote hydrogen or a therapeutically acceptable salt of such a compound together with a pharmaceutically usable excipient.

15. A method of producing a β-receptor blocking effect in the treatment of angina pectoris, hypertonia and disturbances of the rhythm of the heart in a warm-blooded animal comprising the administration thereof of a therapeutically effective amount of a compound of the formula (Iae) as claimed in claim 1 wherein $R_{1a}$ and $R_{2e}$ have the meanings given, $R_{3c}$ and $R_{4c}$ have the meanings given except for hydrogen, or a therapeutically acceptable salt of such a compound.

16. A method of producing a β-receptor blocking effect in the treatment of angina pectoris, hypertonia and disturbances of the rhythm of the heart in a warm-blooded animal as claimed in claim 15 comprising the administration thereof of a therapeutically effective amount of a compound selected from the group consisting of 3-ethylthio-2-(3'-isopropylamino-2'-hydroxy-propoxy)-pyrazine, 3-ethylthio-2-(3'-tert.-butylamino-2'-hydroxy-propoxy)-pyrazine, 3-methylthio-2-(3'-tert.-butylamino-2'-hydroxy-propoxy)-pyrazine, 3-chloro-2-(3'-tert.-butylamino-2-hydroxy-propoxy)-pyrazine, 3-methoxy-2-(3'-isopropylamino-2'-hydroxy-propoxy)-pyrazine or therapeutically acceptable salts thereof.

17. A method of producing a β-receptor blocking effect in the treatment of angina pectoris, hypertonia and disturbances of the rhythm of the heart in a warm-blooded animal as claimed in claim 15 comprising the administration thereto of a therapeutically effective amount of 3-ethylthio-2-(3'-tert.-butylamino-2'-hydroxy-propoxy)-pyrazine or a therapeutically acceptable salt thereof.

18. A method of producing a β-receptor stimulating effect in the treatment of insufficiency of the cardiac muscle in a warm-blooded animal comprising the administration thereto of a therapeutically effective amount of a compound of the formula (Iae) as claimed in claim 1, wherein $R_{1a}$ and $R_{2e}$ have the meanings given, $R_{3c}$ and $R_{4c}$ denote hydrogen, or a therapeutically acceptable salt of such a compound.

19. The compound as claimed in claim 1 being 2-(3¹-isopropylamino-2¹-hydroxy-propoxy)-pyrazine.

20. The dihydrochloride salt of the compound of claim 19.

21. The fumarate salt of the compound of claim 18.

22. A pharmaceutical preparation useful as cardiotonic in the treatment of isufficiency of the cardiac muscle comprising a therapeutically effective amount of the compound 2-(3'-isopropylamino-2'-hydroxy-propoxy)-pyrazine as claimed in claim 1 or a therapeutically acceptable salt thereof together with a pharmaceutically usable excipient.

23. A method of producing a β-receptor stimulating effect in the treatment of insufficiency of the cardiac muscle in a warm-blooded animal comprising the administration thereto of a therapeutically effective amount of the compound 2-(3'-isopropylamino-2'-hydroxy-propoxy)-pyrazine as claimed in claim 1 or a therapeutically acceptable salt thereof.

24. A pharmaceutical preparation useful as β-receptor blocking agent in the treatment of angina pectoris, hyper-tonia and disturbances of the rhythm of the heart as claimed in claim 12 comprising a therapeutically effective amount of 3-ethylthio-2-(3'-isopropylamino-2'-hydroxy-propoxy)-pyrazine or a therapeutically acceptable salt thereof together with a pharmaceutically usable excipient.

* * * * *